US012012588B1

(12) United States Patent
Cameron et al.

(10) Patent No.: US 12,012,588 B1
(45) Date of Patent: Jun. 18, 2024

(54) METHODS AND SYSTEMS FOR THE USE OF PHOTOSYNTHETIC MICROBES AS MECHANICAL TRANSDUCERS AND SENSORS

(71) Applicant: The Regents of the University of Colorado, a body corporate, Denver, CO (US)

(72) Inventors: Jeffrey Carlyle Cameron, Boulder, CO (US); Kristin A. Moore, Boulder, CO (US); Evan B. Johnson, Boulder, CO (US); Jian Wei Tay, Boulder, CO (US); Janet B. Fox, Boulder, CO (US); Sabina Altus, Boulder, CO (US); David Bortz, Boulder, CO (US)

(73) Assignee: THE REGENTS OF THE UNIVERSITY OF COLORADO, A BODY CORPORATE, Denver, CO (US)

( * ) Notice: Subject to any disclaimer, the term of this patent is extended or adjusted under 35 U.S.C. 154(b) by 1223 days.

(21) Appl. No.: 16/036,645

(22) Filed: Jul. 16, 2018

Related U.S. Application Data

(60) Provisional application No. 62/532,882, filed on Jul. 14, 2017.

(51) Int. Cl.
*C12N 1/20* (2006.01)
*C07K 14/195* (2006.01)
*C12Q 1/02* (2006.01)
*C12N 1/12* (2006.01)
*C12R 1/01* (2006.01)

(52) U.S. Cl.
CPC ............ *C12N 1/205* (2021.05); *C07K 14/195* (2013.01); *C12Q 1/02* (2013.01); *C12N 1/125* (2021.05); *C12R 2001/01* (2021.05)

(58) Field of Classification Search
CPC .......... C12N 1/205; C12N 1/125; C12N 1/12; C12N 1/20; C12Q 1/02; C12Q 1/06; C12R 2001/01; C12R 2001/89
See application file for complete search history.

(56) References Cited

U.S. PATENT DOCUMENTS

2011/0179706 A1* 7/2011 Hunt ...................... A01G 7/045
47/58.1 LS

OTHER PUBLICATIONS

Shing et al., Sensors, 2013, 13: 6394-6404. (Year: 2013).*
Pakrasi, Alllu. Rev. Genetics, 1995, 29:755-76. (Year: 1995).*
Kirst et al., Biochemica et Biophysica Acta, 2014, 1837:1653-1664. (Year: 2014).*
Brayner et al., Anal Bioanal Chem, 2011, 401: 581-597. (Year: 2011).*

(Continued)

*Primary Examiner* — Allison M Fox
*Assistant Examiner* — Qing Xu
(74) *Attorney, Agent, or Firm* — Berg Hill Greenleaf Ruscitti LLP

(57) ABSTRACT

The invention relates to the novel use of photosynthetic microorganisms to allow for the generation of micron-scale optical output mechanical sensors. In one preferred embodiment, the invention includes systems, methods and compositions for the use of photosynthetic microbes as biologically-based micron-scale tunable, light/chemical-mechanical energy transducers, sensors, and/or actuators.

8 Claims, 45 Drawing Sheets
(44 of 45 Drawing Sheet(s) Filed in Color)

(56) References Cited

OTHER PUBLICATIONS

Yokoo et al., Photosynth Res., 2015, 126:33-46. (Year: 2015).*
Schuergers et al., eLife, 2016, 5:e12620:1-16. (Year: 2016).*
Mullineaux, Photosynth Res., 2008, 95: 175-182. (Year: 2008).*
Hader, Microbiological Reviews, 1987, 51:1-21. (Year: 1987).*
Kreimer, abstract, Comprehensive Series in Photosciences, 2001, 1:193-227. (Year: 2001).*
Moore et al., Nature Microbiology, 2020, 5: 757-767. (Year: 2020).*

\* cited by examiner

Chl or PB fluorescence low　　　　　　　　　　　　　　high

Soluble GFP

METHODS AND SYSTEMS FOR THE USE OF PHOTOSYNTHETIC MICROBES AS MECHANICAL TRANSDUCERS AND SENSORS

This application claims the benefit of and priority to U.S. Provisional Application No. 62/532,882, filed Jul. 14, 2017, the entire specifications and figures of which is hereby incorporated, in its entirety by reference.

TECHNICAL FIELD

The inventive technology generally relates to mechanisms of cellular regulation of light harvesting. In particular, the invention relates to the novel use of photosynthetic microorganisms to allow for the generation of micron-scale optical output mechanical sensors and transducers of light-energy into mechanical-energy.

BACKGROUND OF THE INVENTION

Photosynthesis is an energy storage process that converts light into more stable forms of chemical energy for cellular maintenance and the production of biomass and biomolecules. Multiple regulatory processes function to prevent over-excitation of reaction centers and production of reactive oxygen species (ROS) that can damage cellular components. Source-sink regulation of photosynthesis is a general strategy used to balance light capture (source) with the cells ability to utilize or dissipate the light energy (sink) through metabolic (e.g. carbon fixation) or energy quenching processes (e.g. NPQ, water-water cycle). In plants, source and sink tissues are spatially separated; photosynthetic source tissues (leaves containing chloroplasts) produce sugars that are transported to distal sink tissues (e.g. roots, seeds, tubers) for storage in the form of starch (e.g. roots, seeds).

In contrast, unicellular photosynthetic organisms' source-sink processes occur within the same cell. An example of such photosynthetic organisms includes cyanobacteria which are photosynthetic microbes that use light energy to oxidize water for the reduction of $CO_2$ into biomolecules used in the generation of new biomass. In cyanobacteria, photosynthesis is regulated in response to light intensity and wavelength, temperature, and nutrient availability (e.g. $CO_2$). This robust regulation and adaptability of photosynthesis has allowed cyanobacteria to thrive in some of Earth's most diverse and extreme terrestrial and aquatic habitats (e.g. arctic, deserts, hot springs, oceans, hypersaline and alkaline lakes) as free-living microbes and in symbiotic relationships (e.g. lichen, cycads, sponges).

For example, cyanobacteria are able to store carbohydrate polymers in the form of glycogen, but formation of biomass (new cells) is the main sink for electrons derived from photosynthetic water oxidation. Oftentimes, carbon stored during the light is consumed in the dark to provide ATP and NADPH for cellular maintenance and energy-intensive processes such as fixation of $N_2$ into ammonia. Disruption of the source-sink balance by increasing the light intensity or decreasing the cells ability to use this energy can lead to the production of ROS and initiation of non-photochemical quenching (NPQ), alternative electron flow pathways, and state transitions to balance energy flow.

Cyanobacteria more specifically utilize light harvesting antennae (phycobilisomes) comprised of pigment-protein complexes to funnel energy to the reaction center to drive photochemistry. This process is regulated to maintain an optimal source:sink balance, with the source being the energy input (light) and the sink being carbon-fixation, generation of new biomass. In the case where the source is too high (high light environment), or the source is too low (low CO2 environment), the cell can adapt by (de)coupling the phycobilisome with the reaction center to re-balance the source:sink ratio. In addition, long-term acclimation including degradation of light harvesting complexes and short-term processes including non-photochemical quenching of incident light is also important for balancing the reaction center.

Despite this understanding of photosynthetic regulation in cyanobacteria, it has remained challenging to gain mechanistic insight into these regulatory processes because of the difficulty in achieving steady-state growth conditions in batch cultures due to constant attenuation of light availability through cell-cell shading and unknown levels of heterogeneity in the population. Furthermore, ensemble based techniques lack the ability to track phenotypes across individual single-cell lineages and is unable to discern subtle but important variations within a population.

Because photosynthesis is regulated in response to many diverse stimuli including light intensity and wavelength, nutrient availability, and temperature, understanding how photosynthesis is regulated is critical to understanding how to increase photosynthetic efficiency for the benefit of society and the environment.

The present invention involves new and novel mechanisms for the regulation of photosynthesis in single-celled organisms. The novel systems, methods and compositions described herein employ long-term, quantitative time-lapse fluorescence microscopy to visualize the growth dynamics of wild-type and mutant cyanobacterial strains while controlling temperature, light, nutrient, and growth-substrate properties. Quantitative image processing with custom algorithms enables the tracking of individual cells and single-cell derived lineages for multiple generations and monitor cellular physiology at sub-cellular resolution.

In particular, the invention includes novel systems, methods and compositions demonstrating that mechanical perturbations lead to attenuation of photosynthesis and can play a major role in governing cellular fitness and productivity in cyanobacteria. The mechanistic basis of this phenomenon was demonstrated using mathematical modeling, electron microscopy, mutational analysis, and CRISPRi-based dynamic gene regulation. The inventive technology described herein demonstrates how photosynthetic organisms navigate the physical environment and employ source-sink regulation of photosynthesis. Moreover, the inventive technology discloses novel mechanisms by which cellular metabolism is regulated through mechanical processes.

SUMMARY OF THE INVENTION

As detailed below, the present inventors demonstrate that cyanobacterial cells produce an optical signal upon mechanical stimulation due to regulation of the light harvesting complexes associated with the photosynthetic reaction centers. When cells interact with other cells or inert physical objects, the light harvesting complexes disassociate from the membrane and become highly fluorescent because they no longer transfer most energy from the absorbed light to the reaction centers (e.g. Photosystem I and Photosystem II) that typically results in photochemistry.

Based on these observations by the current inventors that cyanobacteria are able to convert light into mechanical energy and simultaneously provide an optical signal during mechanical confinement that is related to incident light energy, one aim of the current invention may include novel systems, methods and compositions for the use of photosynthetic microbes as micron-scale tunable, light/chemical-mechanical energy transducers, sensors, and/or actuators.

Another aim of the current invention may include a screening method, or assay for identifying photosynthetic bacterium and/or strains that may exhibit enhanced, nominal and/or diminished transduction of light energy into a mechanical force and vice versa.

Other features and advantages of the invention will be apparent from the detailed description, figures, and claims provided below.

BRIEF DESCRIPTION OF THE FIGURES

This patent application file contains at least one drawing executed in color. Copies of this patent application publication with color drawing(s) will be provided by the Office upon request and payment of the necessary fee. Further, the above and other aspects, features, and advantages of the present disclosure will be better understood from the following detailed descriptions taken in conjunction with the accompanying figures, all of which are given by way of illustration only, and are not limiting the presently disclosed embodiments, in which.

DETAILED DESCRIPTION OF THE INVENTION

The present invention includes a variety of aspects, which may be combined in different ways. The following descriptions are provided to list elements and describe some of the embodiments of the present invention. These elements are listed with initial embodiments, however it should be understood that they may be combined in any manner and in any number to create additional embodiments. The variously described examples and preferred embodiments should not be construed to limit the present invention to only the explicitly described systems, techniques, and applications. Further, this description should be understood to support and encompass descriptions and claims of all the various embodiments, systems, techniques, methods, devices, and applications with any number of the disclosed elements, with each element alone, and also with any and all various permutations and combinations of all elements in this or any subsequent application.

Figure 1:
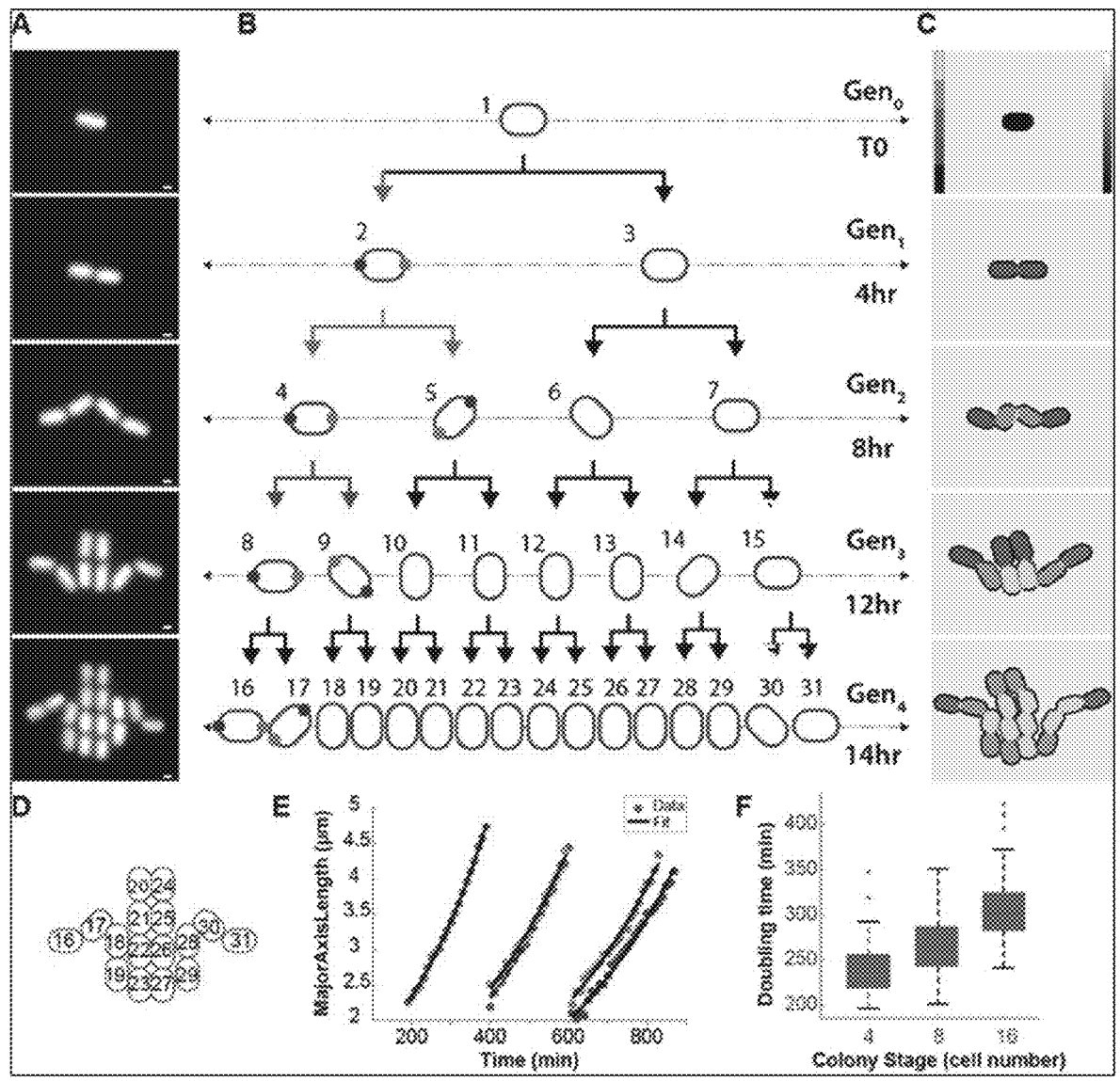
FIG. 1: Analysis of single-cell derived lineages and microcolony structure. A) Images of microcolony formation using YFP fluorescence as cell marker. B) Lineage of cyanobacterial growth across four generations. The position of the old (blue) and new (orange) poles are indicated. C) Simulation of microcolony growth. Cells are colored based on the summed mechanical perturbation (low to high; black to yellow) and outlined based on relative cell-cell interaction force (low to high; black to white). D) Lineage information mapped on to colony position. E) Representative single-cell growth curves of cells corresponding to the left-side of the single cell lineage in (B). F) Mean single-cell doubling time based on colony stage.
Figure 2:
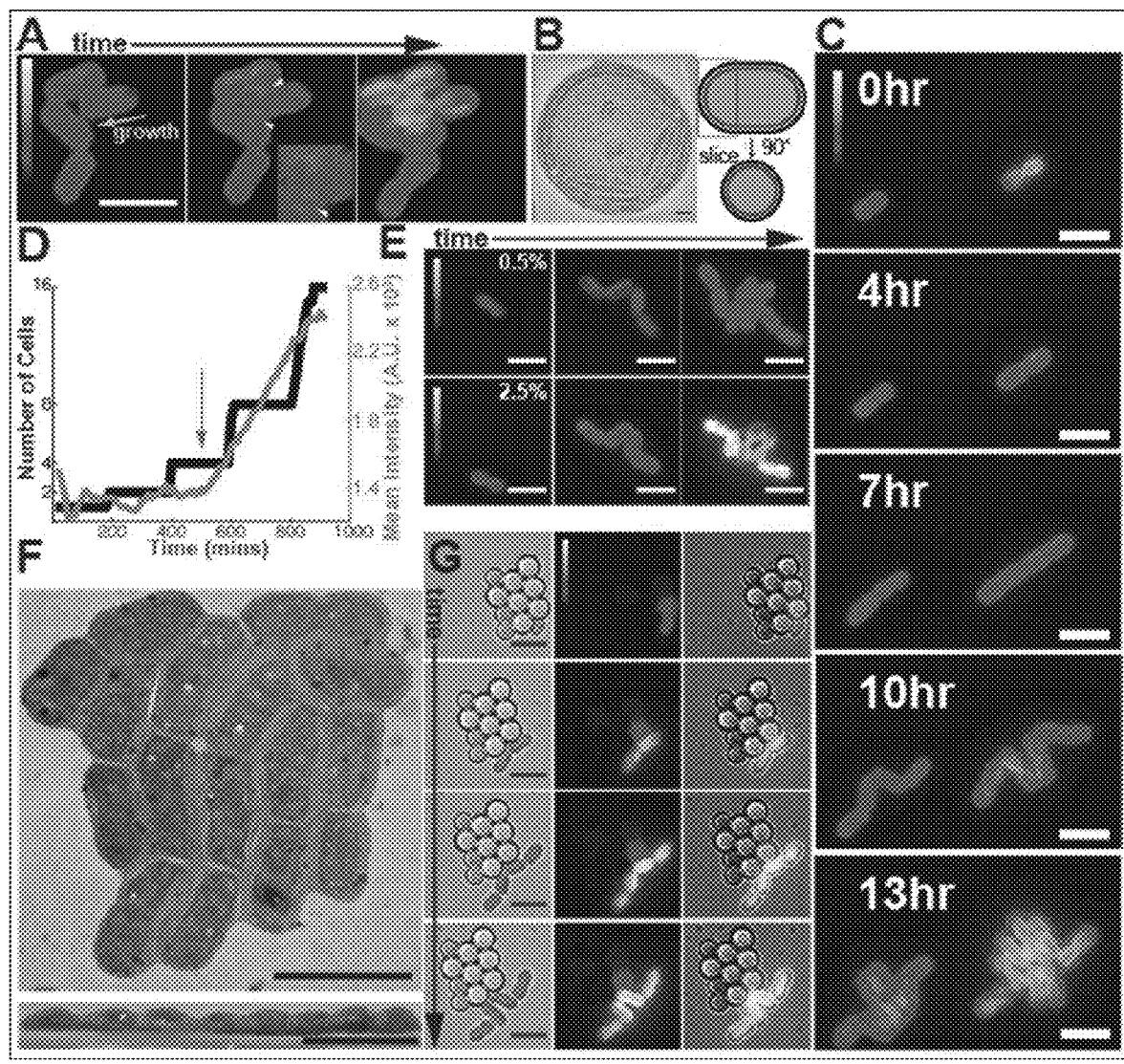
FIG. 2: Mechano-optical interactions of cyanobacterial growth on solid substrates. A) Cell-cell interactions result in increased fluorescence. B) Thylakoid membrane structure in *Synechococcus* sp. PCC 7002. C) Fluorescence is related to colony structure and not illumination time. D) Rise of fluorescence during four-cell stage. E) Growth and fluorescence based on agar concentration. F) Transmission electron micrographs of native cyanobacterial colonies sectioned from top (top) or side (below) profiles. G) Growth and interactions of cells with polystyrene beads.
Figure 3:
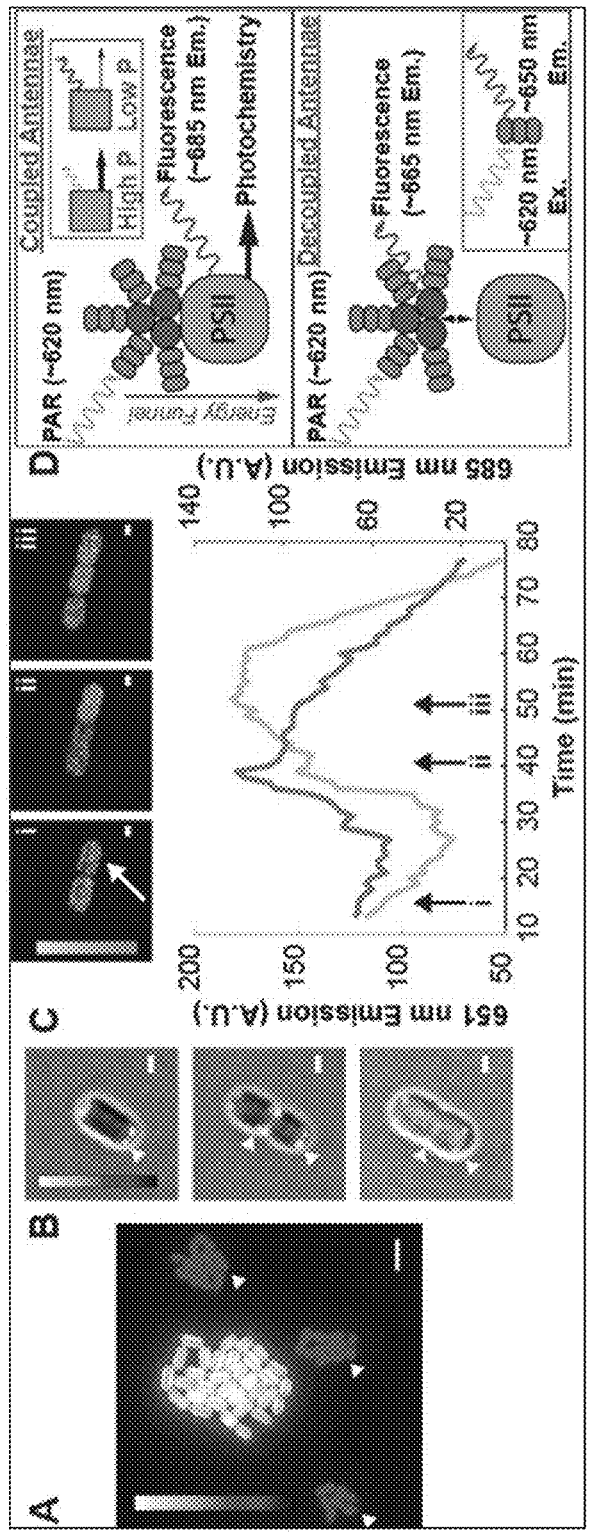
FIG. 3: Analysis of phycobilisome location and dynamics in single-cells A) Fluorescence of wild-type and Δcpc (arrow) microcolonies grown side-by side. B) Fluorescence of Apc core in Δcpc mutants (top two panels) and wild-type (lower panel). C) Spectral imaging of colony on 2% agar. D) Model of antennae (de)coupling dynamics.
Figure 4:
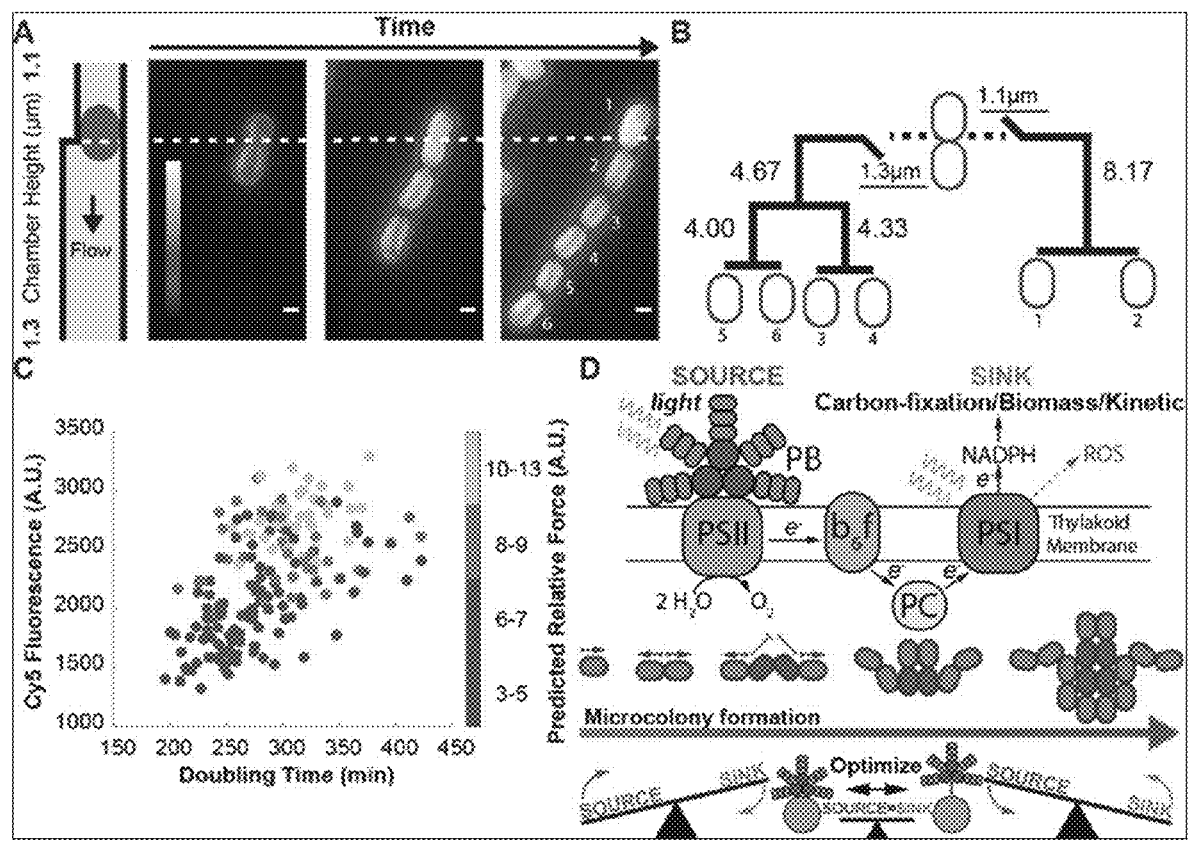
FIG. 4: Mechanical regulation of photosynthesis. A) Growth in microfluidic device at intersection between constrained and unconstrained growth. B) Lineage analysis of growth in microfluidic device, with chamber height (underlined) and growth rates indicated. C) Relationship between growth, fluorescence, and relative interaction forces in single cells. D) Model of mechanical regulation of photosynthesis to optimize source:sink balance.

As noted above, in addition to being regulated by light, temperature, and nutrient availability, as shown herein, photosynthesis is regulated mechanically. As demonstrated in FIGS. 1-4, photosynthetic cyanobacterial cells are unable to expand, for example if they are in the interior of a colony or adjacent to a physical barrier. In this embodiment, as outlined in FIG. 3D, the light-harvesting complex disassociates from the photosystem II, reducing the amount of energy transfer to the photosynthetic reaction center. The function of this disassociation may be to protect the cell from light that is in excess to what it can use. As noted above, this is especially important in photosynthetic organisms, such as cyanobacteria, because excess light can lead to the production of reactive oxygen species that can damage the cell.

As highlighted in the accompanying figures, in certain embodiments of the inventive technology, photosynthetic microbes, such as cyanobacteria, may convert light into mechanical energy. In certain embodiments of the invention, the conversion of electromagnetic energy (light) into kinetic (mechanical) energy may be used in biologically-based microelectronics, micro-machines, actuators, transducers sensors, etc. For example, a radiometer converts light into mechanical energy through generation of differential pressures due to differential light absorption on a surface. In the instant inventive technology, photosynthetic bacteria such as cyanobacteria, may convert light into mechanical energy by conservation/funneling the energy through one or more metabolic pathways.

In other alternative embodiments, one or more inputs may be modulated to generate a desired or optimal output. For example, the amount, frequency and wavelength of a light energy input may be applied to one or more photosynthetic microbes that may further generate a desired and/or optimal mechanical energy output. In additional embodiments, genetic, chemical, and environmental perturbations can be used to modulate or tune the transduction of energy through the system. For example, in one embodiment, the truncation of the light harvesting complex (reduce source strength) may reduce the absorption cross-section and reduce the efficiency of conversion of incident light into mechanical energy. Furthermore, altering the efficiency of sink processes by modulating the carbon-fixing machinery can also affect the mechanical properties of the cell. In additional embodiments, the genetic manipulation of structural and regulatory genes that affect cytoskeletal, membrane, osmotic potential, surface properties may be modified to tune the efficiency of energy conversion through the system.

The conversion of light into mechanical energy may be used not only for cellular growth, but to generate the force required to grow and push through a solid medium (e.g. growth on solid agar support). As such, in certain embodiments one or more photosynthetic microbes may be grown on a solid media and observed to varying growth patterns indicative of the generation, or lack of generation of mechanical forces. Such an embodiment maybe used to screen for mutants with altered mechanical properties because if it is hard to grow (due to a stiff surface), the inherent sink strength (due to physical restriction of new biomass formation) is reduced, and typical light intensities become toxic. For example, in one embodiment the present inventors demonstrate that a cyanobacterium mutant lacking the phycobilisome is unable to grow on stiff agar (>1%), but grows well on 0.5% agar. In additional embodiments, the present inventors demonstrate that by unencapsulating the carbon-fixing enzyme, RuBisCO, which is typically housed inside a protein-based organelle called the carboxysome, cells are able to grow on much stiffer agar (>2.5%) compared to the wild-type.

Generally referring to the FIGS. 1-4, increased mechanical pressure on growing cyanobacteria leads to disassociation of the light-harvesting complexes and increased fluorescence intensity of the cells, providing an optical readout of mechanical stress. In this embodiment, the fluorescence intensity may be an output signal that may be observable and/or recordable such that cyanobacteria may act as a sensor of, for example photosynthetic activity, mechanical force, and/or microcolony formation dynamics and the like. As noted above, this increased fluorescence intensity is the result of the phycobilisome antennae becoming decoupled from the reaction center; if light energy is not funneled to the reaction center and is therefore not used for photochemistry, the energy is dissipated as heat and fluorescence.

In one embodiment, the current invention relates to the utilization of the aforementioned photochemistry in microbes to allow for the generation of micron-scale optical-output mechanical sensors. For example, in certain embodiments of the present invention, this process can be resolved at sub-cellular resolution, providing an optical-output of forces in a complicated environment at sub-micron scales. Certain embodiments of the invention may be utilized to produce biological based sensors that report on mechanical and/or other forces. More broadly, in certain embodiments, this fluorescence output could also be coupled to report on other stimuli including light levels and/or nutrient availability.

Another embodiment of the invention may include the novel use of photosynthetic microorganisms, such as cyanobacteria, as mechanical sensors of photosynthesis. In one preferred embodiment, such a mechanical sensor of photosynthesis may be light-dependent, and tunable based on manipulation of a light energy input. An additional embodiment of the current invention relates to the utilization of the aforementioned photochemistry in microbes to allow for the generation of micron-scale optical output mechanical sensors that may be tunable, for example in response to varying light and/or mechanical force inputs, as well as other environmental inputs, such as nutrient availability and/or micro-environmental conditions such as pH.

Additional embodiments of the current invention may include the utilization of the aforementioned photochemistry in microbes to allow for the generation of a light dependent, mechanical transducer that may perform micron-scale actions in response to a variable light-stimulus. In one embodiment, the invention may include the use of photosynthetic microbes that may form a mechanical-energy transducer that may accept a mechanical energy input and transduce such mechanical energy into a light energy output. In still other embodiments, the invention may include a light energy transducer that may accept a light energy input and transduce such light energy into a mechanical energy output. It should be noted that in either of the above embodiments, such transduction of light, and or mechanical energy may be controlled, or tunable in response to controlled or natural variations of the input energy, such as light intensity and/or wavelength, mechanical force, microcolony morphology, genotypic and/or phenotypic variations as well as microenvironmental variations that may results from nutrient availability, pH variations, as well as physical presence of non-microbial component structures.

An additional embodiment of the current invention may include the utilization of the aforementioned photochemistry in microbes to allow for the generation of light dependent, mechanical actuator that may, in one embodiment, convert a light-energy input into a mechanical energy output. In additional embodiments, the invention may include to the utilization of the aforementioned photochemistry in microbes to allow for the generation of micron-scale actuator/sensor that may, in one embodiment, convert a mechanical-energy input into a light energy output.

An additional embodiment of the current invention may include to the utilization of the aforementioned photochemistry in microbes to allow for the generation of a tunable bio-transducer that may, in one preferred embodiment, convert a light-energy input into a mechanical energy output. In this this preferred embodiment generally shown in FIG. 13B, an electromagnetic energy, or light input may be applied to one or more photosynthetic microbes, such as cyanobacteria. The intensity or wavelength of the light input may be adjusted to generate and or transduced a larger and/or smaller input of energy through the system to be converted into a mechanical or kinetic force output.

Figure 13:
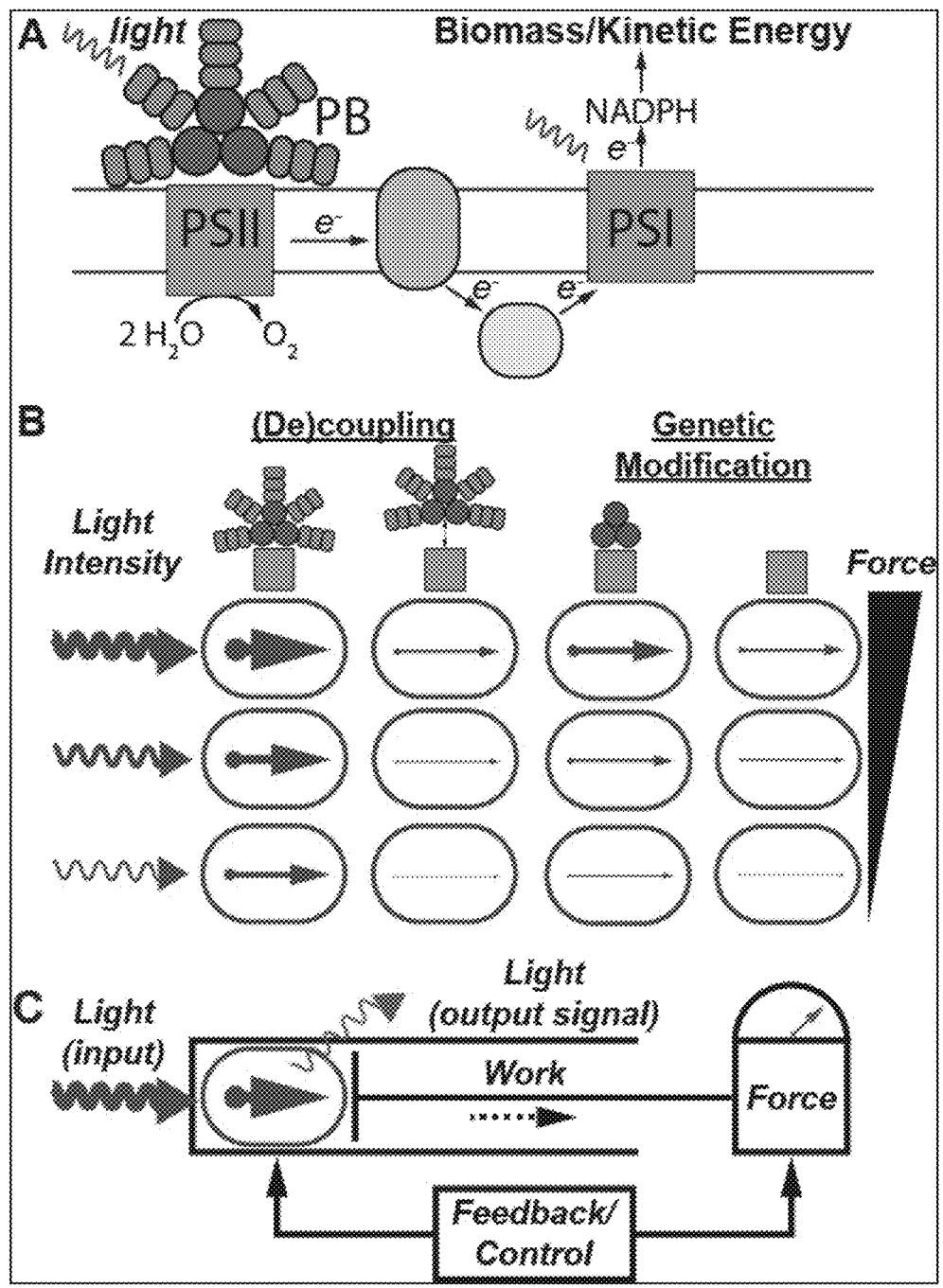
FIG. 13: Model of using photosynthetic microbes as light-dependent, tunable, mechanical actuator, sensor, transducers. A) Photosynthetic electron transport chain. B) Tunable mechanics. C) Use of cyanobacteria to perform mechanical work/sensing.
Figure 14:
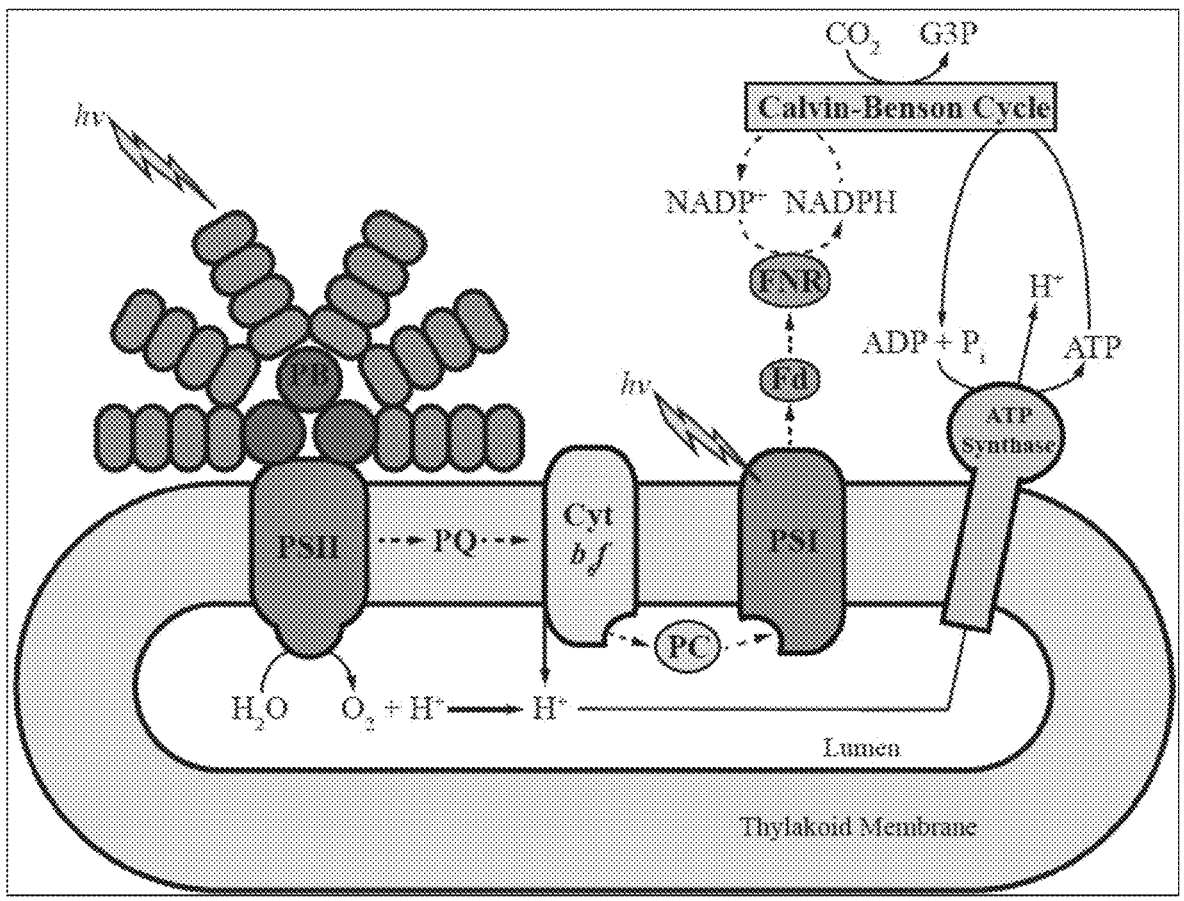
FIG. 14: Describes the dissociation of PB from a/the reaction center leads to increase fluorescence.
Figure 15:
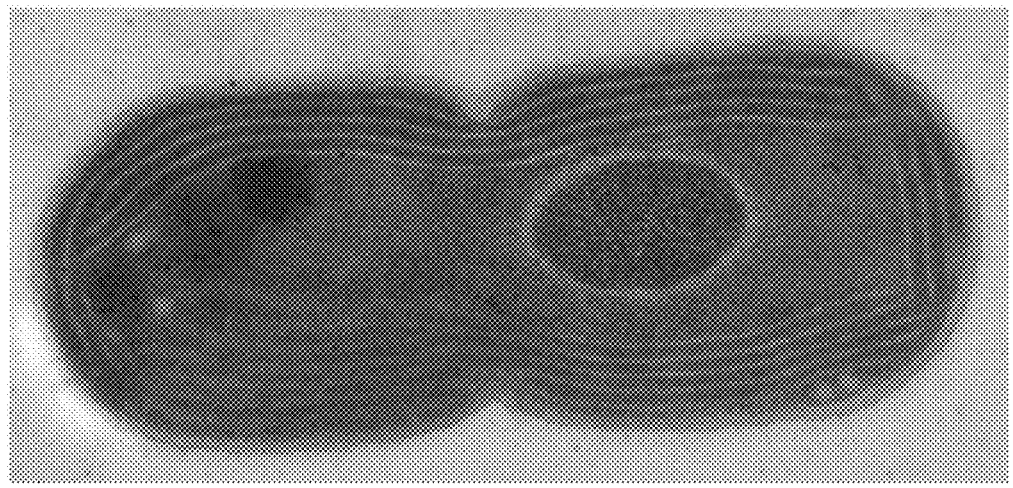
FIG. 15: Describes a native membrane arrangement of a dividing cyanobacteria cell (*Synechococcus* sp. strain PCC 7002) which may act as a biological force sensor.
Figure 16:
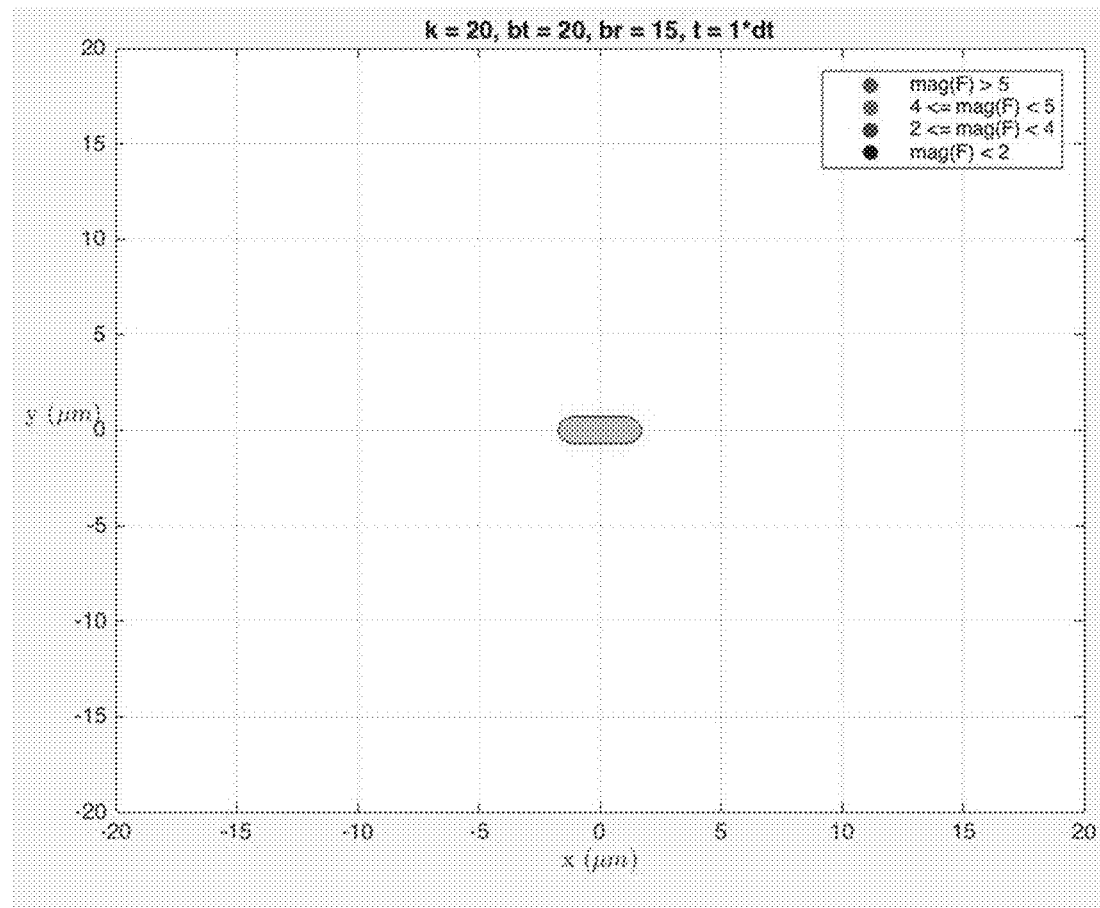
FIG. 16: Demonstrates experimental data of one embodiment of the invention describing the simulation of mechanical forces in microcolony.
Figure 17A:
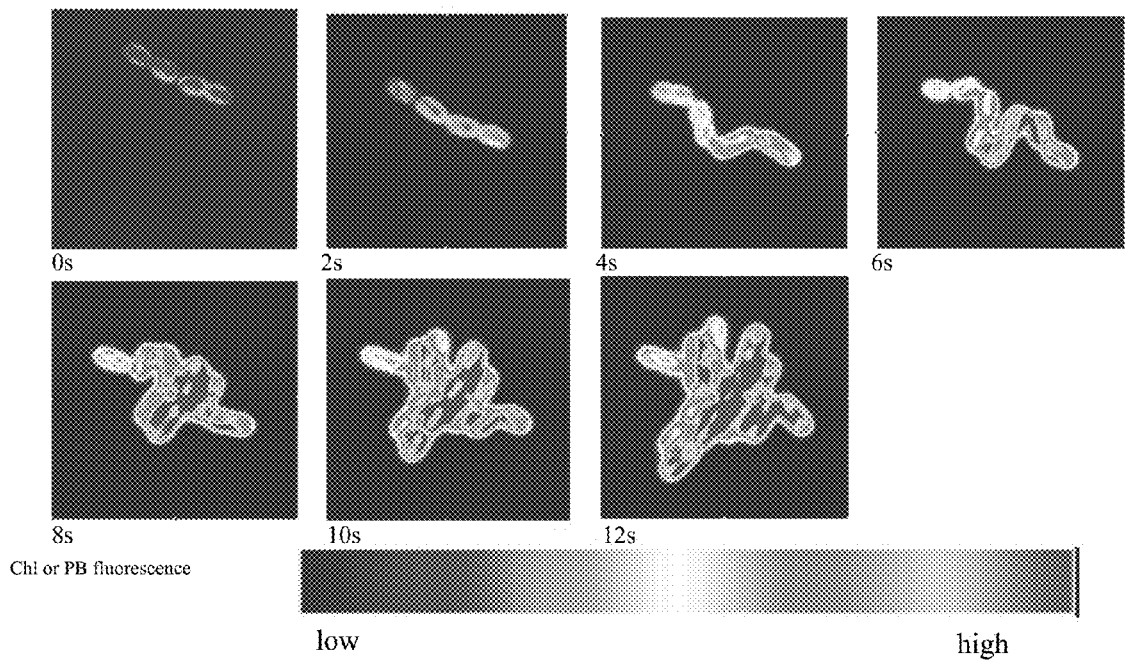
FIG. 17A-B: Demonstrates time-course images of experimental data of one embodiment of the invention where increased Chl/PB fluorescence indicates decreased photosynthetic capacity.
Figure 17B:
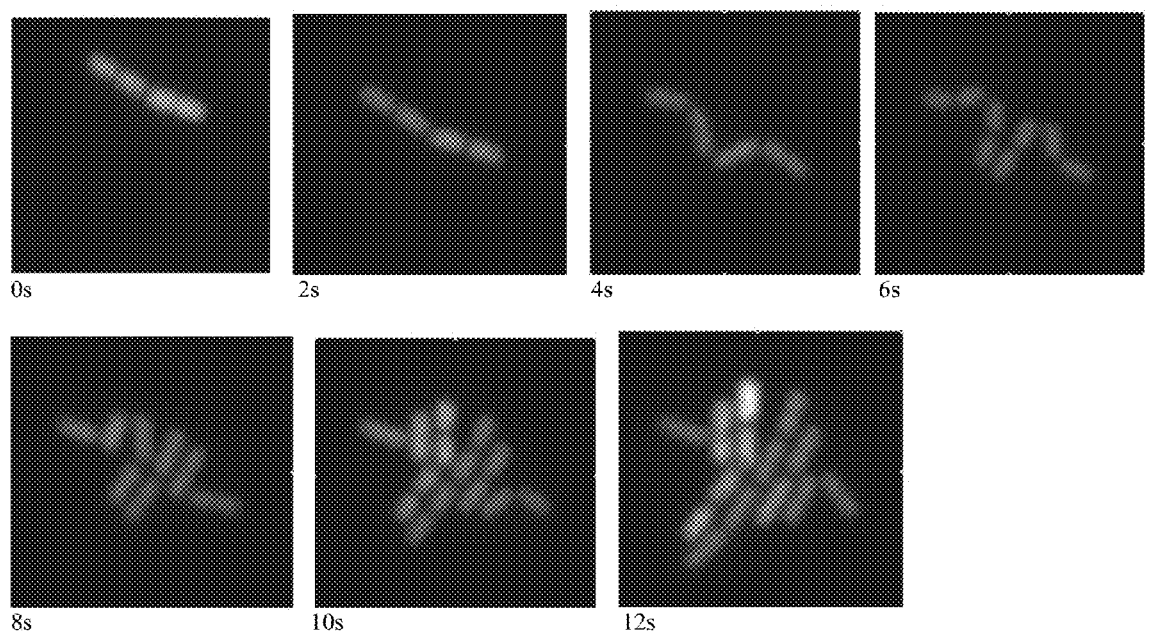

Again as shown in FIG. 13B, in this embodiment, the coupling and/or de-coupling of the phycobilisome antennae from the reaction center, whether through a cell-induced process, or through other genetic and/or other artificial manipulations may further alter the transduction of the light energy input into a kinetic force output within the system. As noted above, the decoupling of phycobilisome antennae from the reaction center may re-balance the source:sink ratio. This decoupling action may further increase the observable fluorescence intensity as the light energy is not funneled to the reaction center and is therefore dissipated as heat and fluorescence. Such change in heat and fluorescence may generate an observable and recordable signal indicating transduction of energy through the system.

As noted in FIG. 13B, in certain embodiments, a photosynthetic microbe such as cyanobacteria may be genetically modified to interrupt and/or remove phycobilisome antennae or other molecular structures involved in the transduction of light into a kinetic force.

In one preferred embodiment, the invention may include a bio-actuator. As outlined in FIG. 13C, in this embodiment, one or more photosynthetic microbes, such as cyanobacteria may be configured to receive a light input. This light input may be transduced through one or more cells generating a mechanical or kinetic output which may be coupled with a movable component. In this embodiment, the light energy may be converted into a kinetic energy that may be outputted from the cell and act on such movable component causing its displacement or, in other words generating "work." In this embodiment, a light or output signal may be generated, for example a fluorescent or heat output signal may be outputted and measured. Such output signal may indicate and quantify the amount of kinetic energy generated from the light input. Further, as shown in FIG. 13C, the movable component(s) may be coupled with, or in communication with a force sensor, such that a feedback/control may be established to modulate the light input or transduction of energy through the cell. In this manner, the work performed by the system may be regulated through a feedback/control system.

The term "cyanobacteria," as used herein, refers to prokaryotic organisms formerly classified as the blue-green algae. Cyanobacteria are a large and diverse group of photosynthetic bacteria which comprise the largest subgroup of Gram-negative bacteria. Cyanobacteria were classified as algae for many years due to their ability to perform oxygen-evolving photosynthesis. (Curtis, "Cyanobacteria, Molecular Genetics", Encyclopedia of Microbiology, vol. 1, 627 (1992)). While many cyanobacteria have a mucilaginous sheath which exhibits a characteristic blue-green color, the sheaths in different species may also exhibit colors including light gold, yellow, brown, red, emerald green, blue, violet, and blue-black. (Raven et al., Biology of Plants, Fourth Edition, 183-185, (1986)), included herein by reference. Cyanobacteria include *Microcystis aeruginosa, Trichodesmium erythraeum, Aphanizomenon flos-aquae, Spirulina*, and *Anabaena flos-aquae*. One of ordinary skill in the art can identify other cyanobacteria that can be used with the compositions and methods disclosed herein.

As used herein, the term "sensor" or "biosensor" refers to any composition or organism that is partially or entirely composed of biological molecules. In a traditional sense, the term refers to an analytical tool or system consisting of a biological material in contact with a suitable input which may generate the biochemical signal into a quantifiable signal. For example, in one embodiment, a sensor, or biosensor may be a photosynthetic cyanobacteria that may receive a light energy input that may be converted into mechanical energy and which further provides an optically observable signal, such as heat or fluorescence.

As used herein, the term "transducer" or "bio-transducer"—as interchangeably used herein—refers to a biological transducer composition and/or organism that is capable of converting a non-electrical phenomenon into a signal or information, such as an electrical, light energy, and/or mechanical information, and transmitting the information to another organism and/or device where it may be interpreted.

As used herein, the term "actuator" or "bio-actuator"—as interchangeably used herein—refers generally to biological actuator composition and/or organism that is capable of receiving a signal or input, such as a light energy input, and translates such input into a mechanical energy output which may be used to generate work, for example by displacing the one or more target components in one or more directions of movement or rotation.

As used herein, the term "tunable" refers generally to the ability to modulate and/or optimize an input or output of a biological system. For example, a light energy input applied to a bio-actuator of the current invention may be modulated to generate a desired or optimal mechanical energy output. Additional inputs may include genetic, chemical and/or environmental perturbations that may modulate the transduction of energy through the system.

The terminology used herein is for describing embodiments and is not intended to be limiting. As used herein, the singular forms "a," "and" and "the" include plural referents, unless the content and context clearly dictate otherwise. Thus, for example, a reference to "a bacterium" may include a plurality of bacterium. Unless defined otherwise, all scientific and technical terms are to be understood as having the same meaning as commonly used in the art to which they pertain.

The term "including" is used herein to mean, and is used interchangeably with, the phrase "including but not limited to." The term "or" is used herein to mean, and is used interchangeably with, the term "and/or," unless context clearly indicates otherwise.

EXAMPLES

Example 1: Cellular Imaging of Cyanobacterium Growth and Microcolony Formation To overcome the limitations in studying photosynthetic regulation outlined above, the present inventors utilized quantitative long-term time-lapse fluorescence microscopy to gain insight into source-sink regulation of photosynthesis in the model cyanobacterium *Synechococcus* sp. PCC 7002 (hereafter PCC 7002) in single-cells at sub-cellular resolution. This approach enabled the present inventors to capture the dynamics of exponentially growing cells (doubling time ~3 hr) in precisely controlled environmental conditions. Transillumination with a calibrated and collated solid-state light source (RGB) provided control over growth-light intensity and wavelength, and electronic synchronization with a sensitive high speed sCMOS camera enabled simultaneous quantitative imaging during growth. As generally shown in FIGS. 1A and 20. In this embodiment, because cells were grown in 2-D layers on solid medium or in the confines of a microfluidic chamber, cell-cell shading was avoided allowing the present inventors to film the growth of single-cell derived lineages under constant illumination, temperature, and nutrient concentration for multiple generations.

Again, as generally shown in FIG. 1A, the present inventors found that microcolony formation in PCC 7002 was highly reproducible for at least 4-5 doublings (16-32 cell stage) under standard growth conditions, producing compact structures of parallel cells flanked by perpendicular cells resembling "arms". As shown in FIGS. 1B-C, this distinct colony morphology preserves cell-lineage information and cell polarity, allowing the present inventors determine the ancestry of each cell based on colony position alone. Furthermore, as demonstrated in FIG. 1D generally, it enables pair-wise comparisons of multiple single-cell phenotypes (e.g. growth rate) within individual cells and between different single-cell derived microcolonies.

Example 2: Non-Random Distributions of Cells within the Cyanobacteria Colonies are Driven by Discrete Mechanical Interactions Between Adjacent Cells As demonstrated in FIG. 1E, the present inventors determined that a mathematical model could accurately simulate the morphological growth dynamics and predict the relative mechanical forces acting on cells within the colony. Empirically derived model parameters including cell dimensions and growth rates, were extracted from time-series analysis of movies using custom in-house segmentation and cell-tracking algorithms. A purely stochastic model could not reproduce the colony dynamics of PCC 7002 in contrast to other Gram-negative bacteria such as *E. coli*. This implies that discrete physical forces overcome stochastic processes and strongly influence colony morphology in PCC 7002. It was evident to the present inventors from the simulation that the mechanical forces encountered by cells within the individual microcolony increased as the cell number increased, with the interior cells experiencing the most severe mechanical interactions. As shown in FIG. 2F, experimentally measured single-cell growth rates also decreased as microcolony size increased, demonstrating a possible relationship between mechanical perturbations and metabolic processes.

Example 3: Demonstration of the Relationship Between Mechanical Perturbations and Cellular Physiology in Cyanobacteria To further explore the potential relationship between mechanical perturbations and cellular physiology, the present inventors investigated the photosynthetic properties of PCC 7002 by quantifying the endogenous fluorescence emission following excitation of the light harvesting antenna (phycobilisomes) and photosystem II (PSII) reaction centers in rapidly growing cells.

As noted above, in cyanobacteria, the fluorescence yield following excitation of the reaction centers (either directly or through energy funneling via antennae proteins) is inversely related to photochemistry. Unexpectedly, as shown in FIG. 2A, the present inventors observed a rapid increase in fluorescence emission during cell-cell contact upon microcolony formation. As demonstrated in FIG. 2B, the present inventors observed that the increased fluorescence was initially localized to the site of contact, corresponding to the outer leaflets of thylakoid membranes oppressed to the plasma membrane, but eventually propagated to the interior of the cell, which lacks photosynthetic membranes.

It is known that over-excitation of PSII reaction centers, following high-light exposure and disruption of the source-sink balance, results in disassociation of antennae complexes from the PSII reaction centers and high-fluorescence emission of the antennae terminal emitter, Apc. This phenomenon can be rapidly initiated with a short pulse of 640 nm light in a microscope, resulting in rapid (<1 s) re-distribution of phycobilisomes from the periphery to the interior of the cell (see FIG. 20). However, under steady-state growth conditions, light fluence is held constant and intensity is well below the threshold to induce this response. Moreover, as shown in FIG. 1C, the rise in fluorescence emission of three adjacent microcolonies, separated by <20 µm and experiencing identical light conditions, is correlated to colony stage and not to time of light exposure.

Referring generally to FIG. 2D, high fluorescence is typically observed in the single-cell stage as cells acclimate to microscopic growth conditions (e.g Lag phase) followed by a rapid transition to a low-fluorescence state immediately preceding exponential growth, then transitioning back to a high-fluorescent state at the 4-cell stage. Because cells in the interior of the colony appeared to brighten first, the present inventors determined that this phenomenon could be related to mechanical interactions between cells. As noted in FIG. 1C, the growth model predicts that the interior cells in a 4-cell microcolony experience higher relative forces compared to exterior cells.

To further demonstrate this phenomena, as shown in FIG. 2E, the present inventors grew cells on agar pads solidified with either 0.5% or 2.5% agar (instead of typical 1%) to vary the stiffness of the growth environment and alter the mechanical interactions between cells. Growth in 2.5% agar greatly sensitized the cells and resulted in increased fluorescence during cell-cell interactions. As shown in FIG. 2F, in-situ TEM images of intact microcolonies demonstrate the extent to which cell-cell and cell-substrate interactions, as well as colony position can have on cellular morphology. The differences in cellular morphology are particularly apparent when comparing cells in the interior versus edge of microcolonies; interior cells resemble polygons due to extremely close cell-cell interacts in contrast to the capsule shaped exterior cells. The dense and symmetrically arranged thylakoid membranes visible along the central axis of the microcolony are likely the result of daughter cells inheriting pre-existing templates for membrane biogenesis from the mother cell, rather than a specific consequence of microcolony formation. The lineage information is preserved in this 16-cell stage colony, revealing potential ultrastructural inheritance patterns of photosynthetic membranes that could influence cellular energy metabolism and fitness for multiple generations.

Heterogeneous distribution of electron-transparent storage granules, possibly glycogen, within the colony suggests that colony position also influences cellular metabolism and carbon partitioning. In one embodiment, glycogen accumulation may function as a major sink for photosynthetically derived electrons when growth is restricted. As shown in FIG. 2G, because of the extensive cell-cell contact observed, and to exclude the possibility that increased fluorescence could be due to cell-cell signaling or quorum sensing, the present inventors cultivated cells in the presence of fluorescent polystyrene beads with similar dimensions to cells. We found that cell-bead interactions also resulted in high-fluorescence, demonstrating the unlikelihood that this response is due exclusively to specific cell-cell signaling pathways.

Figure 18:
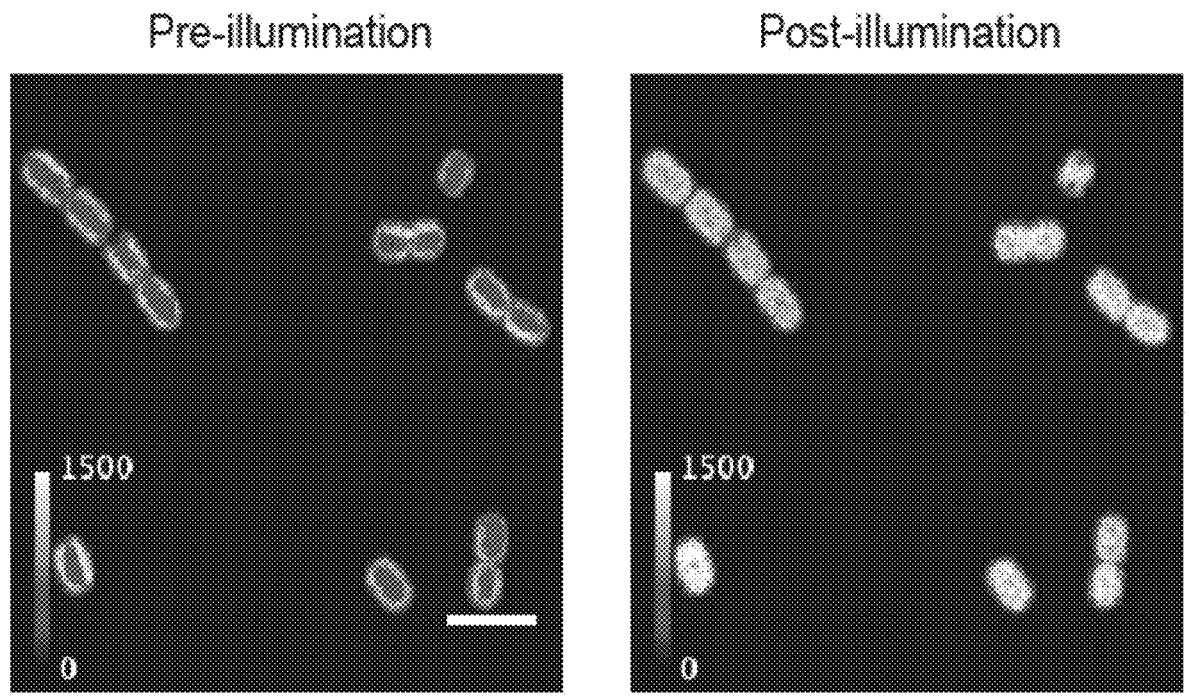
FIG. 18: Light-induced decoupling of phycobilisome at sub-cellular resolution. Cells were imaged before (left) and after (right) strong illumination with 640 nm light for 1 second.
Figure 19:
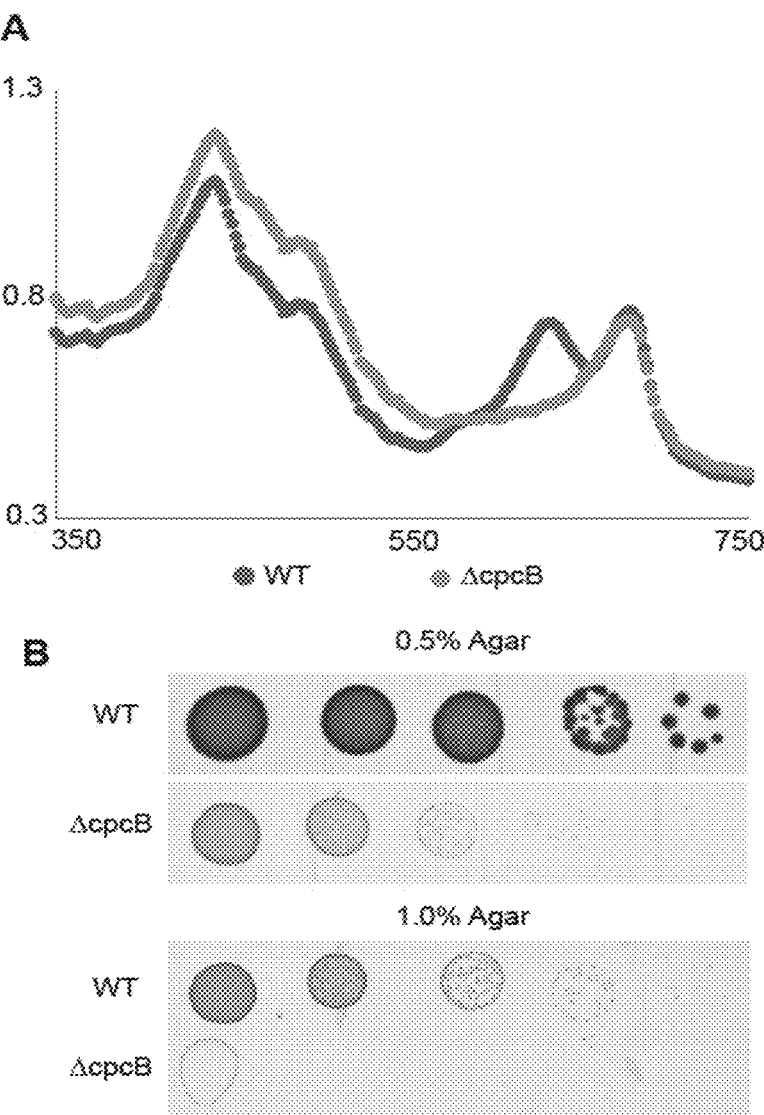
FIG. 19: Spectral analysis and growth comparison of wild-type and ΔcpcB mutants. A) Absorption of WT and ΔcpcB mutant. Y-axis (absorbance), X-axis (wavelength, nm). B) Growth of ΔcpcB is restricted on high percentage agar.
Figure 20A:
FIG. 20A-G: Demonstrates 2-second time-course images of growth of WT 7002 microcolonies. YFP (right panel), Cy5 (middle), merge (right)
Figure 20B:
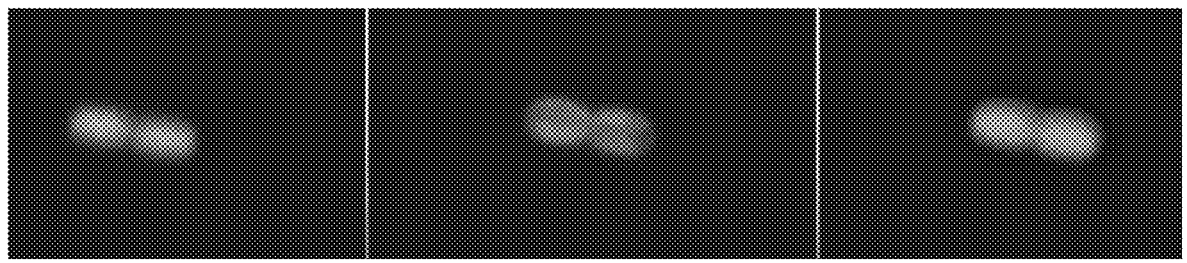
Figure 20C:
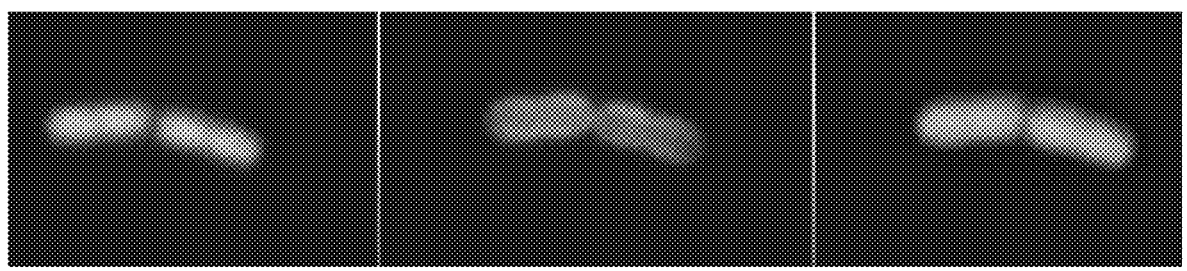
Figure 20D:
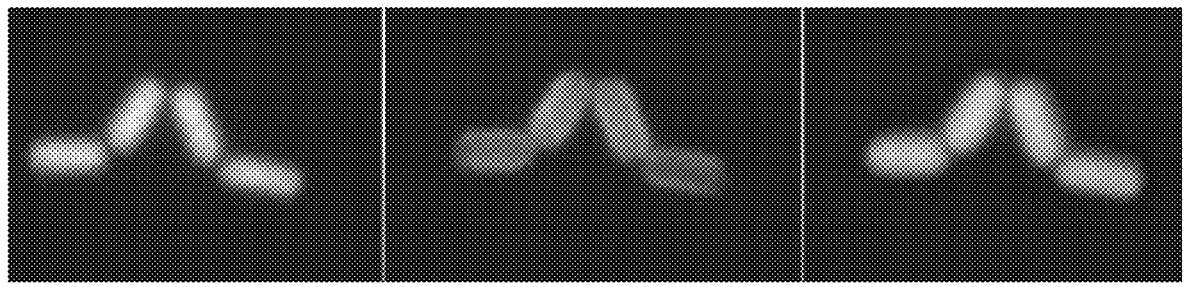
Figure 20E:
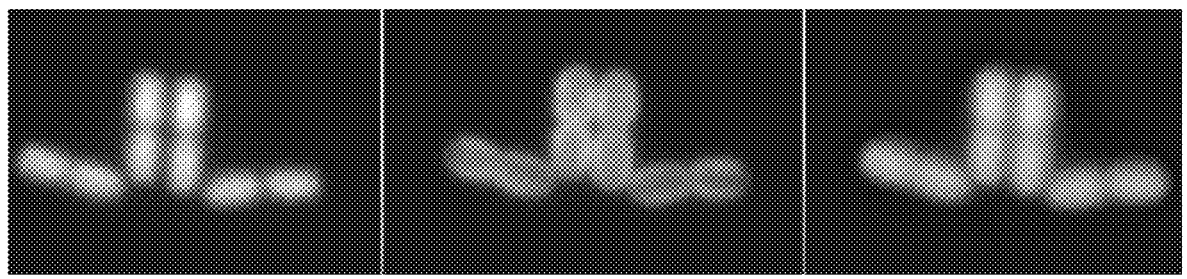
Figure 20F:
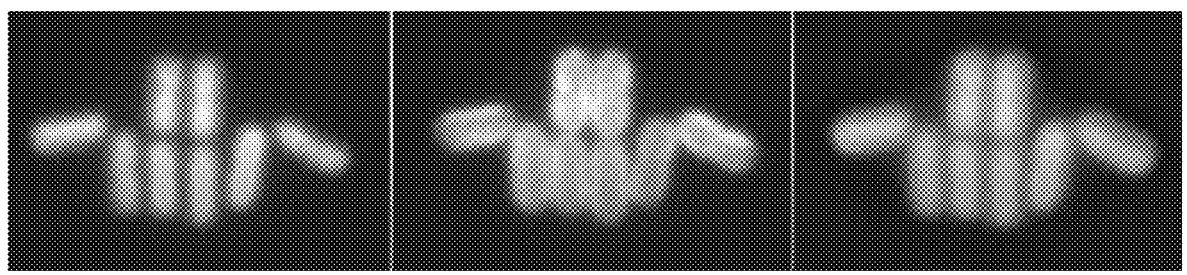
Figure 20G:
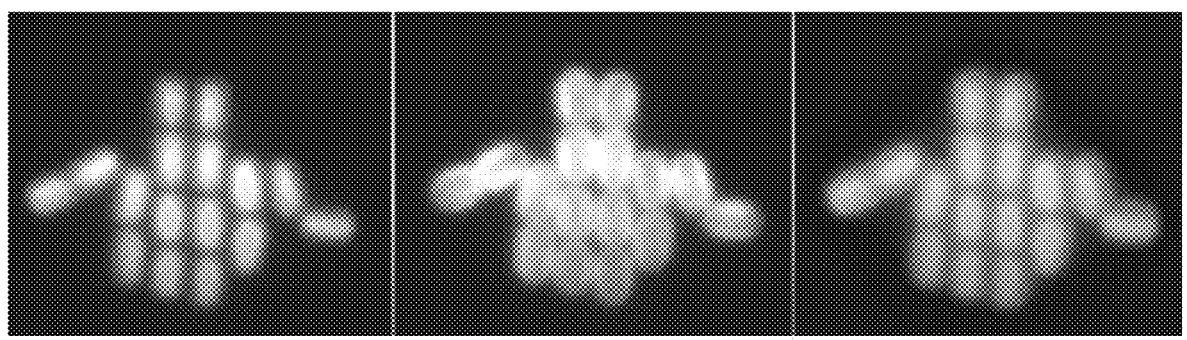
Figure 21A:
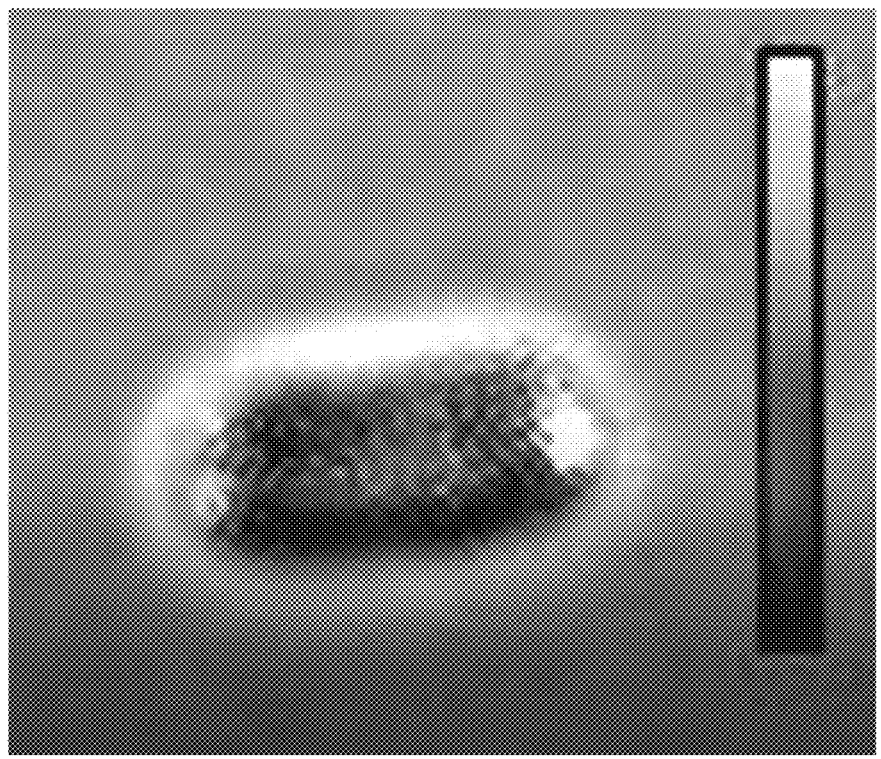
FIG. 21A-D: Demonstrates 2-second time-course images of transient flash in ΔcpcB strain.
Figure 21B:
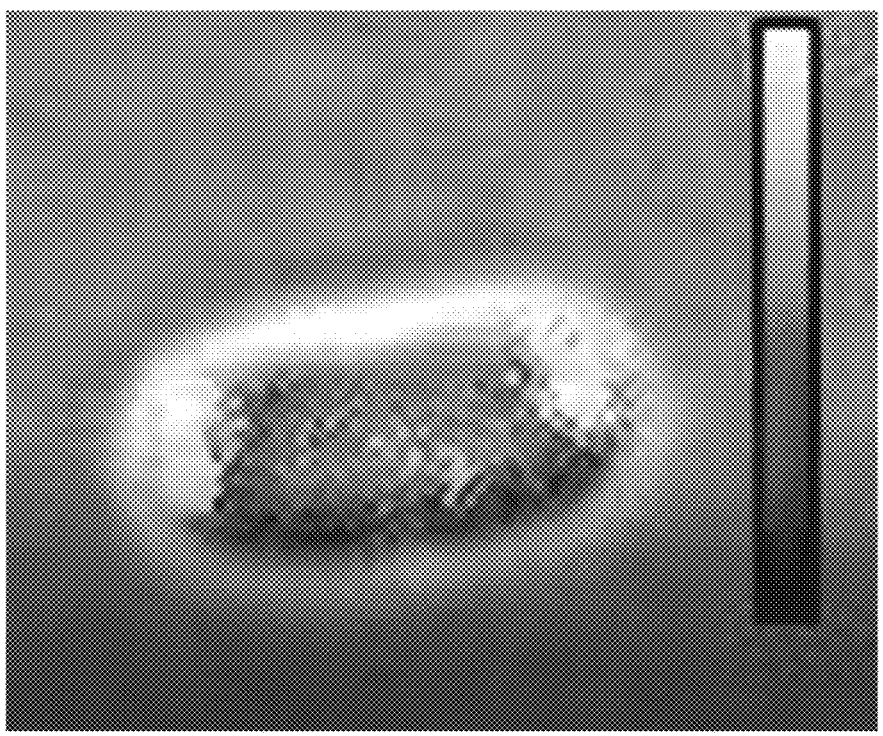
Figure 21C:
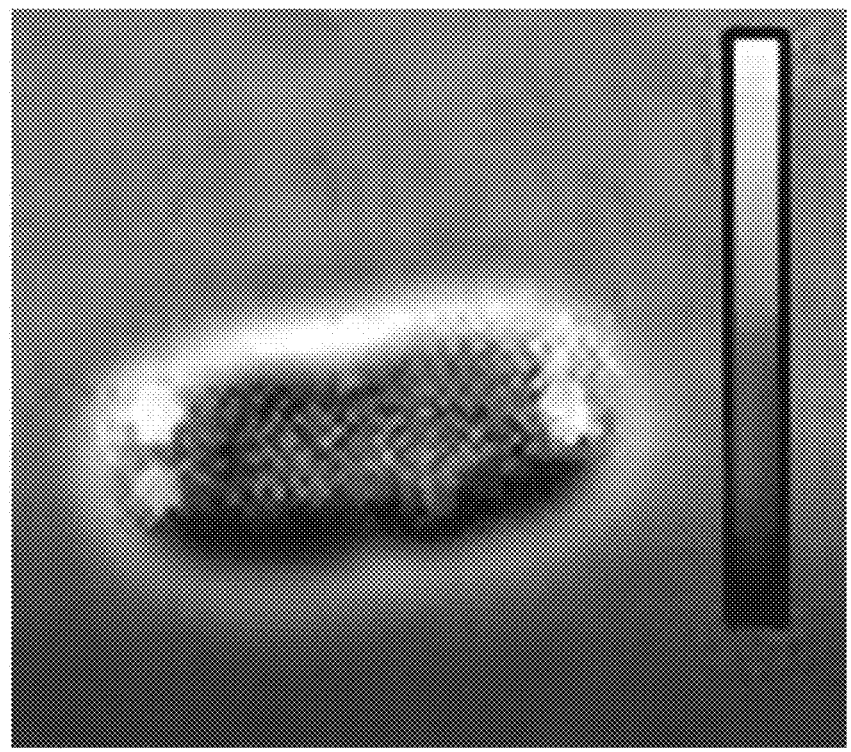
Figure 21D:
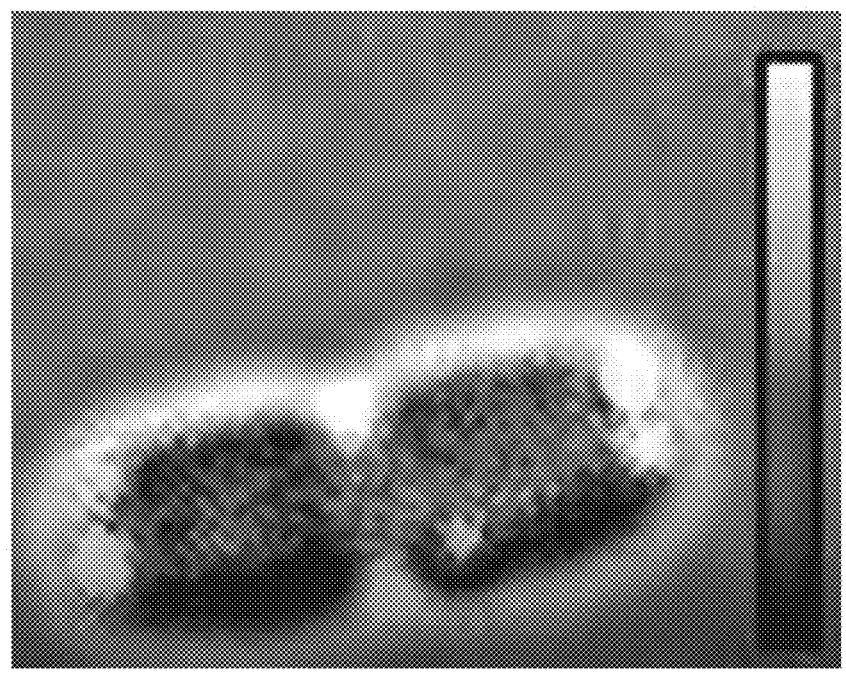
Figure 22A:
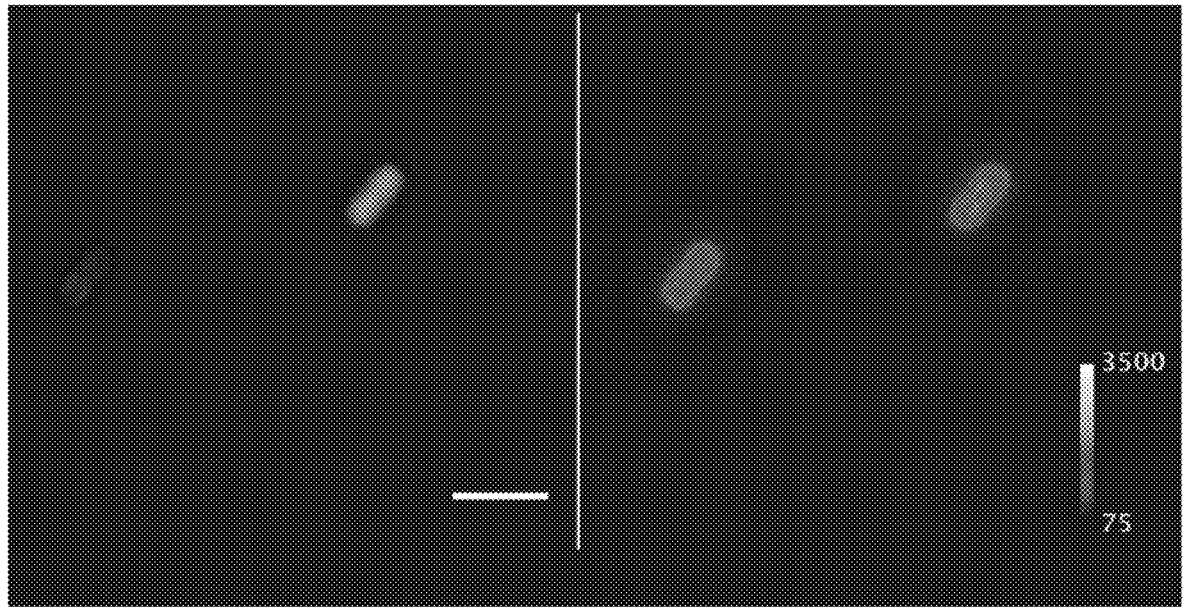
FIG. 22A-H: Demonstrates 2-second time-course images of side-by-side comparison of WT (YFP) and ΔOCP.
Figure 22B:
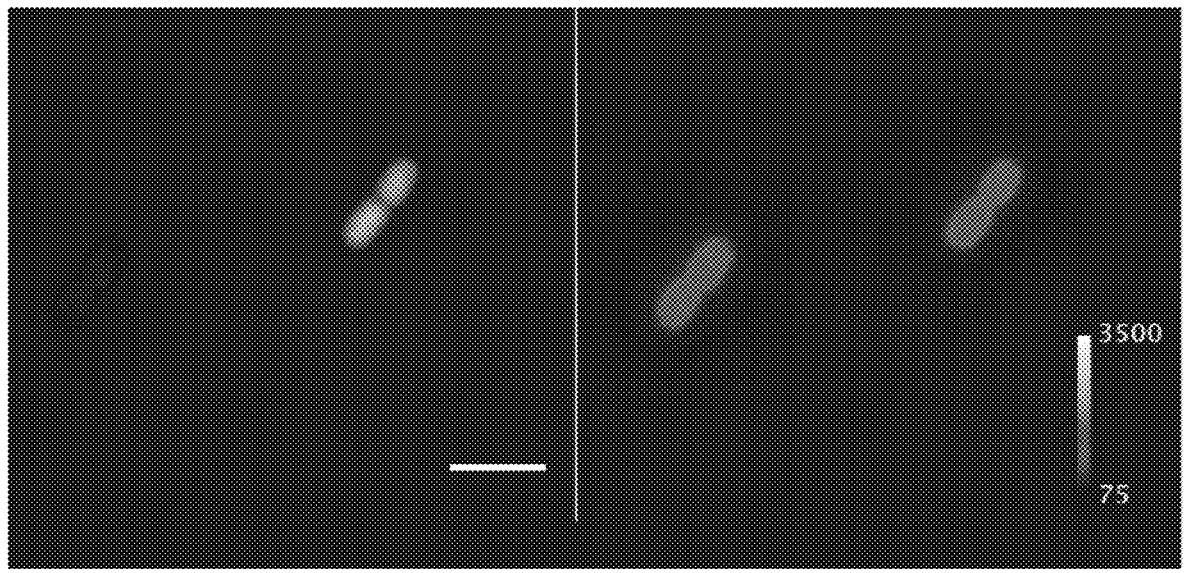
Figure 22C:
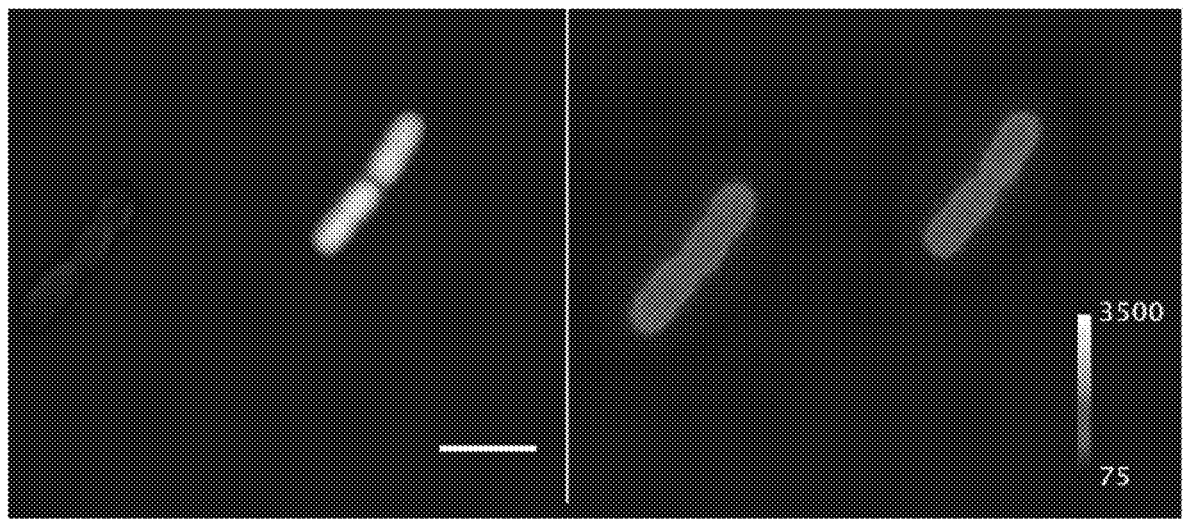
Figure 22D:
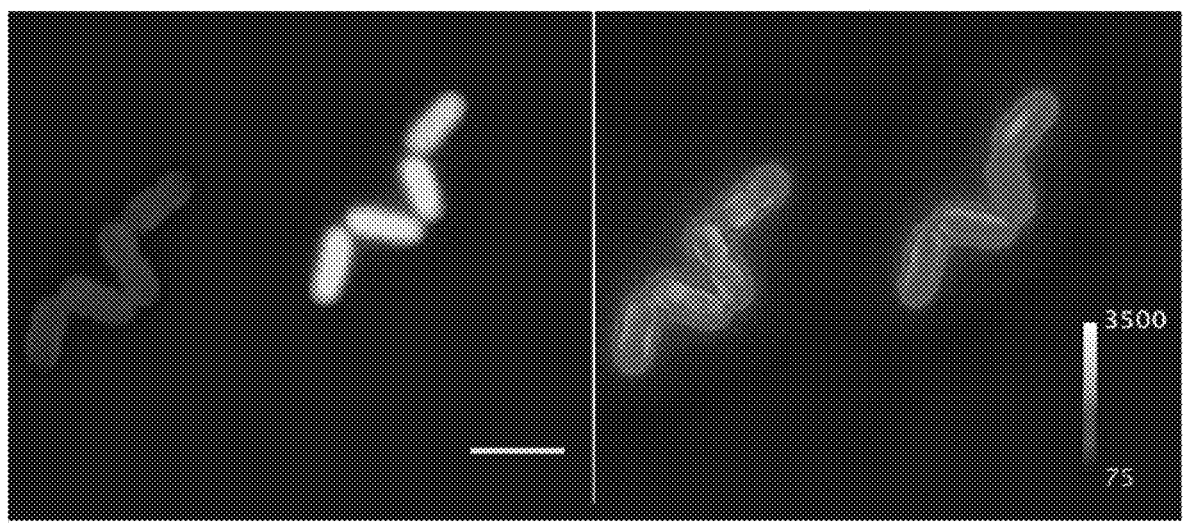
Figure 22E:
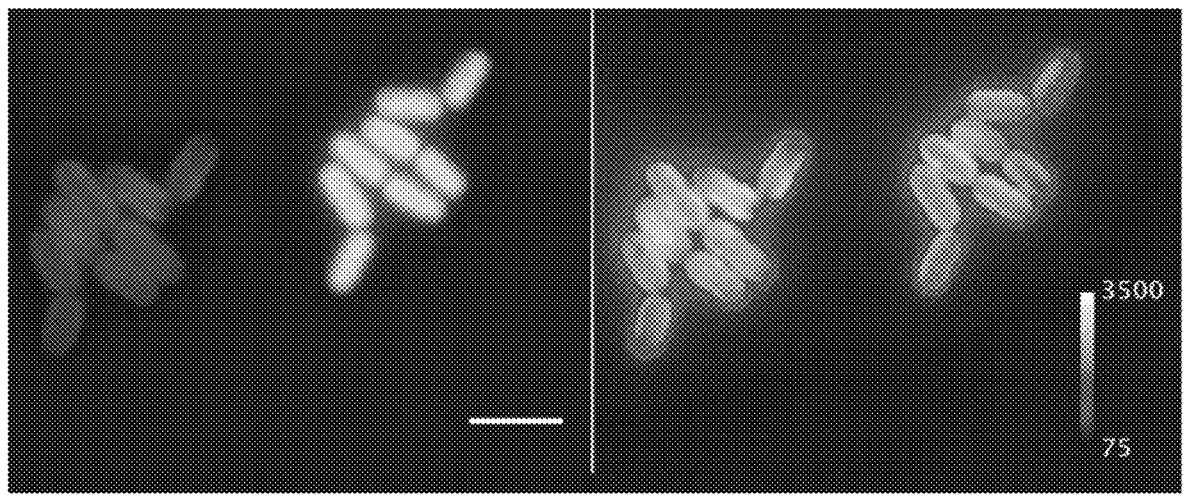
Figure 22F:
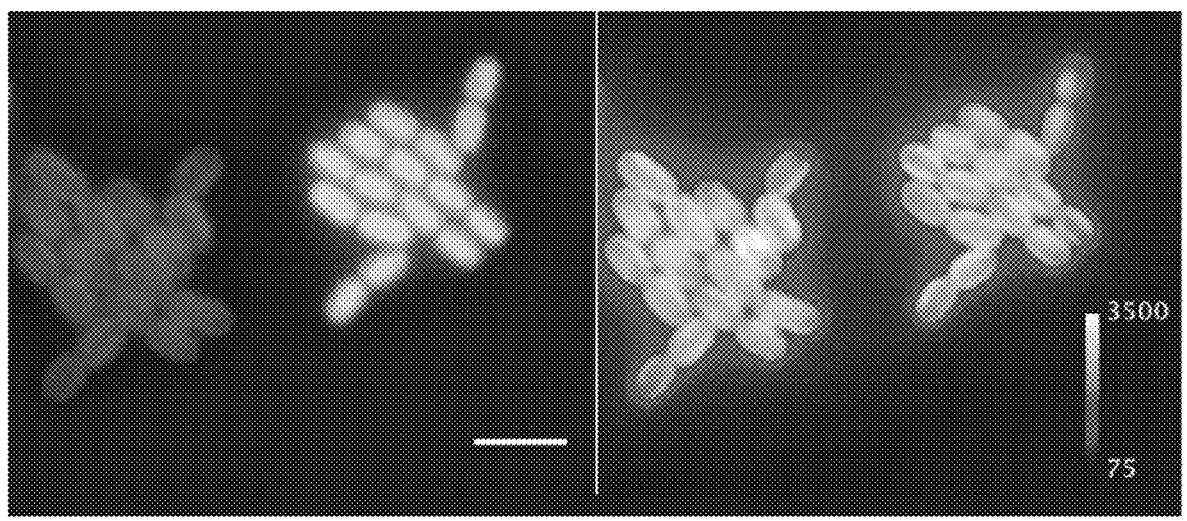
Figure 22G:
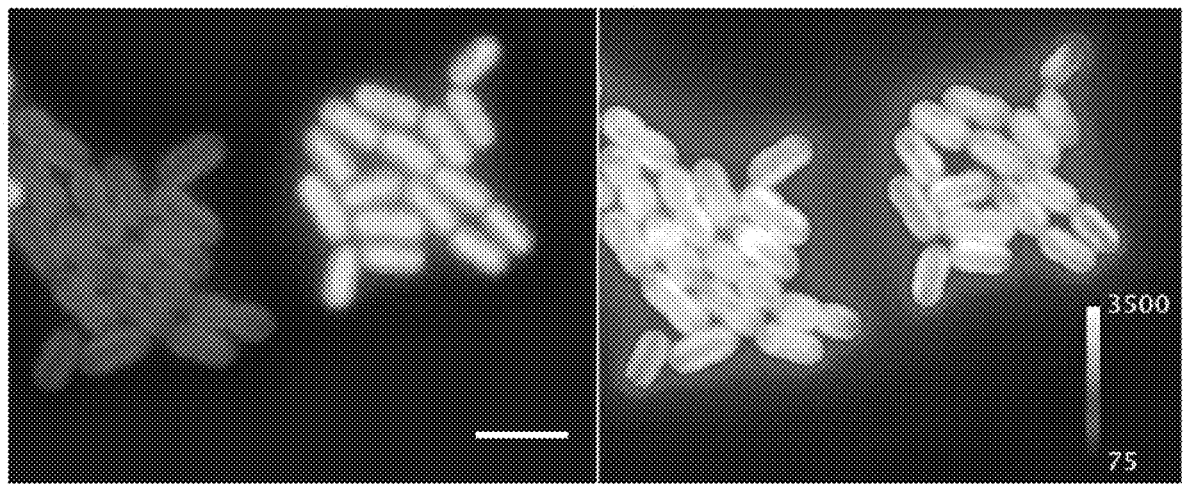
Figure 22H:
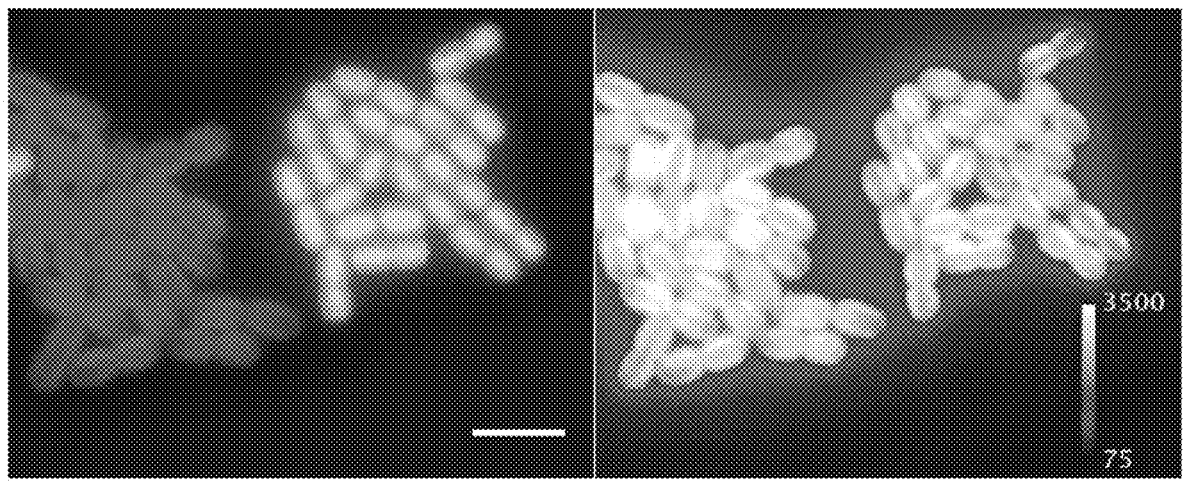
Figure 23A:
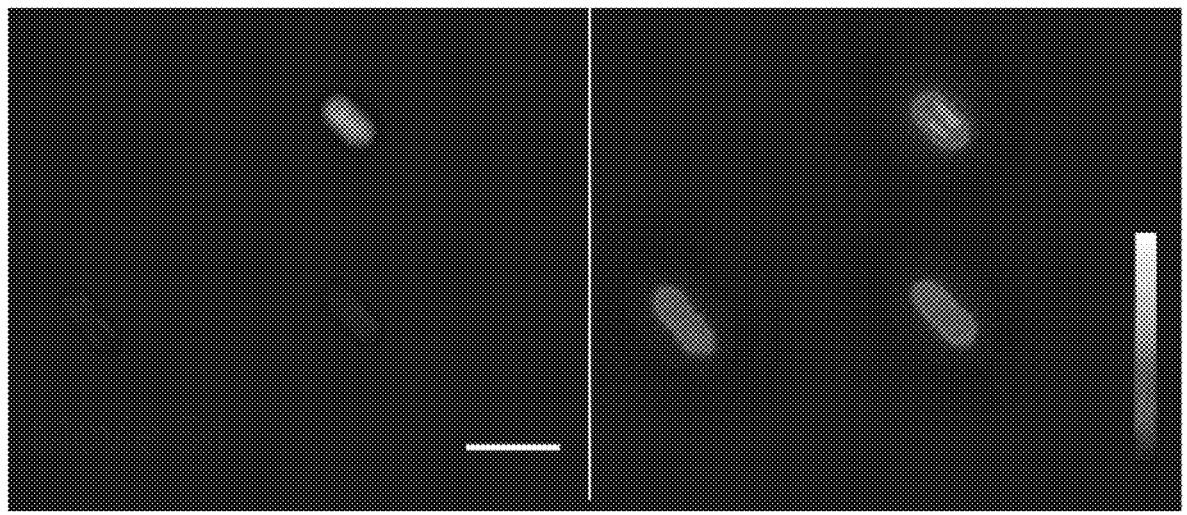
FIG. 23A-I: Demonstrates 2-second time-course images of side-by-side comparison of WT (YFP) and ΔFRP.
Figure 23B:
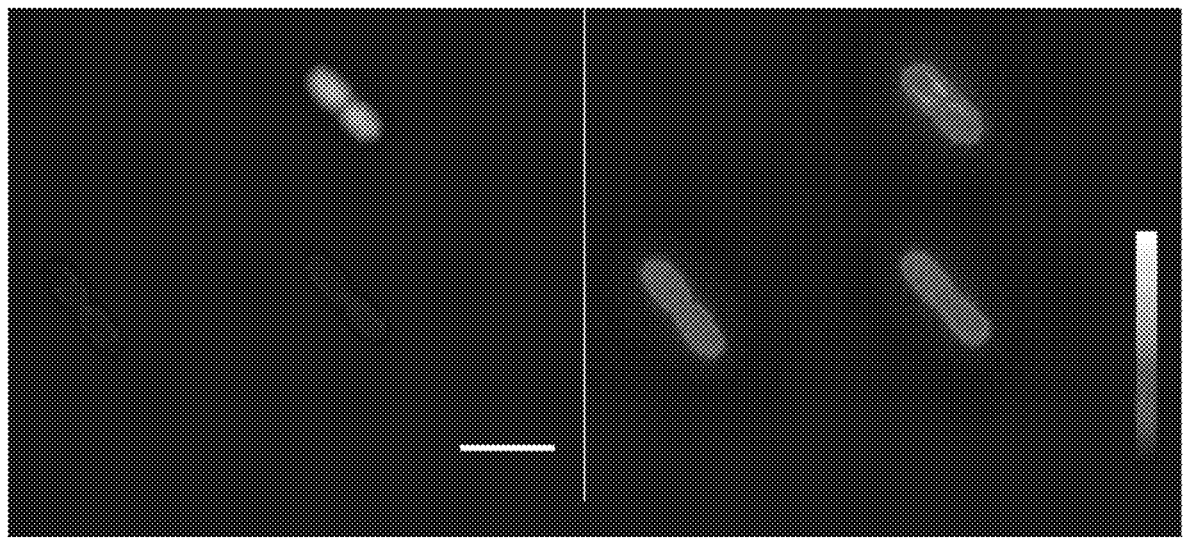
Figure 23C:
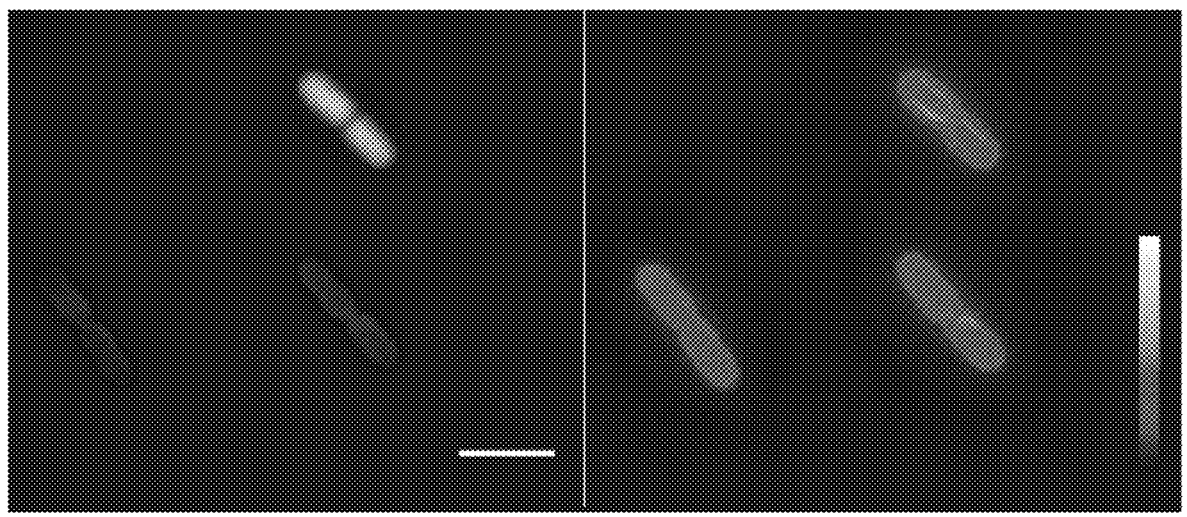
Figure 23D:
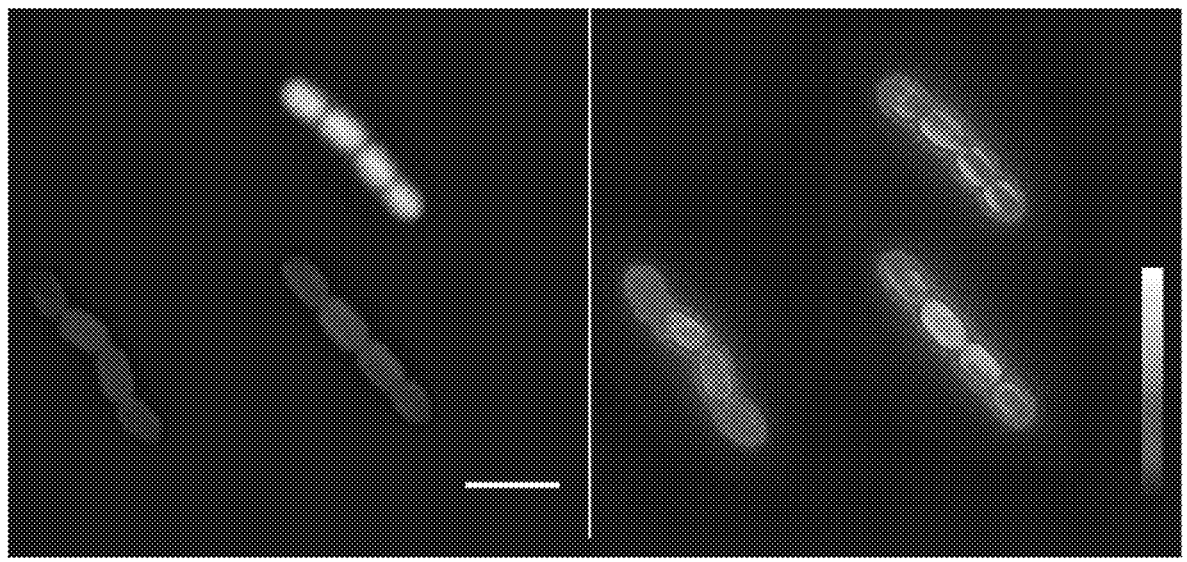
Figure 23E:
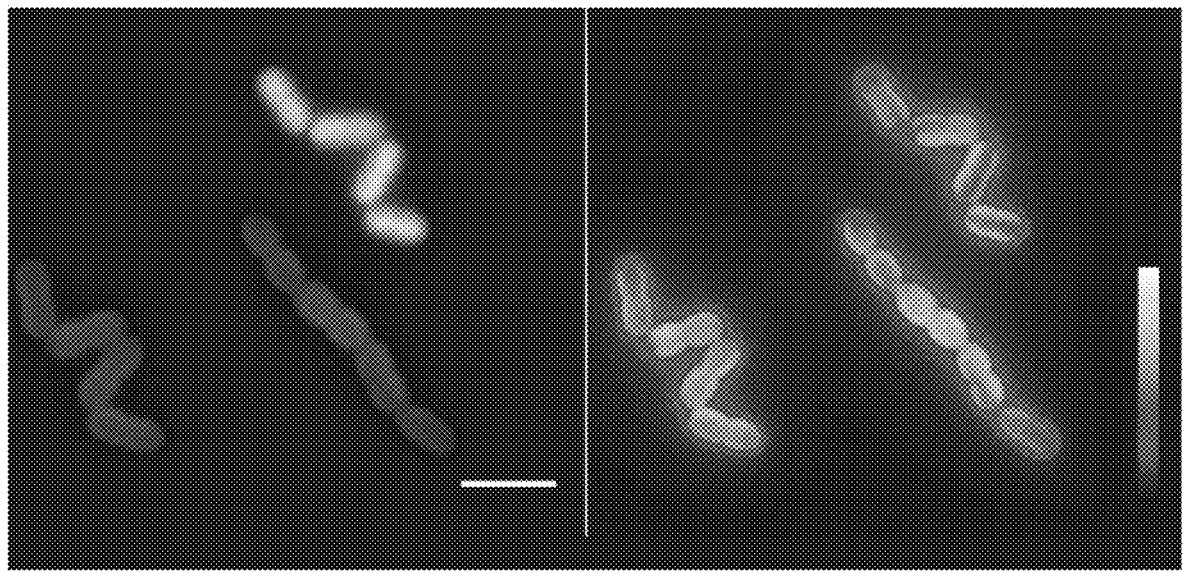
Figure 23F:
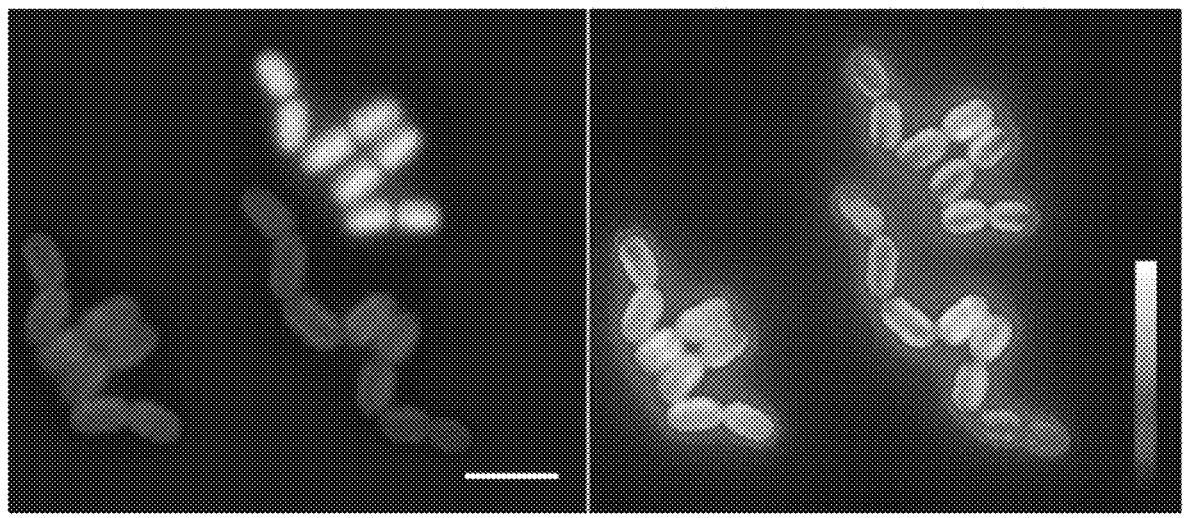
Figure 23G:
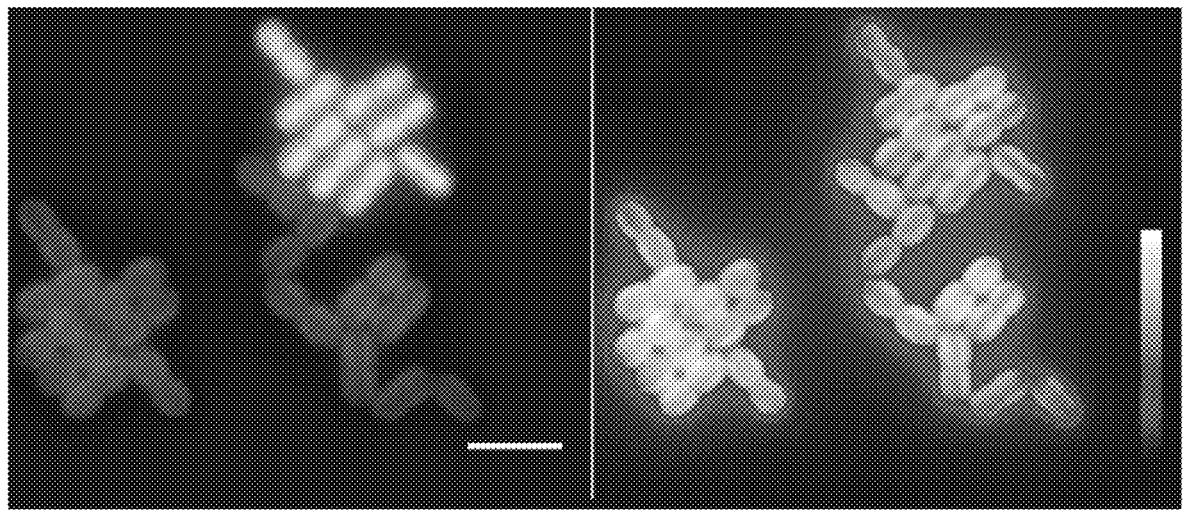
Figure 23H:
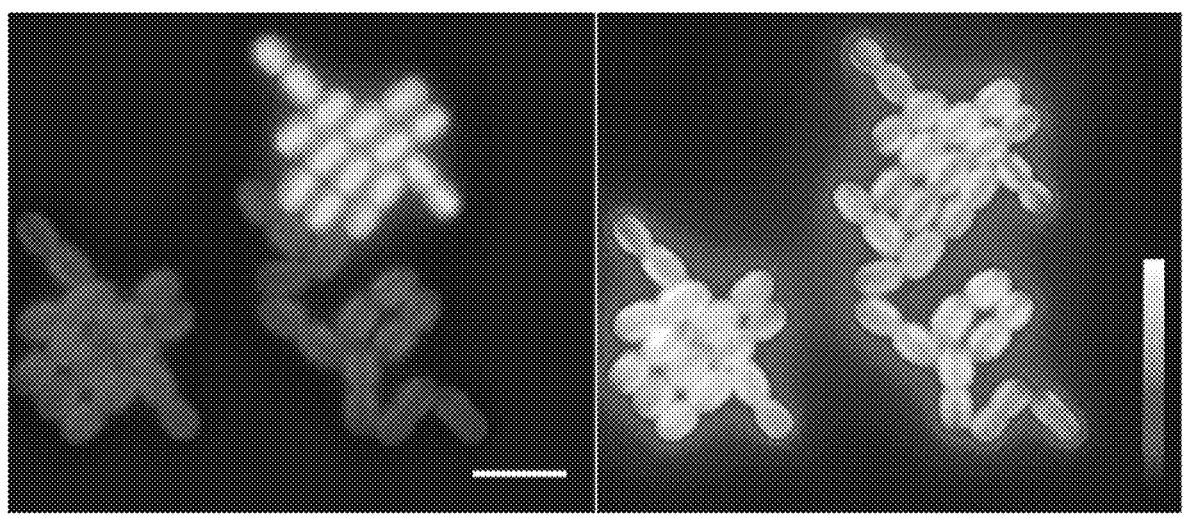
Figure 23I:
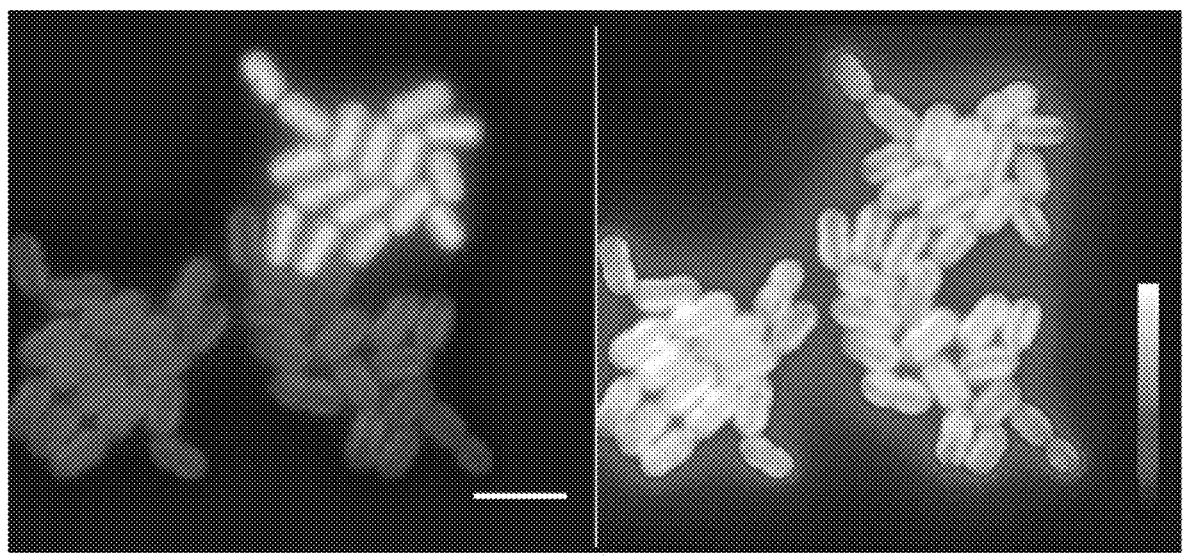
Figure 24A:
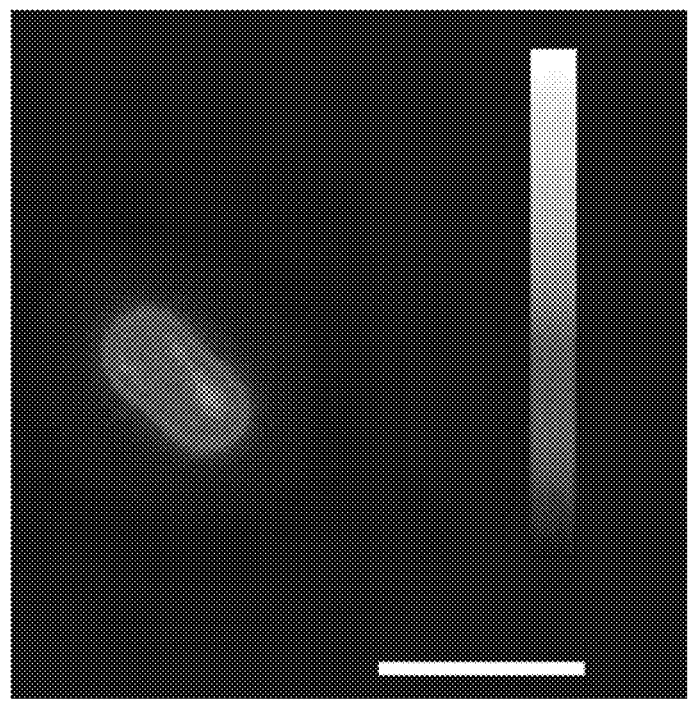
FIG. 24A-G: Demonstrates 2-second time-course images of growth of ΔmscS.
Figure 24B:
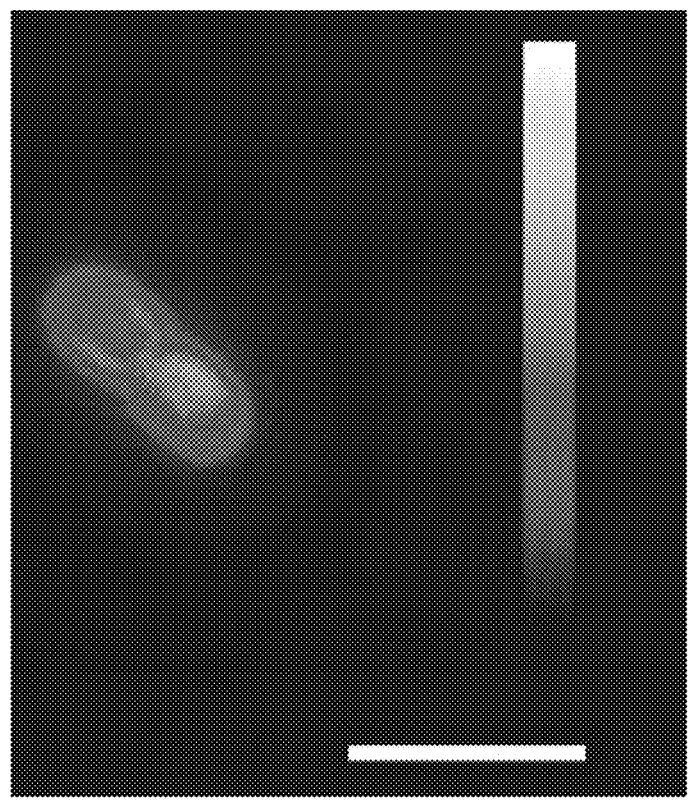
Figure 24C:
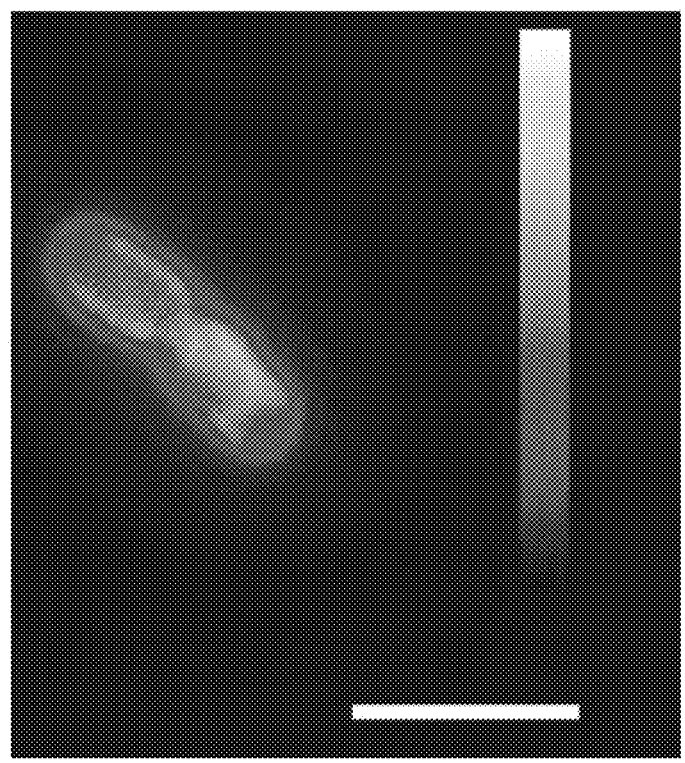
Figure 24D:
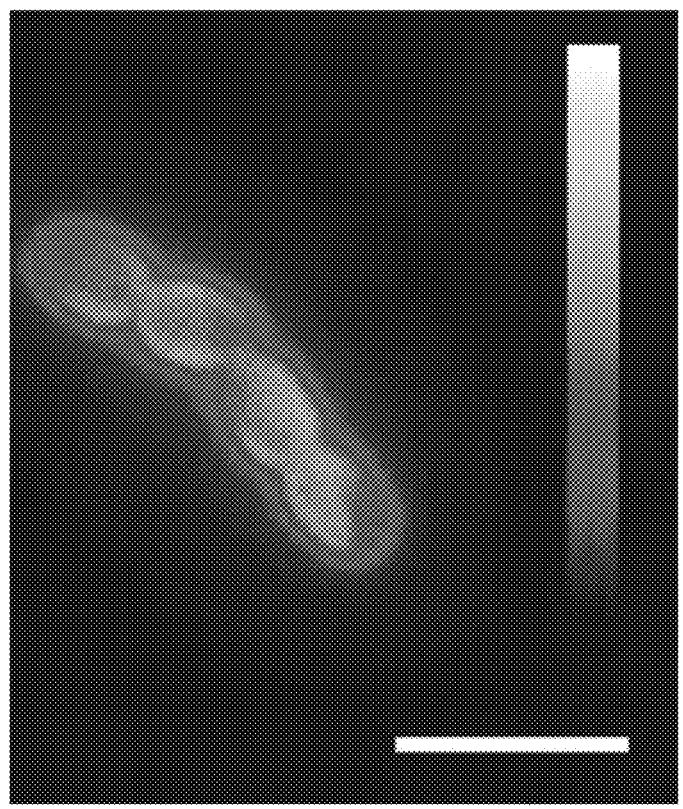
Figure 24E:
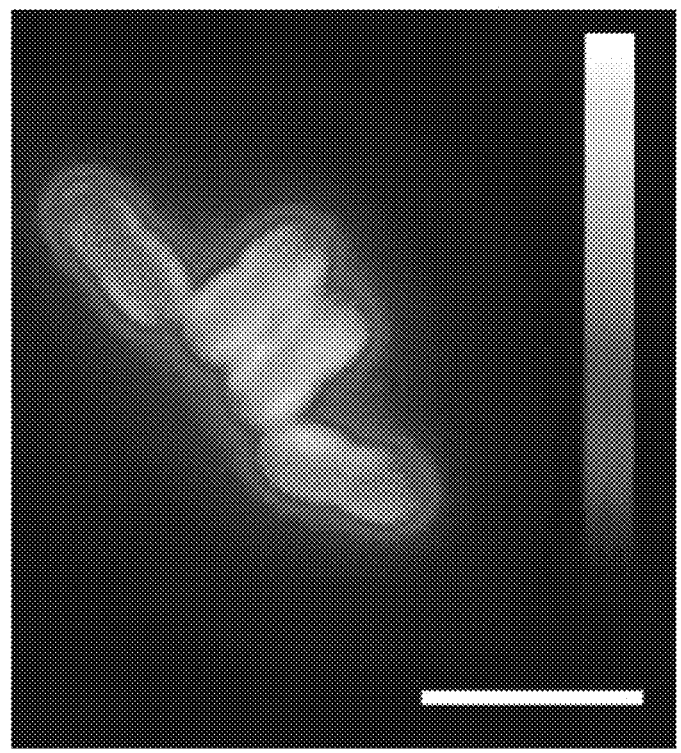
Figure 24F:
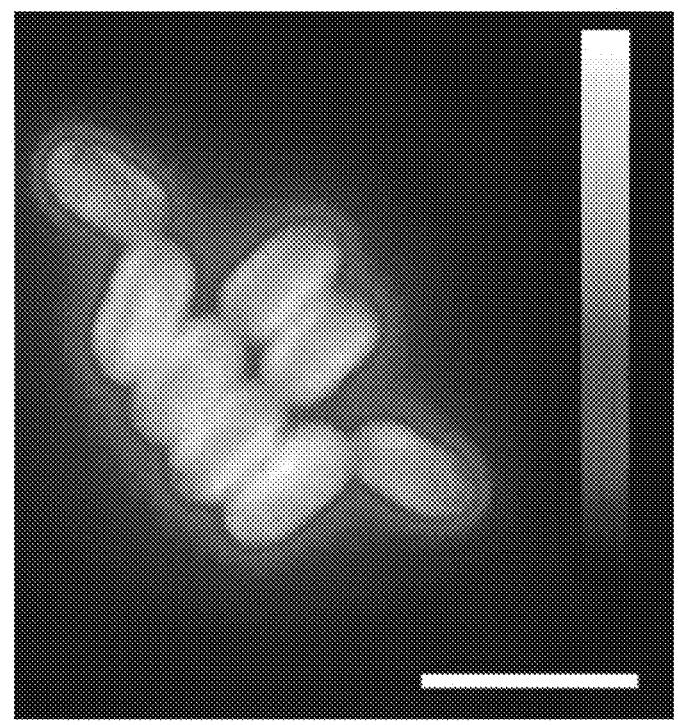
Figure 24G:
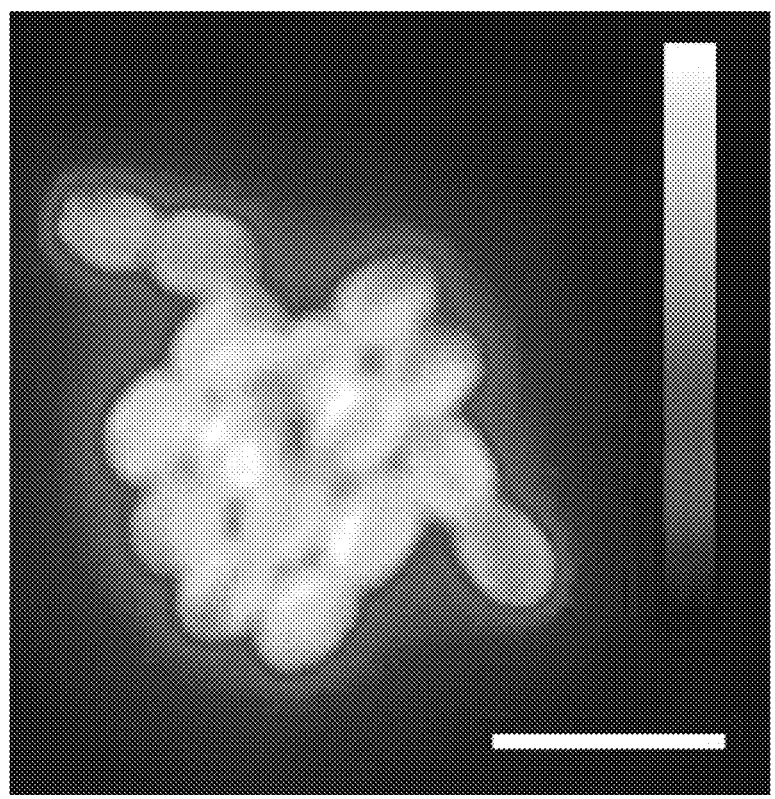
Figure 25A:
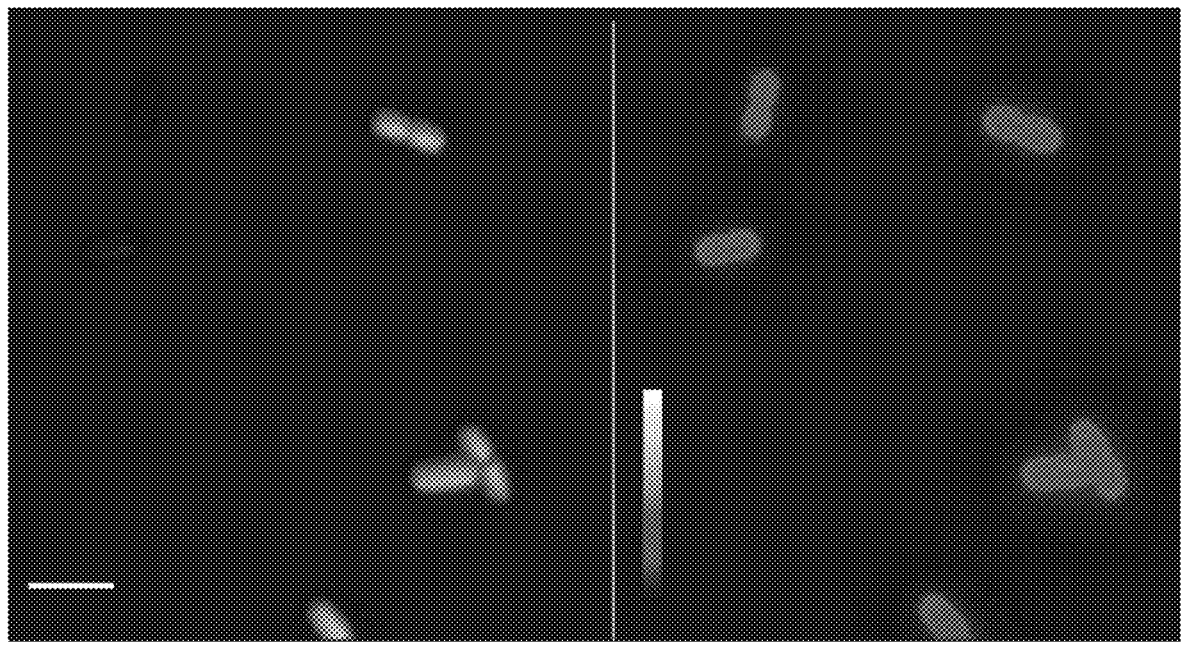
FIG. 25A-H: Demonstrates 2-second time-course images of side-by-side comparison of WT (YFP) and ΔmscL.
Figure 25B:
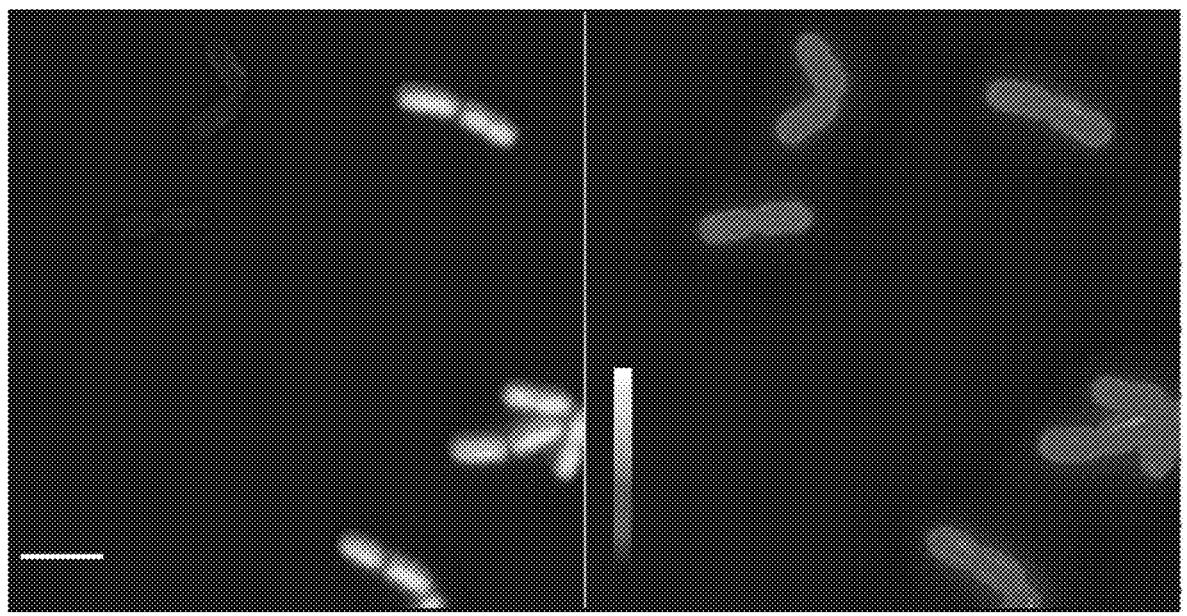
Figure 25C:
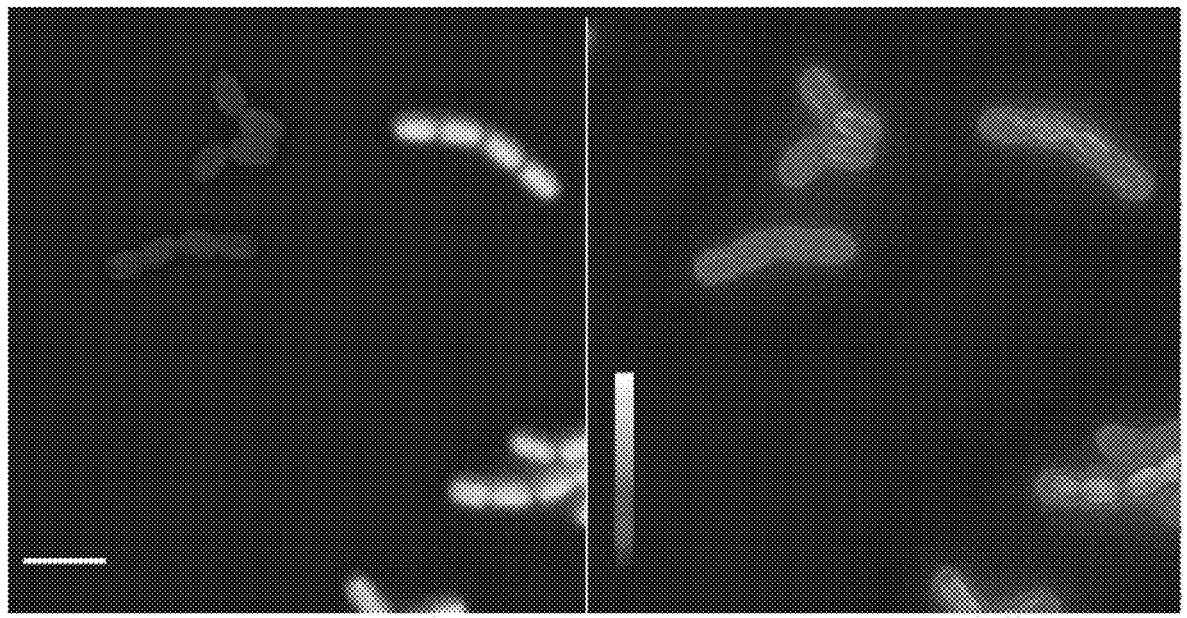
Figure 25D:
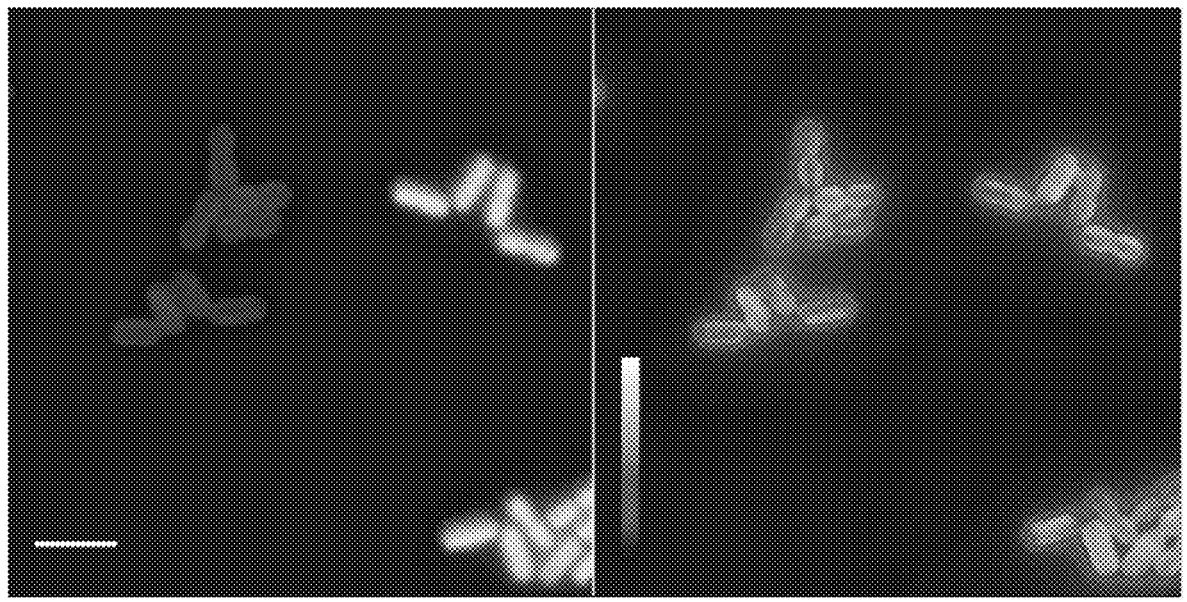
Figure 25E:
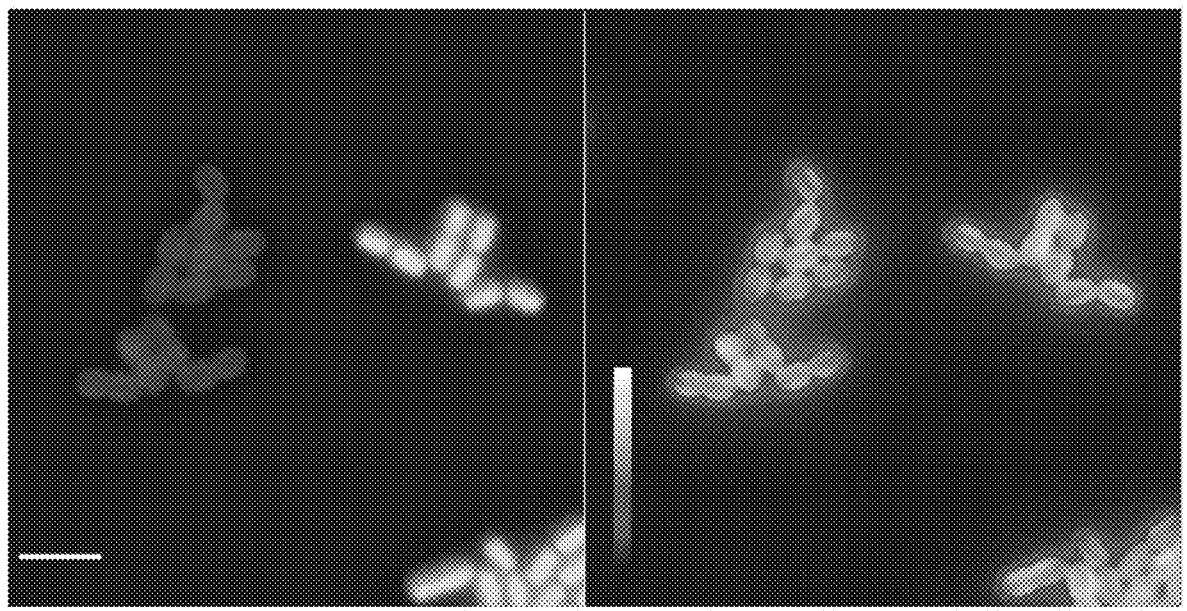
Figure 25F:
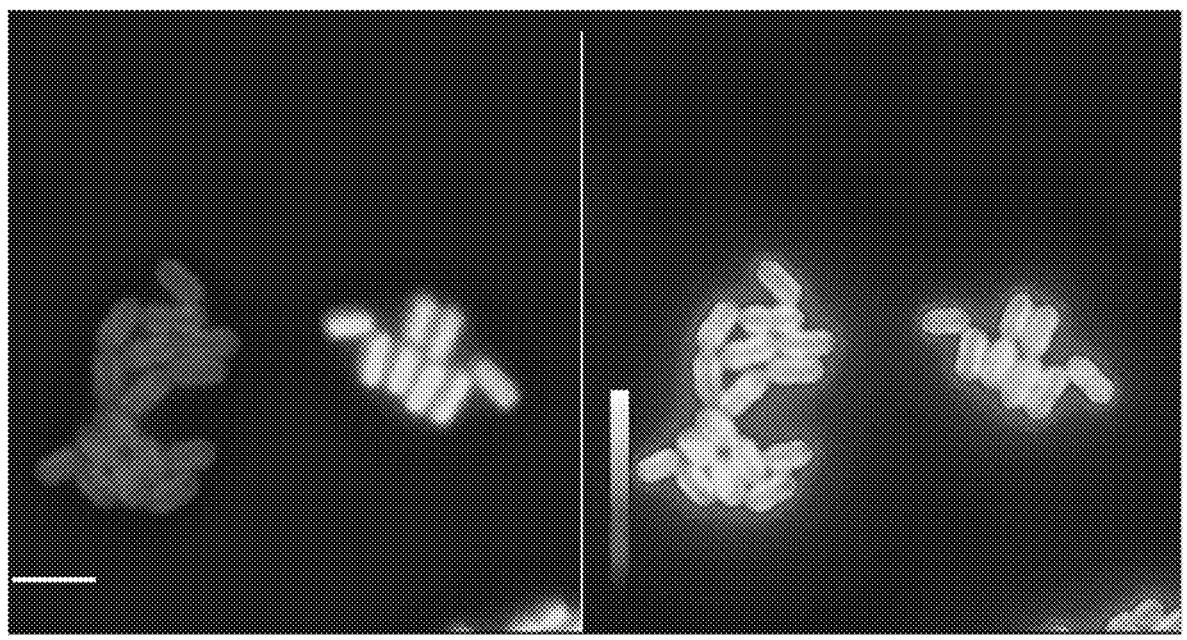
Figure 25G:
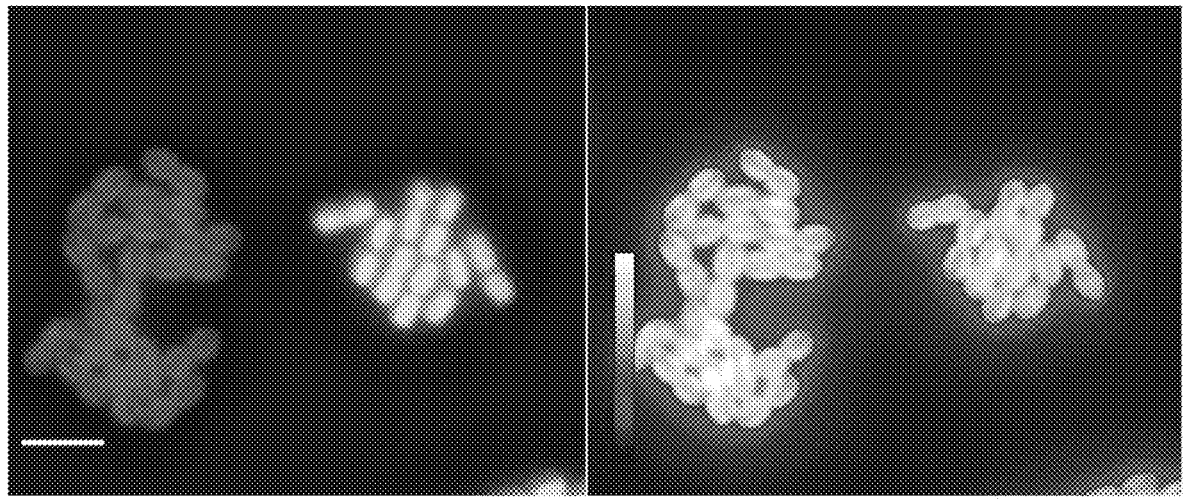
Figure 25H:
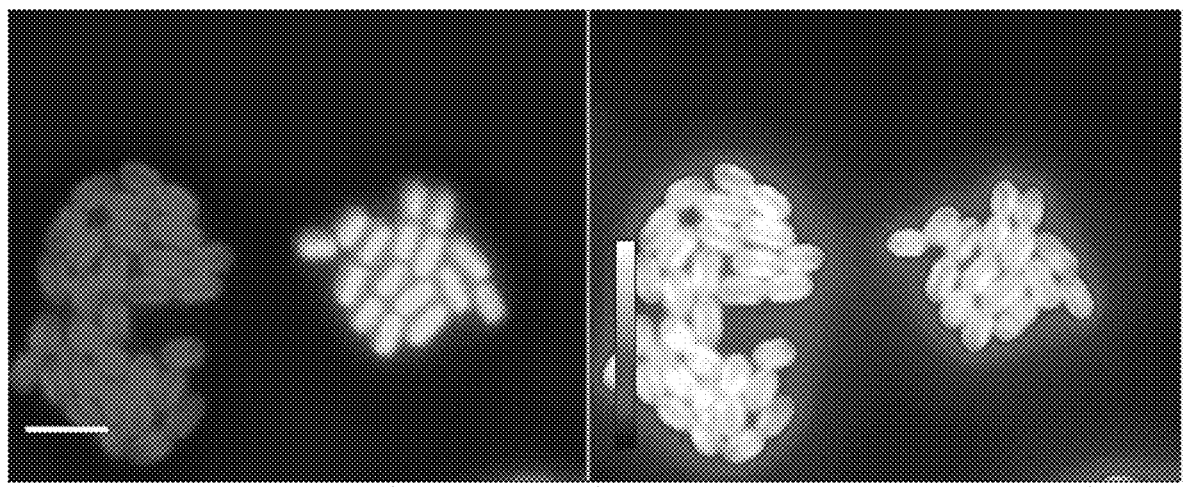
Figure 26A:
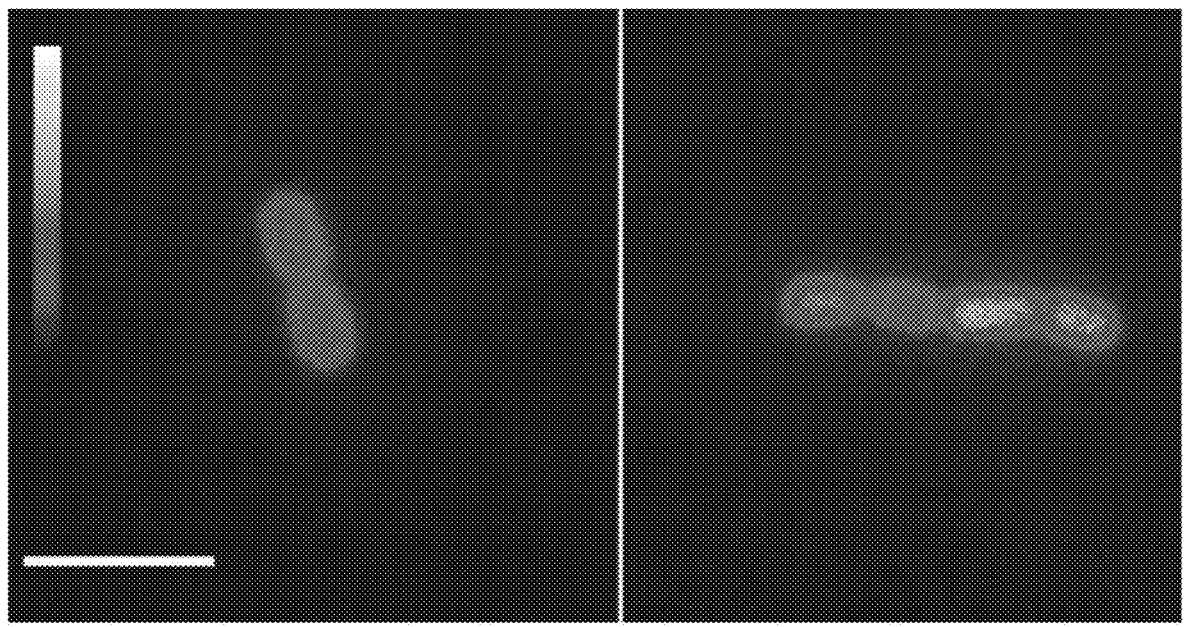
FIG. 26A-G: Demonstrates 2-second time-course images of GCaMP fluorescence in WT (left) and ΔcpcB (right) strains.
Figure 26B:
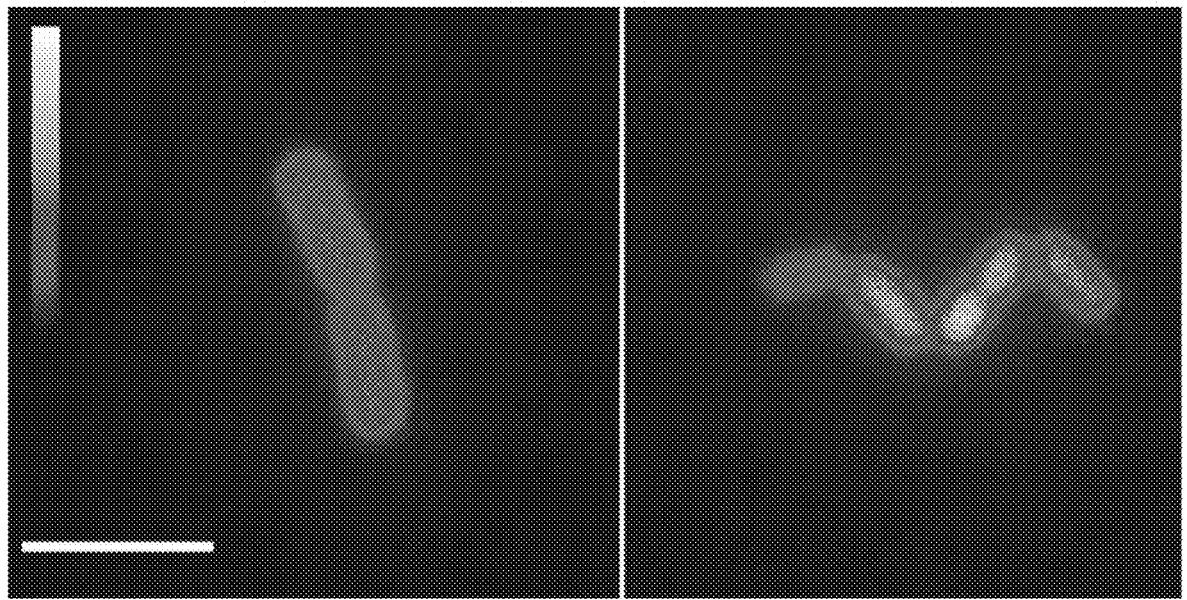
Figure 26C:
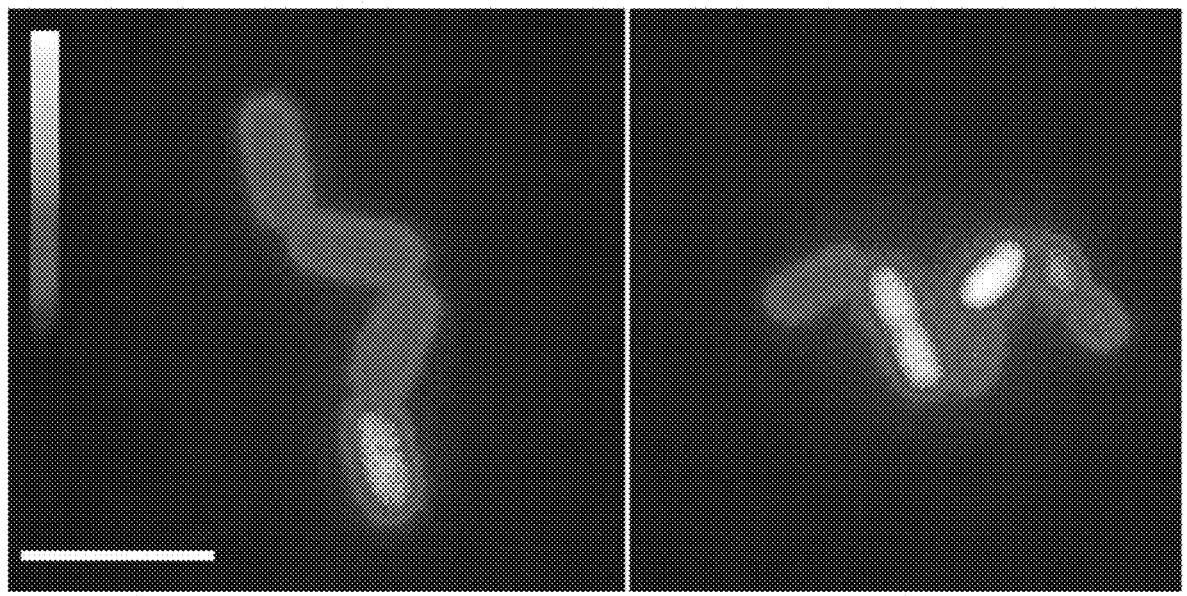
Figure 26D:
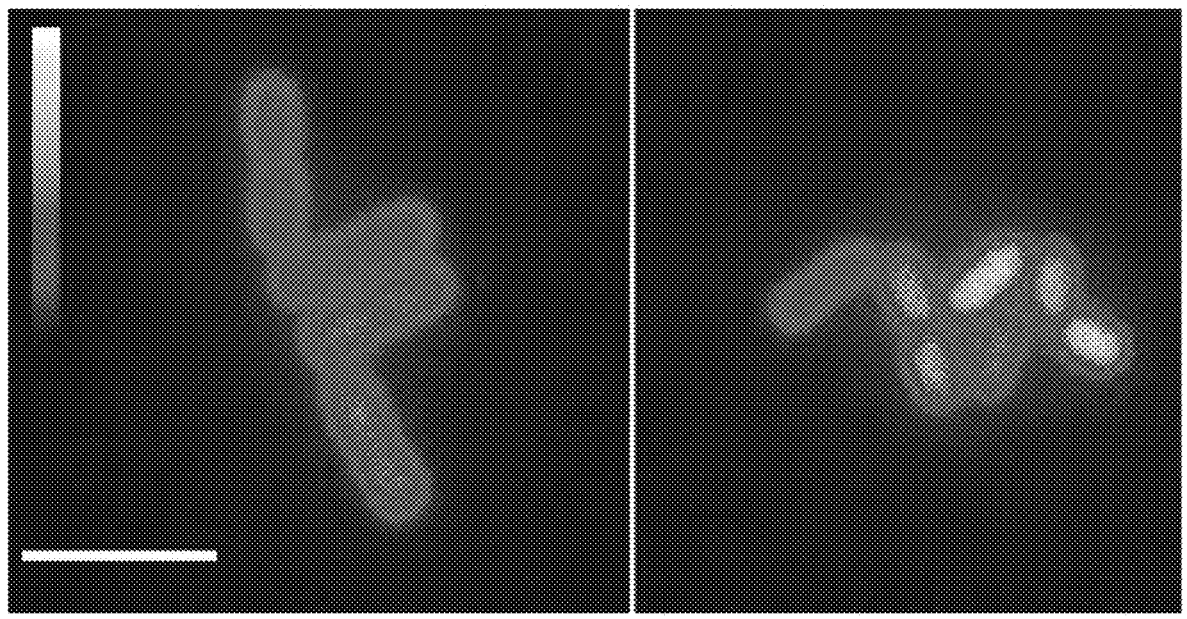
Figure 26E:
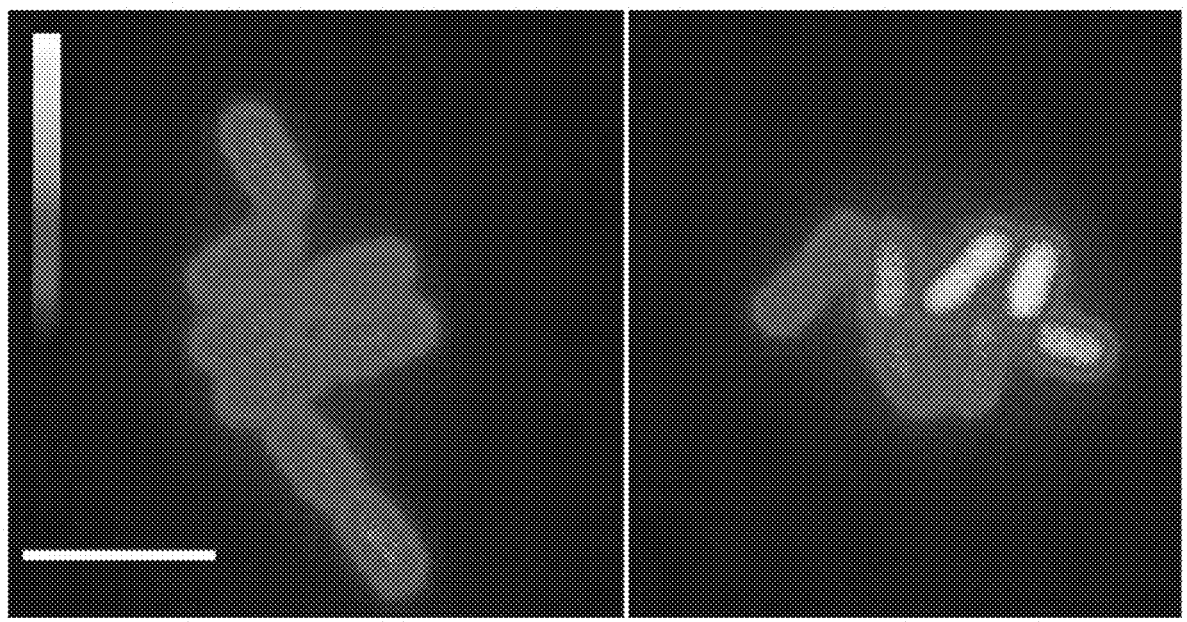
Figure 26F:
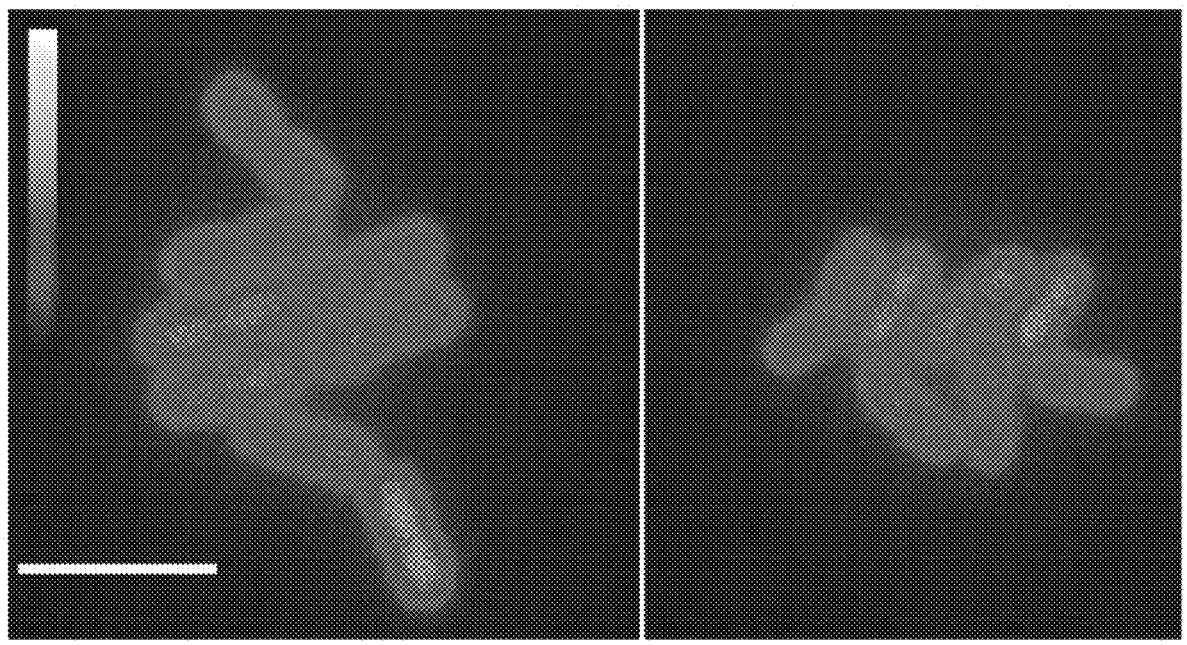
Figure 26G:
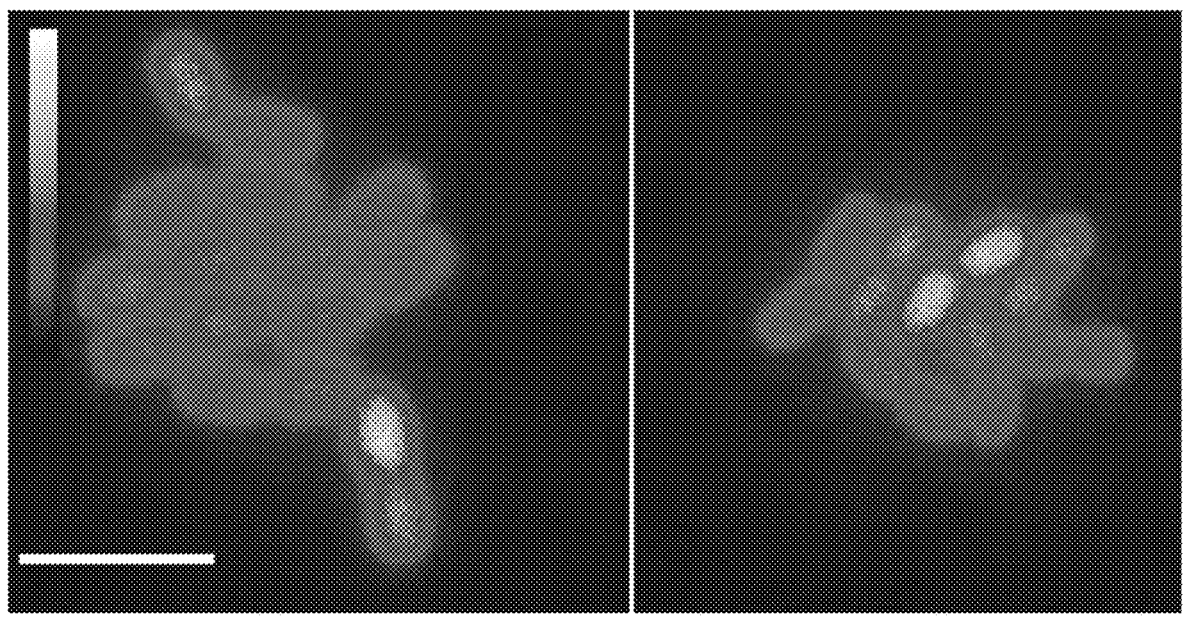

Example 4: Determination of the Molecular Origin of the Mechanically Stimulated Increase in Fluorescence in Cyanobacteria Generally referring to FIG. 18, based on the cell ultrastructure observed using fluorescence and electron microscopy, the signal appears to originate in the thylakoid membranes and then diffuse to the cell interior in a similar fashion as high-light induced phycobilisome dissociation from PSII reaction centers. Either genetic deletion or depletion of the peripheral phycobilisome rods using CRISPR-interference resulted in cells with distinct spectral features compared to the wild-type and observable change in colony color (see FIG. 19A). Moreover, these strains exhibited a severe growth defect as the stiffness of the agar is increased; in fact, fully segregated mutants could only be generated when selections were performed on 0.5% agar (see FIG. 19B).

These differential growth properties could potentially be harnessed to identify and characterize novel mutants with increased or decreased ability to transform light energy into kinetic energy. In addition to dim fluorescence compared to the wild-type, as shown in FIG. 3A, fluorescence increase upon mechanical stimulation was highly attenuated in these strains. Interestingly, removal of the phycobilisome rods greatly reduced background fluorescence in the cell and enabled observation of the subcellular location of the remaining Apc core proteins, which, as highlighted in FIG. 3B, assembled at distinct sites at the cell poles and midcell of actively dividing cells, potentially revealing sites of photosystem assembly. These foci are also observed in wild-type cells, but remain partially obscured by fluorescence emitted by abundant rods. In rare instances, transient dissociation of these foci into soluble, highly fluorescent particles was observed, suggesting that rods and cores are mobile and dynamic in response to mechanical stimuli (see FIG. 21). The relative rarity of core-dissociation versus rod-dissociation suggests that the association of the Apc core is more stable than the rod-association with the reaction center.

Example 5: Determination of Terminal Emitters Specifically Contributing to the Fluorescence Increase Upon Cell-Cell Contact A typical microscope setup for the above described growth employs a Cy5 bandpass emission filter (705/72 nm) to quantify fluorescence emission, making difficult the identification of the terminal emitters (e.g. PSII P680, Apc cores, or Cpc rods) leading to increased fluorescence upon cell-cell contact. The present inventors hypothesized that the Cpc rods were the major emitters based on the apparent stability of the cores and the visible movement of fluorescence from peripheral membranes to the cell interior that would unlikely be due to movement of membrane proteins. To overcome this limitation and identify the terminal emitters specifically contributing to the fluorescence increase upon cell-cell contact, the present inventors retrofitted the wide-field imaging station with a laser-scanning confocal module and spectral detector that enabled the collection of full emission spectra (2 nm resolution) following laser-based excitation of specific phycobilisome or reaction center pigments.

In this embodiment, cells were grown on medium solidified with 2% agar to enhance signal intensity and fluorescence emission spectra were collected every 10 minutes for ~2 hours. Single-cell segmentation and tracking was used to determine spectral signatures of individual cells upon mechanically stimulated fluorescence changes. Strikingly, as shown in FIG. 3C, in cell tracks that exhibited increased fluorescence, a transient increase in the 685 nm emission was observed immediately preceding increased emission at 650 nm, leading to increased ratio of 650:685 nm emission that is readily apparent in ratiometric images. As further shown in FIG. 3D, the rise in 685 emission indicates a blockage at the acceptor side of PSII immediately before decoupling of the phycobilisome rods and subsequent emission at 650 nm. A role for the PB quenching proteins, Orange Carotenoid Protein (OCP) and Fluorescence Recovery Protein (FRP), in the observed changes in fluorescence is unlikely because mutants lacking either of these proteins were indistinguishable from the wild-type under typical growth conditions (see FIGS. 22 and 23).

Moreover, strains lacking the mechanosensitive ion channels, MscS and MscL, that could play a role in this process by transducing mechanical information to the cell were not significantly different than wild-type (see FIGS. 24 and 25). However, the cells of the ΔmscL strain did appear more rigid and cells appeared to push out of the 2-D monolayer, resulting in 3-D colonies much earlier than the wild-type. While ΔmscL and ΔmscS cells still exhibited similar responses to the wild-type, the present inventors determined that an underlying ion transport could still be involved in this process based on recent observations that mechanical stimulations can induce calcium transients in E. coli in addition to the known role for calcium in regulation of photosynthesis.

As such, the present inventors introduced a constitutively expressed, genetically encoded fluorescent calcium sensor (GCaMP6) into the genome of wild-type and mutant strains of PCC 7002. Visualization of wild-type and Δcpc expressing GCaMP6 using quantitative long-term time-lapse fluorescence microscopy revealed distinct calcium transients (see FIG. 26). The frequency and number of transients observed in the Δcpc strain was higher compared to wild-type, however, the ability to characterize the complex calcium dynamics across time-series was limited by the sampling frequency (10 min), which was optimal for cell growth because "over-imaging" of photosynthetic cells, especially using short-wavelength excitation, can have major impacts on cellular physiology. These observations suggests underlying genetics can play major roles in colony morphology and cell-cell interactions in cyanobacteria and that complex underlying signaling pathways, potentially involving calcium, could play a role in governing this complex process, potentially by modulating reaction center-antennae interactions.

Example 6: Nutrient Availability Affects Cellular Processes Including Photosynthesis, Growth, and Fitness in Cyanobacteria Although it is unlikely that cells are nutrient limited at the microcolony stage based on the exponential growth rate and large nutrient reservoir in the agar pad compared to the total cellular volumes, the present inventors wanted to specifically test whether this was contributing to the observed positional dependence of cellular physiology within microcolony. For example, $CO_2$ limitation in the colony interior could potentially contribute to altered growth dynamics and fluorescence. Thus, as shown in FIG. 4A, the present inventors utilized a microfluidic device to grow cells on the surface of a gas-permeable membrane and continuous flow of nutrients under typical light regimes. The microfluidic device contains multiple connected chambers with different heights. To load cells, the chamber is pressurized to expand the chamber and then cells are trapped as the pressure is released and the chamber height decreases. This configuration enabled the present inventors to quantify growth rates of sister cells that differed only in their mechanical confinement. As shown in FIG. 4B, confined mother cells exhibited high fluorescence and slow growth, while daughter cells born into the adjacent chamber exhibited a concomitant decrease in fluorescence intensity and near doubling of growth rate.

Next, as demonstrated in FIG. 4C, the present inventors compared single-cell growth rates on a solid substrate with the summed fluorescence intensity across multiple independent colonies and found an inverse relationship between growth and fluorescence. Moreover, highly fluorescent cells also correlate to cellular positions in the microcolony predicted to be under the highest mechanical stress based on simulation data from mechanical models of bacterial growth.

The present inventors found that mechanical constraints imposed by neighboring cells and the physical environment elicit dramatic effects on cellular growth and physiology. As diagrammed in FIG. 4D, these results suggest that mechanical confinement alters the source:sink ratio by preventing the efficient formation of new biomass. The cells respond to this altered state by decoupling the antennae to prevent overexcitation of the reaction centers when sink-strength is altered.

In contrast to nutrient limitations, which also elicits down-regulation of photosynthesis, mechanical regulation of photosynthesis can occur when nutrients are plentiful and thus requires an override program to rapidly shut down light harvesting and attenuate growth in confined environments to prevent accumulation of ROS and cell lysis. In contrast to heterotrophic organisms which can regulate the transport and utilization of growth substrates, when photosynthetic organisms are exposed to light, the pigment-protein complexes inherently absorb photons, necessitating ways to rapidly dissipate the excess energy. The fact that mutants (including Δcpc) differ in their ability to grow on based on the stiffness of solid substrates indicates defects in conversion of electromagnetic radiation (light) into kinetic (mechanical) energy and indicates an important role of the light harvesting complex in translation of mechanical forces through metabolism.

These results demonstrate the importance of colony birth position and reveal that mechanical-based gradients are rapidly formed during the first two cell divisions, even within colonies of unicellular bacteria. Mechanical processes play important roles in cellular differentiation, development, and disease in multicellular organisms. Embodiments of the current invention demonstrate that the principles of mechanical-based regulation and patterning were already established in ancient microbes and that these processes play critical roles in navigating the physical environment.

Example 7: Long-Term, Quantitative Time-Lapse Imaging of PCC 7002

Figure 6:
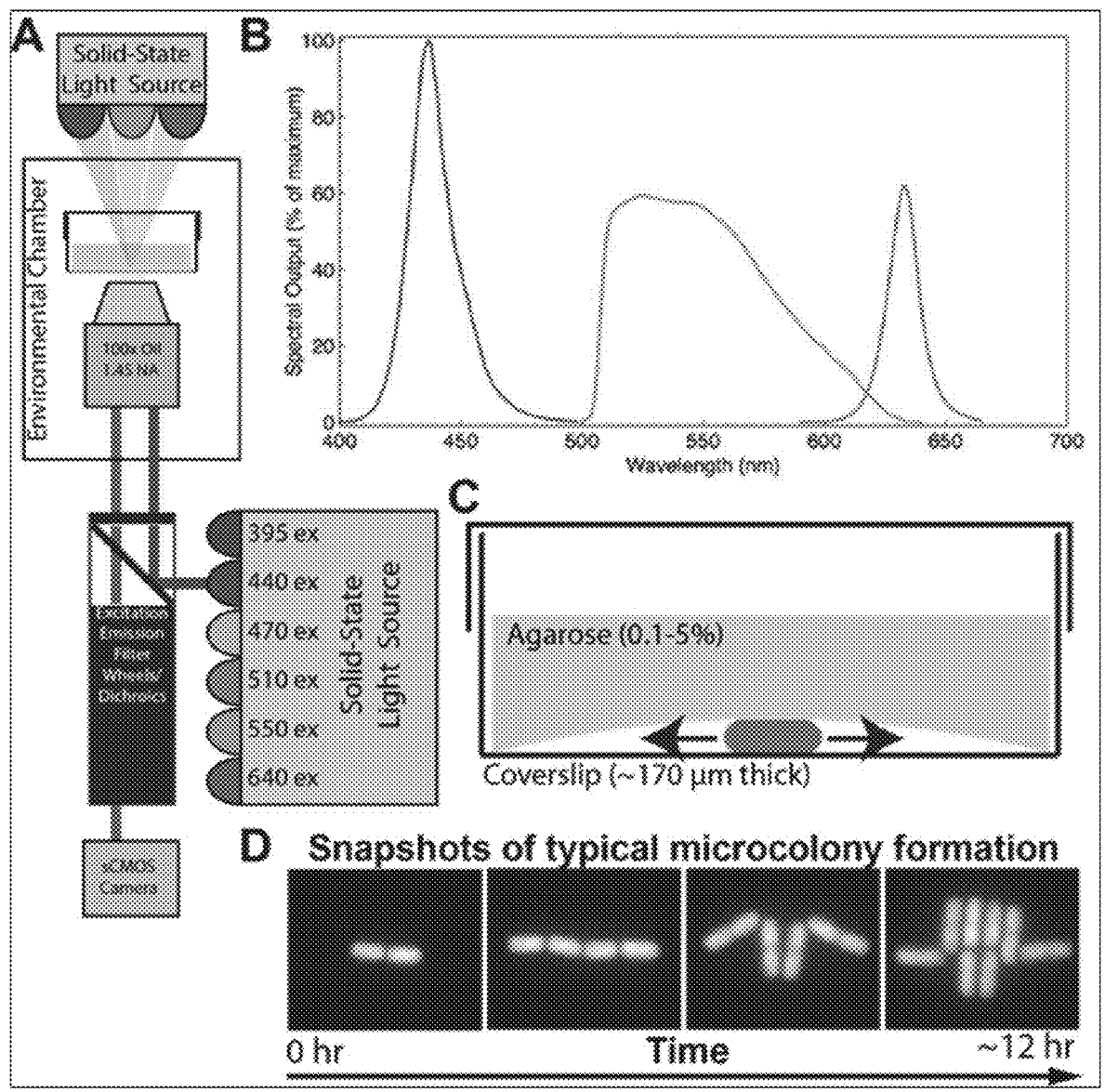
FIG. 6: Quantitative imaging platform. A) Microscope setup. B) Spectra of grow lights. C) 2-D agarose growth chamber. D) Cells.
Figure 7:
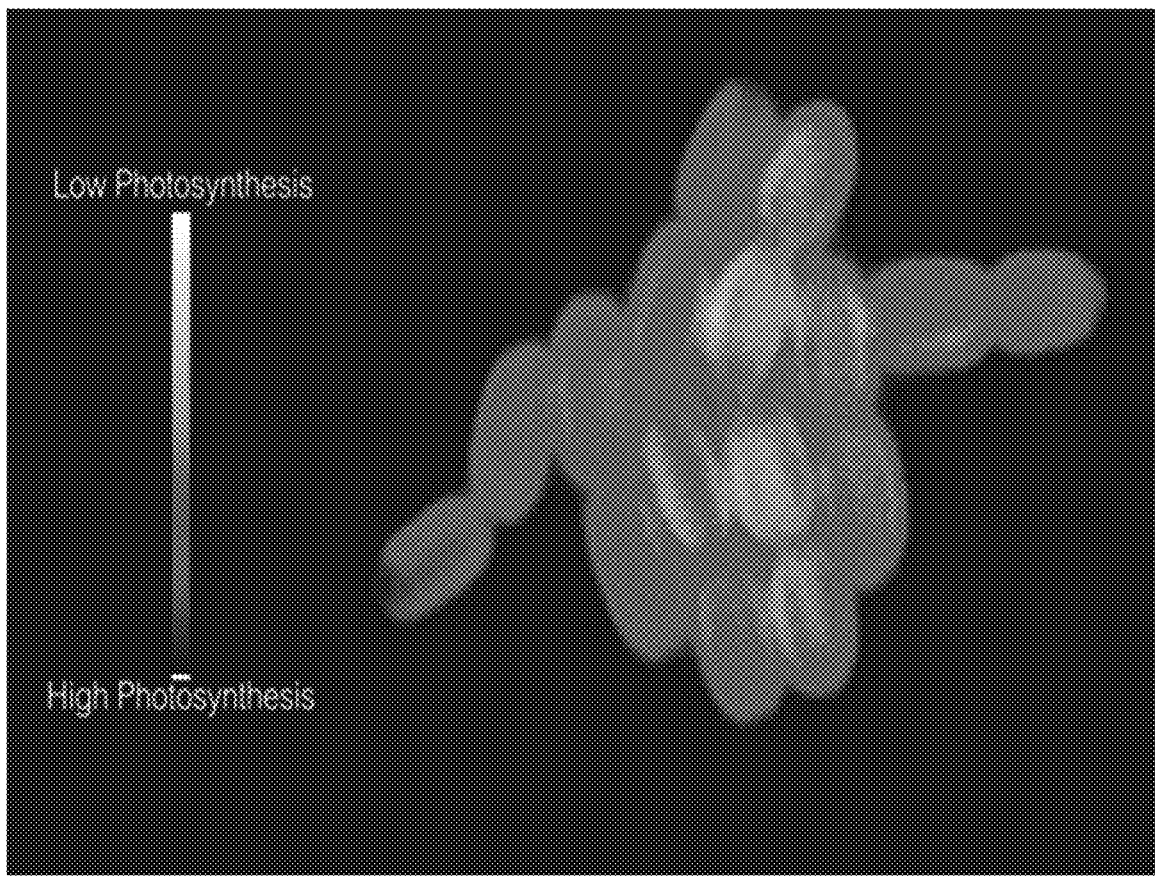
FIG. 7: Photosynthetic capacity in single-cell derived lineage. Highly fluorescent cells in the interior of the colony are facing high source:sink ratio and thus are attenuating the amount of photosynthesis in the interior.
Figure 8:
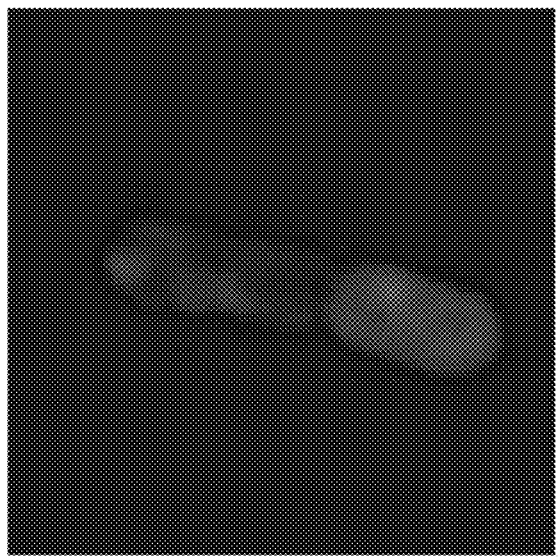
FIG. 8: Spectral resolution of phycobilisome decoupling during growth on 2.5% agar. Rights: Shows emission at 650 nm; Left: Emission Ratio: 650 nm (phycobilisome)/685 nm (chlorophyll).
Figure 8:
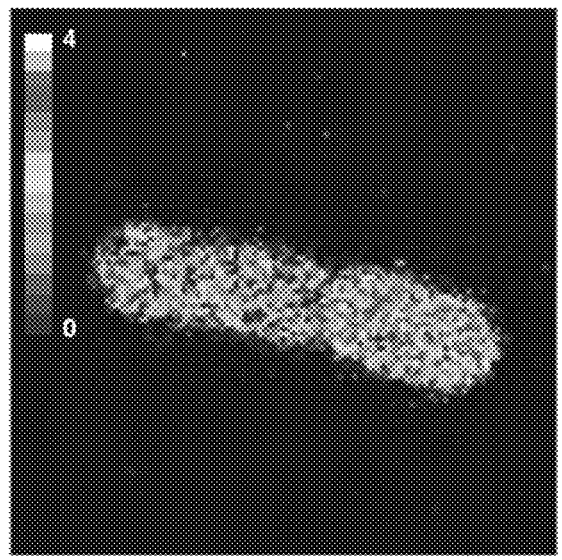
Figure 9:
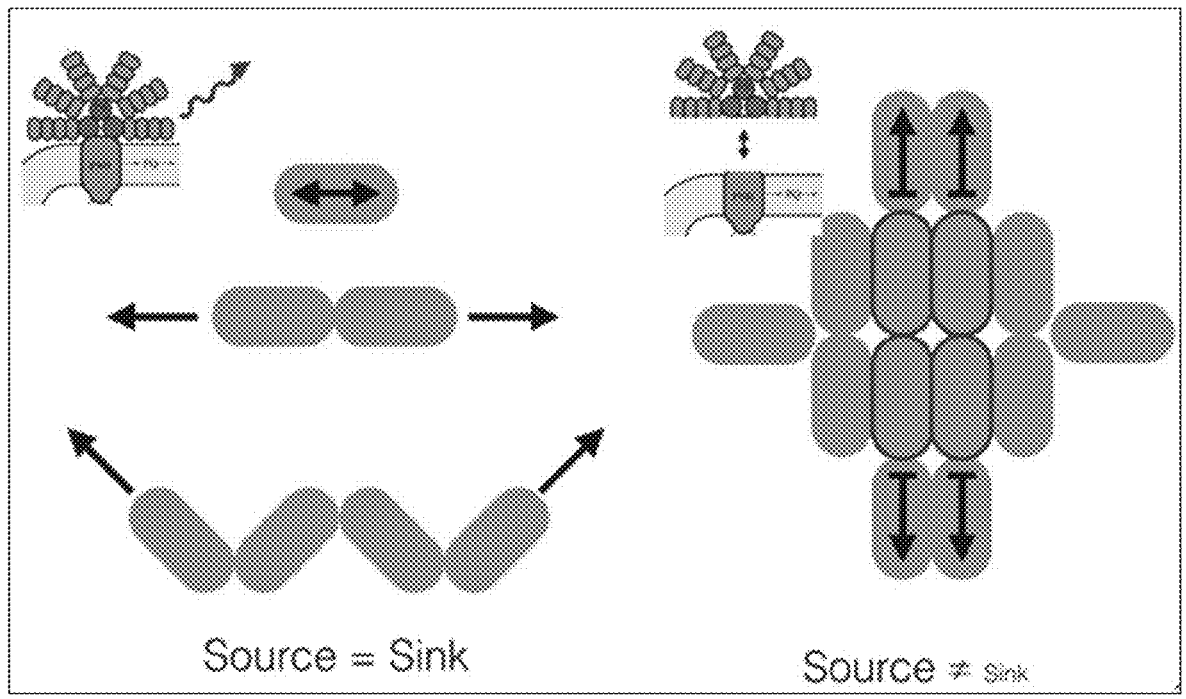
FIG. 9: Model for mechanical regulation of source:sink ratio and decoupling of phycobilisomes in microcolonies.
Figure 10:
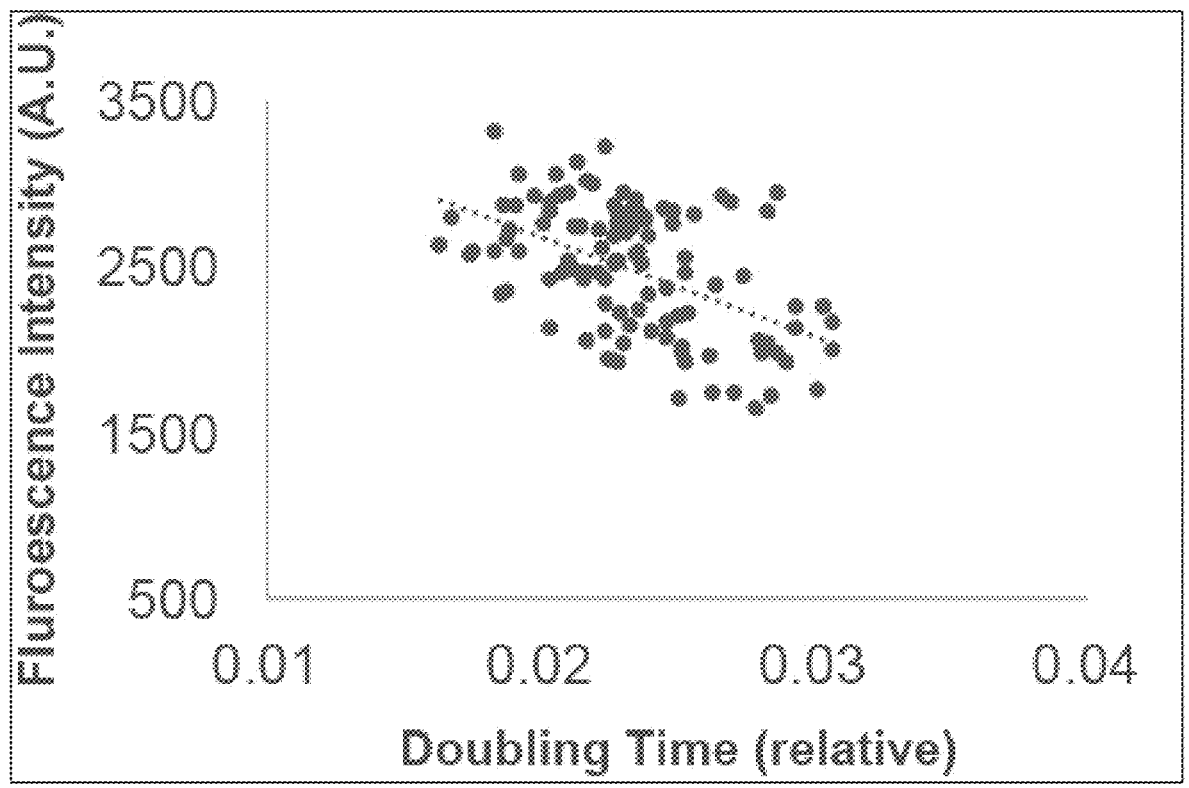
FIG. 10: Growth rate vs fluorescence intensity. An inverse relationship between fluorescence intensity and growth is observed, with increased fluorescence correlating with decreased growth.
Figure 11:
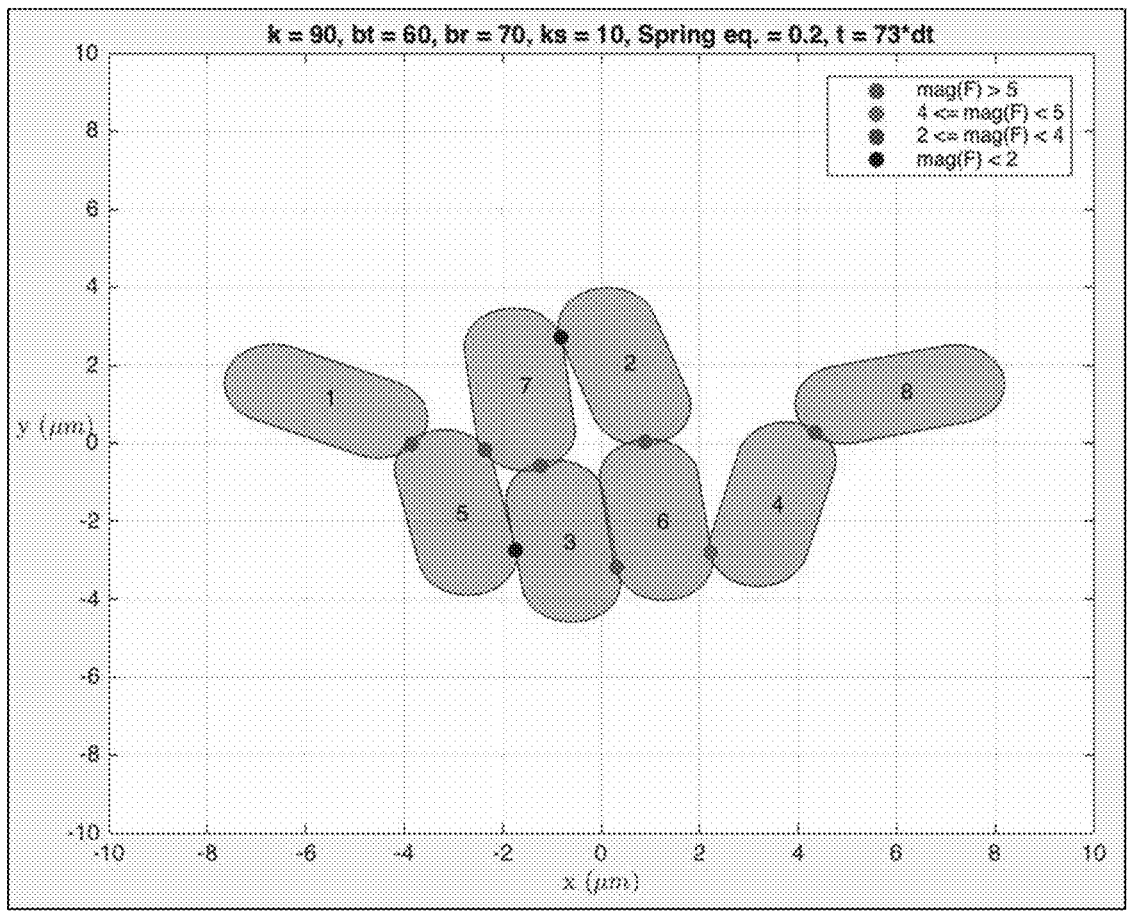
FIG. 11: Mechanical-based simulation of cyanobacterial colony formation on solid substrate. Relative magnitudes of mechanical forces between cells can be predicted and corresponds to cells exhibiting increased fluorescence.
Figure 12:
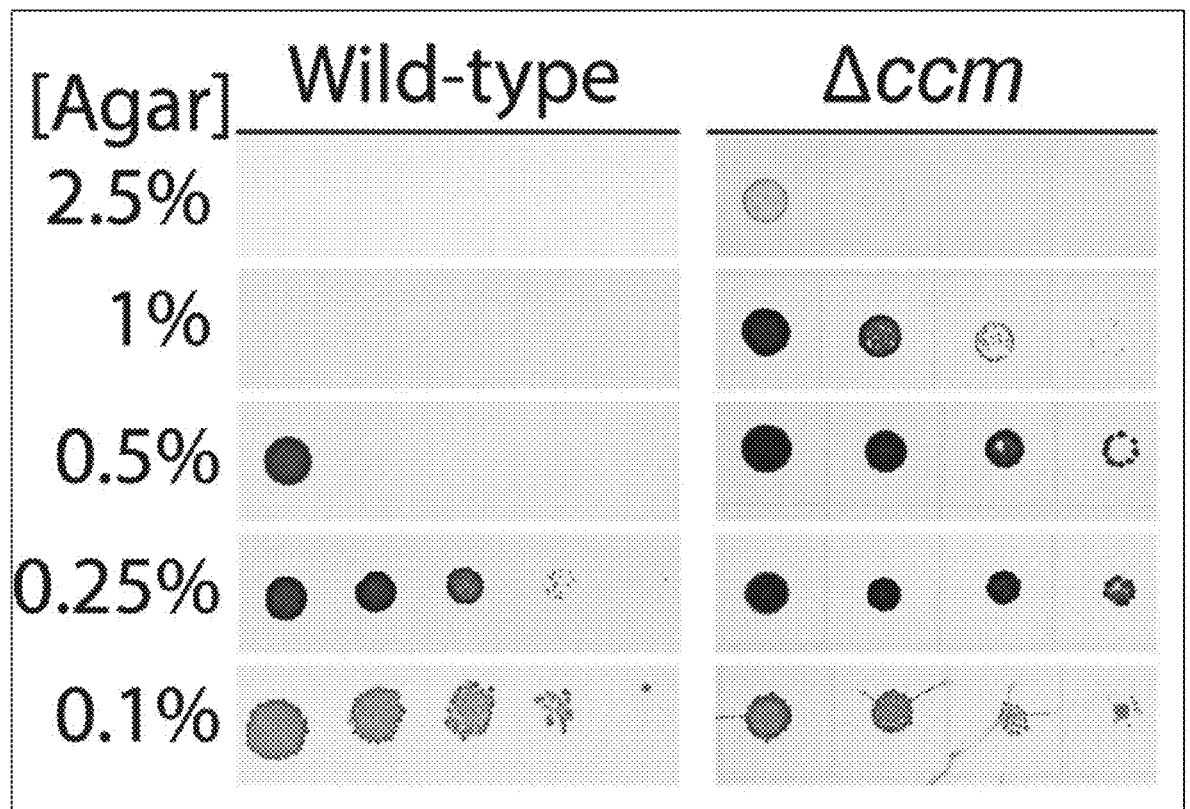
FIG. 12: Tuning growth/mechanical properties of *Synechococcus* sp. PCC 7002. Cells were grown in 3% $CO_2$. The Δccm mutant exhibits superior growth properties on stiff medium compared to the wild type. This setup could be used to identify mutants with enhanced or reduced ability to transduce light into mechanical energy.

As noted above, cyanobacteria are photosynthetic microbes that utilize light energy to catalyze water oxidation using multiple pigment-protein complexes. Electrons derived from water oxidation are used in reductive assimilation of $CO_2$. Because light is a substrate for cyanobacterial growth and the endogenous light-harvesting pigments are highly fluorescent, quantitative fluorescence microcopy and live-cell imaging of cyanobacteria has remained challenging. As generally shown in FIG. 6A. the present inventors demonstrate a customized microscope system specifically tailored for long-term growth and quantitative imaging of cyanobacterial cells. This system enables the present inventors to control incident growth light intensity and wavelength (RGB LEDs), temperature, and $CO_2$ concentration while monitoring fluorescence using specific filter cube sets and fluorophores compatible with endogenous background fluorescence. An automated focus system (Perfect Focus, Nikon) allows for stable, long-term fluorescence imaging for over 100 hours. The present inventors further developed image-processing techniques used to segment individual cells in time-series and extract multiple cellular parameters for each frame resulting in multi-dimensional phenotyping of cyanobacteria in single-cell derived lineages and populations. This includes single-cell growth rates, particle tracking (e.g. carboxysomes), and dynamics of other genetically encoded fluorescent sensors (eg. Calcium, pH). As generally shown in FIG. 11, utilizing this novel system, the present inventors can also measure the dynamics and kinetics of chlorophyll fluorescence in single cells to probe the photosynthetic activity of single cells at sub-cellular resolution.

The present inventors demonstrate that microcolony formation in PCC 7002 is highly reproducible for at least 4-5 doublings (16-32 cell stage) under standard growth conditions, producing compact structures of parallel cells flanked by perpendicular cells resembling "arms". Identical colony morphology was also evident during growth on the exposed surface of solid medium, indicating that this is not an artifact of 2-D confinement, but the native colony architecture. This distinct colony morphology preserves cell-lineage information and cell polarity, providing a the unique opportunity to determine the ancestry of each cell based on colony position alone and make pair-wise comparisons between specific cells in different colonies.

The present inventors demonstrated that the non-random distributions of cells within the colonies were driven by discrete mechanical interactions between adjacent cells. Specifically, the present inventors demonstrated a mathematical model that could accurately simulate the morphological growth dynamics and predict the relative mechanical forces acting on cells within the colony. Empirically derived model parameters including cell dimensions and growth rates, were extracted from time-series analysis of movies using custom in-house segmentation and cell-tracking algorithms. A purely stochastic model could not reproduce the colony dynamics of PCC 7002 in contrast to other Gram-negative bacteria such as *E. coli*. This implies that discrete physical forces overcome stochastic processes and strongly influence colony morphology in PCC 7002.

Figure 5:
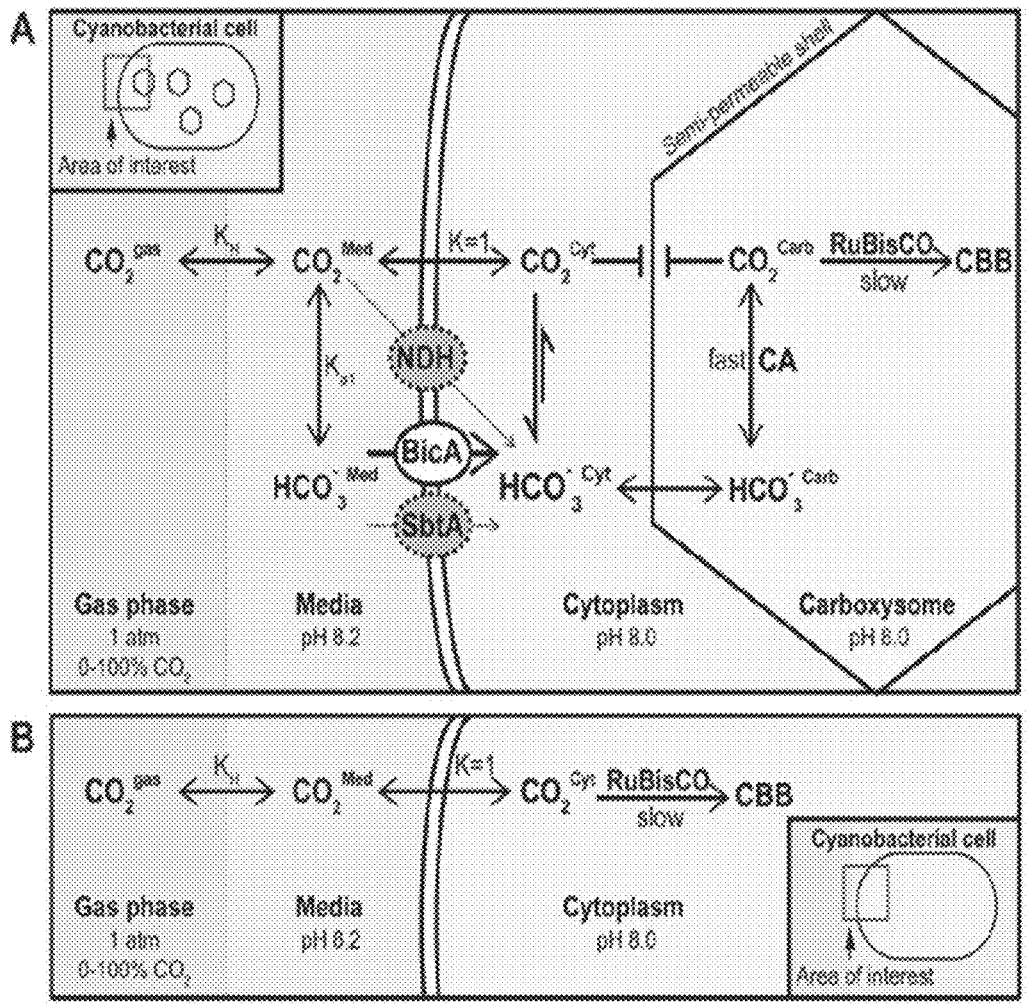
FIG. 5: Schematic of cyanobacterial $CO_2$ concentrating mechanism (CCM). A) Wild-type. B) Δccm mutant. From Clark et. al., *AiChE Journal* (2014)

Example 8: The Carboxysome is an Essential Component of the CO2 Concentrating Mechanism As discussed above, the carboxysome serves to increase the efficiency of carbon-fixation by concentrating the substrate, $CO_2$, in proximity to the RuBisCO active site. However, the present inventors demonstrate that the carboxysome does not function alone, but is instead a key component of the cyanobacterial $CO_2$-concentrating mechanism (CCM) (FIG. 5). The CCM is comprised of inorganic carbon (C) uptake systems and the carboxysome. In the alkaline, aqueous environments where cyanobacteria thrive, bicarbonate ($HCO_3^-$) is the predominant form of Ci. $HCO_3^-$ is actively taken up by the Na+-dependent transporters, BicA and SbtA, and an ATP-binding cassette transporter BCT1. $CO_2$ that enters the cell by passive diffusion is converted to $HCO_3^-$ by two NADPH dehydrogenase enzymes (Ndh-13 and Ndh-14). Ultimately, the combined activities of these transporters results in an accumulation of Ci in the cell at over 3 orders of magnitude higher than the external environment. $HCO_3^-$ then enters the carboxysome, where it is rapidly converted to $CO_2$ by carbonic anhydrase and subsequently reacted with ribulose 1,5-bisphosphate by RuBisCO to generate two molecules of 3-phosphoglycerate (3-PGA). This mechanism effectively saturates RuBisCO with substrate.

In addition, $CO_2$ fixation is the major sink for electrons derived from water during oxygenic photosynthesis. Thus, at high light intensities, carbon-fixation becomes limiting for growth. Importantly, carboxysomes are essential for cyanobacterial growth at ambient $CO_2$ concentrations (~0.04%), but are dispensable in laboratory conditions with elevated $CO_2$ (>1%). Thus, CCM mutants exhibit a high-$CO_2$ requiring (HCR) phenotype. This conditional lethality demonstrated by the present inventors provides a powerful platform for genetic manipulation and functional characterization of carboxysomes. In certain embodiments of the invention, mutants can be generated and maintained under non-essential conditions (high $CO_2$), and function can be assessed by monitoring growth/cellular physiology following a shift to limiting $CO_2$ concentrations (<1%).

MATERIALS AND METHODS

Example A: Growth and Maintenance of Cyanobacteria Strains

*Synechococcus* sp. PCC 7002 (Syn7002) is one of the fastest growing photoautotrophs identified to date, with a doubling-time of <3 hr under optimal conditions (compared to ~12-24 hr in Syn7942 and Syn6803). The fast growth rate and resistance to harsh environmental perturbations (e.g. nutrient limitation, high-light, salinity, temperature, etc.) has made Syn7002 the strain of choice for industrial applications seeking to convert $CO_2$ into fuels, chemicals, and other useful products. We will harness the diversity of these three strains to gain an evolutionary perspective on carboxysome inheritance and senescence. Because the optimal temperature requirements for Syn6803 and Syn7942 is 30° C. and 37° C. for Syn7002, the microbial cultivation facility in the Cameron Lab contains four identical Environmental Growth Chambers (Percival) to enable growth at two different temperatures (30° C. and 37° C.) and two different $CO_2$ concentrations (ambient and 3%).

The present inventors demonstrated the cultivation of strains *Synechococcus* sp. PCC 7002 in A+ media in an AL-41L4 Environmental Chamber and maintained at 37° C. Atmospheric $CO_2$ conditions and continuous illumniation (~150 umol photons m-2 s-1) provided by cool white fluorescent lamps. The present inventors futehr demonstrated the cultivation of PCC 7002 grown in 25 ml liquid cultures in baffled flasks (125 ml) contained with a foam stopper (Jaece identi-plug) and orbital shaking (200 rpm) or on medium solidified with Bacto Agar (0.5-1%; w/v). Antibiotics were provided to solid medium for routine maintenance of mutants when necessary (km, 30 µg/ml; sp, 25 µg/ml; gm, 30 µg/ml). Induction of the CRISPRi system was initiated by adding anhydrotetrocycline (aTC) at a concentration of 1 µg/mL.

Example B: Genetic Manipulation of Cyanobacteria

In one embodiment, the present inventors selected *Synechococcus elongatus* PCC 7002 PCC7002 as an exemplary cyanobacterium. This strain is genetically tractable, naturally competent for DNA uptake, and has an endogenous mechanism for efficient double-homologous recombination. This enables efficient gene targeting and replacement. Counter-selectable markers are also available for scar-free, genomic manipulations. Synthetic biology toolkits for inducible expression have also been made for each of these strains and an extensive set of fluorescent markers for visualizing and co-localizing carboxysome components has already been developed in by the present inventors (e.g. RbcL-CFP, RbcL-YFP, RbcL-GFP).

Example C: Strain and Plasmid Construction

Strains and plasmids used by the present inventors are described in Tables 1A-B below. The present inventors utilized wild-type (WT) *Synechococcus elongatus* PCC 7002 as the background strain for genetic manipulation. All plasmids created by the present inventors for this study were generated through gibson assembly of PCR amplified insert(s) and either JCC257 or pCas35 plasmid backbones. All cloning PCRs were performed with Phusion polymerase (Thermo Scientific). Cyanobacterial strains were created by transforming cells with noted plasmids or linearized PCR product amplified from plasmids, which included homologous regions as well as insert and selecting on prescribed antibiotic.

Specifically, cells from 1 day old cultures were incubated with 0.5-1.0 µg of DNA for 4-14 hr with continuous illumination before plating on solid media with antibiotics. Individual colonies were patched to new plates with single or combined antibiotics and checked for segregation through PCR with primers flanking the insert and/or gene specific primers depending on strain. Strains were determined to be segregated when no WT product could be detected. All cloning and segregation primers are listed in Table S2. To ensure full segregation of the ΔcpcB strain, both ΔcpcB and WT cells were spotted (7.5 µL of 2 day old culture diluted to 0.05 OD with 1:10 dilutions steps) on both 1% and 0.5% (w/v in A+ media) bacto agar. The plates were incubated at 37 C with constant light for 96 hr (0.5% plate) or 48 hr (1% plate). Absorbance spectra were also taken of ΔcpcB using a Tecan plate reader with 2 nm bandwidth from 350-750 nm. Mean absorbance values of three biological replicates are represented in FIG. S2. CRISPRi strains were freshly transformed for all experiments due to loss of knockdown over time.

Example D: Cell Imaging

The present inventors demonstrated time-lapse imaging of PCC 7002. Specifically, 2 µL of log phase cells were spotted on to noted percentage (w/v in A+ media) agarose pads and air dried before being inverted into a 35 mm glass bottom dish. No antibiotics were added to agarose pads for any movies. Cells were allowed to acclimate to microscope growth conditions (37 C and ~150 umol photons m-2 s-1 red light) for ~1 hr before imaging began. Four layers of filter paper soaked in 1M sodium bicarbonate surrounded the imaging dish. Later indication demonstrated to the present inventors that addition of sodium bicarbonate was not necessary for cell growth during imaging. Images were taken using the 470 nm, 508 nm, 555 nm, and 640 nm, Spectra X LED light source. The frame rate for all movies/images was 10 min. Cells were continuously illuminated with Red light for growth except during fluorescent imaging. CRISPRi lines were spotted on to pads containing 1 µg/ml aTC, and for FIG. 2G cells were mixed with Attune performance tracking beads (Invitrogen) that had been washed 3 times in sterilized water prior to spotting.

In one embodiment, microfluidics experiments were performed by the present inventors using the CellASIC ONIX microfluidic platform (Millipore). In this embodiment, cells were loaded into microfluidic plates for bacterial cell culture (Millipore—B04A-03-5PK) following recommended protocols. Cells were grown with a continuous flow of 50/50 fresh and filtered, pre-cultured media at a flow rate of 7 kPa. Growth conditions were the same as those noted above. Doubling time was calculated by hand for microfluidic experiments. Spectral imaging was performed by modifying the scope setup to include a Nikon C2 confocal scanhead and a DUS spectral detector using excitation at 632 nm.

Example E: Transmission Electron Microscopy

The present inventors demonstrated the growth of WT PCC 7002 cell on plates that were suspended in 100 mM mannitol in A+ media, high pressure frozen, freeze substituted in either 2% OsO4/0.1% uranyl acetate in acetone or 0.25% glutaraldehyde/0.1% uranyl acetate in acetone, and embedded in Epon/Araldite or HM20, respectively. Thick sections were collected on formvar coated copper slot grids and dual axis tilt series were acquired on an FEI Technai F30 IVEM (FEI, Eindhoven, Netherlands). Tomograms were processed using the IMOD software package.

Example F: Microcolony Imaging

Dialysis tubing was cut into single layers and placed on top of 1% (w/v in A+ media) agarose pads similar to those used for time lapse imaging. 2 µL of WT cells were spotted onto dialysis tubing and allowed to dry. Faceup agarose pads were enclosed in 35 mm plastic dishes and grown under the same conditions as for time-lapse imaging for approximately 16 hr. Microcolonies grown on dialysis tubing were plunge frozen in liquid ethane, using a manual plunge freezer. Cells and tubing were freeze substituted in 2%OsO4/0.1% uranyl acetate in acetone. Samples were flat embedded in Epon/Araldite on a glass slide and areas of interest were excised and remounted for sectioning. 100 nm sections were collected on formvar coated copper slot grids and post stained with 2% aqueous uranyl acetate and Reynold's lead citrate. An FEI Technai T12 TEM (FEI, Eindhoven, Netherlands) was used to image the cells.

Example G: Cell Segmentation

Automated analysis of the microscope images was carried out using custom code in MATLAB. First, images from the microscope were imported into MATLAB using the Bioformats Image Toolbox. Then, cells were identified (segmented) by applying an intensity threshold to individual frames. The threshold intensity was set either manually through trial-and-error or determined automatically using the intensity histogram of the image.

For the histogram method, it was assumed that most of the image was background, resulting in a large peak of pixel counts at the low intensity values. This background peak was identified, and fitted to a Gaussian distribution. The threshold intensity was then chosen to be the mean+<thFactor>* standard deviation of the fitted Gaussian. A binary image mask was then created by the present inventors setting pixels brighter than the threshold intensity as true. The initial mask was cleaned up by performing morphological opening with a 2 px radius disk-shaped structuring element and by filling isolated holes in the mask.

To separate cells which were clustered together, the distance transform of the mask was computed. The distance transform computes the distance of a pixel in the mask to the nearest background pixel. The watershed transform of the distance transform was then computed to separate individual cells. To avoid oversegmentation, the present inventos suppressed minima in the distance transform less than <MaxCellMinDepth>.

Finally, any cell masks which intersected with the image border (i.e. cells which are partially in the field of view) were removed. Data such as the cell length, width, and mean intensities were then calculated for each separate object in the mask. When necessary cell masks were adjusted by hand to omit size and tracking errors.

Example H: Linking Data to Form Tracks

The cell segmentation data collected by the present inventors was linked to form tracks of time series data belonging to the same cell. To link data from a single object between frames, the present inventors implemented a modified version of Jaqaman's tracking algorithm. Following Jaqaman's algorithm a cost matrix was computed. The Jonker-Volgenant algorithm was then used to assign data between frames such that the total cost is minimized.

Since the cyanobacteria cells are non-motile, the present inventors chose a cost function defined as the inverse of the ratio of the number of intersecting pixels over the total number of pixels between objects in consecutive frames. The present inventors used the inverse of the ratio since the Jonker-Volgenant algorithm aims to minimize the total cost. This cost was calculated for each object in the current frame with each object in the following frame to form the cost matrix. To avoid linking cells over physically impossible distances, the present inventors also specified a maximum linking distance. Objects which were separated by a distance above this maximum were assigned a score of infinity.

After running the assignment algorithm, some objects are not assigned (e.g. if they were too far apart from other unlinked cells). If an object was not linked with an object in a previous frame, the present inventors tested for cell division by computing the overlapping cost function between the unassigned object with objects in the previous frame. If the cost fell within a set value (1 and 8), then a division event was recorded and new daughter tracks were created.

Example I: Data Analysis

To determine the growth rate, the log of the length over time of each track was fit to a linear polynomial:

$$\log(L(t)) = \alpha t + \log(L_b)$$

where L(t) is the length of the cell at time t, $\alpha$ is the growth rate and $L_b$ is the length at birth of the cell. Doubling time was determined using the rate constant determined from equation X above. For FIGS. 2D and 3C, the intensity counts from within segmented cells for noted channels were summed and divided by cell area to determine mean intensity values per frame. Sum Mean Intensity in FIG. 4C is the result of the sum of the mean intensity counts collected from the cy5 channel over a cell track divided by track length to normalize for differences in cell lifespan.

Example J: Cell Properties and Growth

Each cell is modeled as a sphero-cylinder of fixed radius, r=1, and variable length, L, referring to the body axis of the cell (as shown below). At each time step, cell length is updated according to dL dt=gL, with division occurring once cell length reaches 2.5 times its radius. Following updates to cell growth, the force exerted on each cell by friction and cell-cell interactions is calculated and applied by integrating numerically the system of equations derived from Newtonian mechanics, thus updating cell position and orientation.

Initially, each cell grows at the average rate, gavg, taken to be 0.224 for an average doubling time of just over threehours. However, decreased photosynthetic activity for cells in the tightly packed colony interior suggests a slowdown in growth for these cells. Growth rate, g, then decreases linearly to a minimum of 0.218 as the total force acting on a particular cell increases.

Example K: Cell Division

Once a cell reaches the division length, its total mass is split evenly into two daughter cells. To reproduce the repeatedly observed W-shape in cyanobacteria micro-colonies, cell orientation is perturbed by an angle $\theta \in [\pm 1°, \pm 10°]$ according to cell position. Correcting for the fact that cell division does not occur instantaneously, a connection is maintained between recently divided cells, modeled as a spring, the strength of which falls o' linearly in time. The spring constant, ks, is given by ks(tconnected)=ks(1−tconnected/55), ensuring that the connection remains until the daughter cells begin to divide themselves.

Example L: Cell Mechanics

Cell mass and moment of inertia are functions of length and radius, and are therefore adjusted after each growth step. Cell density, $\rho$, is set at 1, the density of water. The following equations are adapted from [1] and [2].

Let $m_i$ be the mass of the $i^{th}$ cell:

$$m_i = \rho\left[\frac{4}{3}\pi r^3 + \pi r^2 L\right]$$

and $I_i$, its moment of inertia:

$$I_i = \frac{1}{48}\pi\rho(2r)^2 L^3 + \frac{3}{64}\pi\rho(2r)^4 L + \frac{1}{60}\pi\rho(2r)^5 + \frac{1}{24}\pi\rho 2r^3 L^2.$$

The net force acting on cell i is denoted Fi and has two components. These are, cell-cell elastic interactions, where $F_{ij}$ denotes the force exerted on cell i by cell j, and, the force of friction between a cell and surrounding substrate, $F_{cs}$. The following three equations govern the mechanics of the model where $\tau_i$ is the net torque acting on cell i and, $\omega_i$ is the angular velocity.

$$m_i \frac{d^2 x_i}{dt^2} = F_i \qquad (1)$$

$$I_i \frac{d\omega_i}{dt} = \tau_i \qquad (2)$$

$$\frac{du_i}{dt} = \omega_i \times u_i \qquad (3)$$

Example M: Cell-Cell Interactions

The force exerted by cell j on cell i is calculated as:

$$F_{ij} = k\Delta_{ij} n_{ij} \qquad (4)$$

where k is a constant for the strength of cell-cell interactions, $\Delta_{ij}$ is the amount of deformation which, if nonzero, signifies a repulsive interaction, and $n_{ij}$ is a unit vector indicating the direction of the force. To determine $\Delta_{ij}$ and nij, the cells are allowed to 'overlap', in theory, and the shortest distances between their body axes is computed. This defines contact points $t_i$ and $t_j$ on the body axes which then determine the direction of $F_{ij}$ from the unit normal vector:

$$\hat{n}_{ij} = \frac{t_i - t_j}{|t_i - t_j|}. \qquad (5)$$

If cells are nearly parallel, such that contact points cannot be uniquely identified, the centers are used as contact points instead: $t_i = x_i$ and $t_j = x_j$. The degree of overlap $\Delta ij$ is either zero, if 2r<s, in which case Fij vanishes or, it is nonzero if 2r>s suggesting that these cells do exert a force on one another.

Example M: Frictional Forces

Friction between cells and the substrate (agar gel pads), is proportional to the velocity, v, or angular velocity, $\omega_i$, of the cell with respect to the agar. Friction due to translational motion is given by:

$$F_{ca} = -b_t v \qquad (6)$$

where $b_t$ is the friction coefficient for translation. Net torque is given by:

$$\tau_i = (t_i - x_i) \times F_{ij} - b_r \omega_i \qquad (7)$$

where $b_r$ is the friction coefficient for rotation. Both friction coefficients were found "by trial and error." In the torque equation, $t_i$ is the point inside cell i where the force from cell j is most directly applied.

TABLES

TABLE 1A

Cyanobacteria Strains.
Synechococcus elongatus PCC 7002 strains

| Strains | Description | Resistance |
|---|---|---|
| WT | Wild-type Synechococcus elongatus 7002 | none |
| scJC0031 | WT cells transformed with KAMc0024 | Gm |
| scJC0102 | Deletion of cpcB operon with gentamycin cassette using KAMc0049 | Gm |
| scJC0091 | Deletion of A2810 (ocp) with gentamycin cassette using KAMc0082 | Gm |
| scJC0054 | WT cells transformed with pCas2F-SpR | Sp |
| KAMs0002 | scJC0054 transformed with KAMc0085 | Sp/Kan |
| scJC0087 | Deletion of mscS with gentamycin cassette | Gm |
| scJC0090 | Deletion of mscL with kanamycin cassette | Kan |
| KAMs0001 | scJC0054 transformed with pCas35 and KAMc0062 | Sp/Kan/Gm |
| scJC0300 | WT cells transformed with KAMc0125G | Gm |

TABLE 1B

Plasmids.
Plasmids

| Plasmid Name | Description | Neutral Site |
|---|---|---|
| JCCxxxx | generic glpK BB | glpK |
| KAMc0024 | Pcpt::YFP cloned downstream of gentamycin resistance casette in JCCxxxx backbone | glpK |
| KAMc0049 | Kanamycin cassette flanked by cpcB upstream and cpcF downstream sequence | NA |
| pCas2F-SpR | TetR::aTC-inducible dCas9::spR | acsA |
| pCas35 | sgRNA targeted cpcB with kanamycin resistance cassette | NS1 |

TABLE 1B-continued

Plasmids.
Plasmids

| Plasmid Name | Description | Neutral Site |
|---|---|---|
| KAMc0085 | pCas35 with sgRNA targeting frp | NS1 |
| KAMc0062 | Pcpt::GCaMP6f cloned downstream of gentamycin resistance cassette in JCCxxxx backbone | glpK |
| KAMc0125G | Pcpt::sfGFP cloned downstream of gentamycin resistance cassette in JCCxxxx backbone | glpK |

Those skilled in the art will appreciate, or be able to ascertain using no more than routine experimentation, further features and advantages of the invention based on the above-described embodiments. Accordingly, the invention is not to be limited by what has been particularly shown and described. All publications and references are herein expressly incorporated by reference in their entirety.

REFERENCES

The following references are hereby incorporated in their entirety by reference:

[1] Saha, R. et al. Reconstruction and Comparison of the Metabolic Potential of Cyanobacteria Cyanothece sp. ATCC 51142 and *Synechocystis* sp. PCC 6803. *PLoS One* 7, (2012).

[2] Gordon, G. C. et al. CRISPR interference as a titratable, trans-acting regulatory tool for metabolic engineering in the cyanobacterium *Synechococcus* sp. strain PCC 7002. *Metab. Eng.* 38, 170-179 (2016).

[3] Markley, A. L., Begemann, M. B., Clarke, R. E., Gordon, G. C. & Pfleger, B. F. Synthetic Biology Toolbox for Controlling Gene Expression in the Cyanobacterium *Synechococcus* sp. strain PCC 7002. *ACS Synth. Biol.* 140925064919003 (2014). doi:10.1021/sb500260k

[4] Yokoo, R., Hood, R. D. & Savage, D. F. Live-cell imaging of cyanobacteria. *Photosynth. Res.* (2014). doi: 10.1007/s 11120-014-0049-x

[5] Cameron, J. C., Wilson, S. C., Bernstein, S. L. & Kerfeld, C. A. Biogenesis of a bacterial organelle: The carboxysome assembly pathway. *Cell* 155, 1131-40 (2013).

[6] "The Open Microscopy Environment." Accessed Jan. 16, 2018. www.openmicroscopy.org/bio-formats/

[7] Jaqaman, K. et al. Robust single-particle tracking in live-cell time-lapse sequences. Nature Methods 5, 695-702 (2008).

[8] Jonker, R. and Volgenant, A. A shortest augmenting path algorithm for dense and sparse linear assignment problems. Computing 38: 325-340 (1987)

[9] Campos et al. A constant size extension drives bacterial cell size homeostasis. Cell 159, 1433-1446 (2014).

[10] Su, Pin-Tzu, Chih-Tang Liao, Jiunn-Ren Roan, et al. 'Bacterial Colony from Two-Dimensional Division to Three-Dimensional Development: E48098', PLoS One, vol. 7/no. 11, (2012).

[11] Allen, M. P., and D. J. Tildesley., 'Computer Simulation of Liquids', Anonymous Translator New York; Oxford [Oxfordshire], Clarendon Press, 1987).

What is claimed is:

1. A method for utilization of microbes for micron-scale transduction of kinetic energy comprising the steps of:
   establishing at least one photosynthetic microbe in a mechanically confined enclosure;
   establishing at least one movable element inserted into said mechanically confined enclosure and positioning said movable element so as to be responsive to said photosynthetic microbe;
   applying a light input to said photosynthetic microbe, wherein energy from said light input is converted by said photosynthetic microbe into kinetic energy, which is accompanied by growth of said photosynthetic microbe into a plurality of photosynthetic microbes;
   transferring said kinetic energy generated by said photosynthetic microbe to said movable element, causing said movable element to move and perform work in response to a kinetic force generated by said kinetic energy; and
   wherein the photosynthetic microbe is a Δcpc mutant of a cyanobacterium strain, which has a deletion in a cpc gene of phycobilisome.

2. The method of claim 1, wherein said step of applying said light input comprises the step of applying a light input that is tunable in either light intensity and/or light wavelength, and/or both.

3. The method of claim 1, wherein said cyanobacterium strain is *Synechococcus* sp. PCC 7002.

4. The method of claim 1, and further comprising the step of establishing a sensor configured to quantify an amount of work performed by said movable element.

5. The method of claim 4, further comprising the step of establishing a feedback control configured to regulate the movement of the movable element resulting from the kinetic energy output from said photosynthetic cyanobacterial mutant.

6. The method of claim 5, wherein said step f establishing a feedback control comprises the step of modulating the light input and/or wavelength applied to said photosynthetic cyanobacterial mutant.

7. A method for moving a micron-scale movable element comprising the steps of:
   establishing at least one photosynthetic cyanobacterium strain in a mechanically confined enclosure;
   inserting at least one micron-scale movable element into said mechanically confined enclosure and positioning said movable element so as to be responsive to said photosynthetic cyanobacterium strain; and
   applying a light input to said photosynthetic cyanobacterium strain wherein energy from said light input causes the cyanobacterium strain to prow, which causes a kinetic force to be applied to the movable element and causing it to move and perform work.

8. The method of claim 7, wherein said step of applying a light input comprises the step of modulating intensity of the light input and/or wavelength of said light input, causing a reduction or increase in the work performed by the movable element.

* * * * *